(12) United States Patent
Stone

(10) Patent No.: US 11,396,647 B2
(45) Date of Patent: *Jul. 26, 2022

(54) HUMAN METHYLTHIOADENOSINE/ADENOSINE DEPLETING ENZYME VARIANTS FOR CANCER THERAPY

(71) Applicant: BOARD OF REGENTS, THE UNIVERSITY OF TEXAS SYSTEM, Austin, TX (US)

(72) Inventor: Everett Stone, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/427,519

(22) PCT Filed: Jan. 6, 2021

(86) PCT No.: PCT/US2021/012291
§ 371 (c)(1),
(2) Date: Jul. 30, 2021

(87) PCT Pub. No.: WO2021/141977
PCT Pub. Date: Jul. 15, 2021

(65) Prior Publication Data
US 2022/0042001 A1 Feb. 10, 2022

Related U.S. Application Data

(60) Provisional application No. 62/958,161, filed on Jan. 7, 2020.

(51) Int. Cl.
| | | |
|---|---|---|
| C12N 9/10 | (2006.01) | |
| A61K 47/60 | (2017.01) | |
| C07K 16/28 | (2006.01) | |
| A61P 35/00 | (2006.01) | |
| A61K 38/45 | (2006.01) | |
| A61K 45/06 | (2006.01) | |

(52) U.S. Cl.
CPC ............ *C12N 9/1077* (2013.01); *A61K 38/45* (2013.01); *A61K 45/06* (2013.01); *A61K 47/60* (2017.08); *A61P 35/00* (2018.01); *C07K 16/2818* (2013.01); *C12Y 204/02028* (2013.01)

(58) Field of Classification Search
CPC .. C12N 9/1077; A61K 47/60; C07K 16/2818; C12Y 204/02028
See application file for complete search history.

(56) References Cited

U.S. PATENT DOCUMENTS

| | | |
|---|---|---|
| 4,870,287 A | 9/1989 | Cole et al. |
| 5,739,169 A | 4/1998 | Ocain et al. |
| 5,760,395 A | 6/1998 | Johnstone |
| 5,801,005 A | 9/1998 | Cheever et al. |
| 5,824,311 A | 10/1998 | Greene et al. |
| 5,830,880 A | 11/1998 | Sedlacek et al. |
| 5,844,905 A | 12/1998 | McKay et al. |
| 5,846,945 A | 12/1998 | McCormick |
| 5,885,796 A | 3/1999 | Linsley et al. |
| 5,889,155 A | 3/1999 | Ashkenazi et al. |
| 6,207,156 B1 | 3/2001 | Kuchroo et al. |
| 6,870,037 B1 | 3/2005 | Olopade |
| 7,192,711 B2 | 3/2007 | Olopade |
| 7,829,673 B2 | 11/2010 | De Weers et al. |
| 8,008,449 B2 | 8/2011 | Korman et al. |
| 8,017,114 B2 | 9/2011 | Korman et al. |
| 8,119,129 B2 | 2/2012 | Jure-Kunkel et al. |
| 8,329,867 B2 | 12/2012 | Lazar et al. |
| 8,354,509 B2 | 1/2013 | Carven et al. |
| 8,735,553 B1 | 5/2014 | Li et al. |
| 11,118,167 B2 | 9/2021 | Stone et al. |
| 2004/0005647 A1 | 1/2004 | Denardo et al. |
| 2004/0247600 A1 | 12/2004 | Leoni |
| 2006/0063172 A1 | 3/2006 | Nobori et al. |
| 2007/0092968 A1 | 4/2007 | Ji et al. |
| 2009/0304666 A1 | 12/2009 | Harrison et al. |
| 2011/0008369 A1 | 1/2011 | Finnefrock et al. |
| 2011/0053236 A1 | 3/2011 | Walmsley et al. |
| 2014/0022021 A1 | 1/2014 | Kusachi |
| 2014/0220012 A1 | 8/2014 | Noelle et al. |
| 2014/0294898 A1 | 10/2014 | Miller et al. |

(Continued)

FOREIGN PATENT DOCUMENTS

| | | |
|---|---|---|
| WO | WO 95/01994 | 1/1995 |
| WO | WO 98/42752 | 10/1998 |

(Continued)

OTHER PUBLICATIONS

Olapade et al. Proc. Natl. Acad. Sci. (1995) 92: 6489-6493 (Year: 1995).*
Appleby et al., "The structure of human 5'-deoxy-5'-methylthioadenosine phosphorylase at 1.7 Å resolution provides insights into substrate binding and catalysis," *Structure*, 7(6):629-41, 1999.
Austin-Ward & Villaseca, "La terapia génica y sus aplicaciones," Revista Medica de Chile, 126(7):838-845, 1998. (English Abstract).
Bertino et al., "Targeting tumors that lack methylthioadenosine phosphorylase (MTAP) activity: current strategies," *Cancer Biology & Therapy*, 11(7):627-632, 2011.
Bradford et al., "Adenosine deaminase (ADA)-deficient severe combined immune deficiency (SCID): molecular pathogenesis and clinical manifestations," *Journal of Clinical Immunology*, 37(7):626-637, 2017.

(Continued)

*Primary Examiner* — Susan M Hanley
(74) *Attorney, Agent, or Firm* — Parker Highlander PLLC

(57) ABSTRACT

Disclosed herein are compositions related to conjugated polypeptides with MTA/ADO-degrading enzyme activity. The conjugated polypeptides are engineered to allow for maximal conjugation while maintaining catalytic activities. Also disclosed are nucleic acids, expression vectors, and host cells related to the conjugated polypeptides. Further disclosed are methods of using the pharmaceutical formulations comprising above to treat cancer.

19 Claims, 13 Drawing Sheets

Specification includes a Sequence Listing.

(56) References Cited

U.S. PATENT DOCUMENTS

| | | |
|---|---|---|
| 2021/0054350 A1 | 2/2021 | Stone et al. |
| 2021/0095264 A1 | 4/2021 | Stone et al. |

FOREIGN PATENT DOCUMENTS

| | | |
|---|---|---|
| WO | WO 00/37504 | 6/2000 |
| WO | WO 01/14424 | 3/2001 |
| WO | WO 2004/074325 | 9/2004 |
| WO | WO 2006/105021 | 10/2006 |
| WO | WO 2006/121168 | 11/2006 |
| WO | WO 2009/101611 | 8/2009 |
| WO | WO 2009/114335 | 9/2009 |
| WO | WO 2010/027827 | 3/2010 |
| WO | WO 2011/066342 | 6/2011 |
| WO | WO 01/83780 | 11/2011 |
| WO | WO 2012/032433 | 3/2012 |
| WO | WO 2012/131052 | 10/2012 |
| WO | WO 2015/016718 | 2/2015 |
| WO | WO 2015/033299 | 3/2015 |
| WO | WO 2015/033301 | 3/2015 |
| WO | WO 2015/097536 | 7/2015 |
| WO | WO 2015/116539 | 8/2015 |
| WO | WO 2015/117002 | 8/2015 |
| WO | WO 2016/028656 | 2/2016 |
| WO | WO 2016/038550 | 3/2016 |
| WO | WO 2016/059602 | 4/2016 |
| WO | WO 2016/154177 | 9/2016 |
| WO | WO 2016/207717 | 12/2016 |
| WO | WO 2017/019846 | 2/2017 |
| WO | WO 2017/030823 | 2/2017 |
| WO | WO 2017/130076 | 8/2017 |
| WO | WO 2017/137830 | 8/2017 |
| WO | WO 2017/175058 | 10/2017 |
| WO | WO 2017/182672 | 10/2017 |
| WO | WO 2017/220569 | 12/2017 |
| WO | WO 2018/002339 | 1/2018 |
| WO | WO 2018/039020 | 3/2018 |
| WO | WO 2018/085469 | 5/2018 |
| WO | WO 2018/091740 | 5/2018 |
| WO | WO 2018/187191 | 10/2018 |
| WO | WO 2018/201096 | 11/2018 |
| WO | WO 2018/202649 | 11/2018 |
| WO | WO 2019/126455 | 6/2019 |

OTHER PUBLICATIONS

Bukowski et al., "Signal transduction abnormalities in T lymphocytes from patients with advanced renal carcinoma: clinical relevance and effects of cytokine therapy," *Clinical Cancer Res.*, 4(10):2337-2347, 1998.

Camacho et al., "Phase 1 clinical trial of anti-CTLA4 human monoclonal antibody CP-675,206 its patients (pts) with advanced solid malignancies," *J. Clin. Oncology*, 22(145): Abstract No. 2505 (antibody CP-675206), 2004.

Camacho-Vanegas et al., "Primate genome gain and loss: a bone dysplasia, muscular dystrophy, and bone cancer syndrome resulting from mutated retroviral-derived MTAP transcripts," *The American Journal of Human Genetics*, 90(4):614-627, 2012.

Castle et al., "Immunomic, genomic and transcriptomic characterization of CT26 colorectal carcinoma," *BMC Genomics*, 15:190, 2014.

Christodoulides et al., "Immunization with recombinant class 1 outer-membrane protein from Neisseria meningitidis: influence of liposomes and adjuvants on antibody avidity, recognition of native protein and the induction of a bactericidal immune response against meningococci," *Microbiology*, 144(Pt 11):3027-3037, 1998.

Davidson et al., "Intralesional Cytokine Therapy in Cancer: A Pilot Study of GM-CSF Infusion in Mesothelioma," *J. Immunother.*, 21(5):389-398, 1998.

English Translation of WO 01/83780, provided by the International Search Authority on Sep. 5, 2019.

Gao et al., "Loss of IFN-γ pathway genes in tumor cells as a mechanism of resistance to anti-CTLA-4 therapy," *Cell*, 167(2):397-404, 2016.

Gill & von Hippel, "Calculation of protein extinction coefficients from amino acid sequence data," *Anal. Biochem.*, 182(2):319-326, 1989.

Hanibuchi et al., "Therapeutic efficacy of mouse-human chimeric anti-ganglioside GM2 monoclonal antibody against multiple organ micrometastases of human lung cancer in NK cell-depleted SCID mice," *Int. J. Cancer*, 78(4):480-485, 1998.

Harkki et al., "A Novel Fungal Expression System: Secretion of Active Calf Chymosin from the Filamentous Fungus *Trichoderma reesei*," *BioTechnology*, 7:596-603, 1989.

Hellstrand et al., "Histamine and cytokine therapy," *Acta Oncologica*, 37(4):347-353, 1998.

Henrich et al., "Suppressive effects of tumor cell-derived 5'-deoxy-5'-methylthioadenosine on human T cells," *OncoImmunology*, 5(8):e1184802, 2016.

Hollander, "Immunotherapy for B-cell lymphoma: current status and prospective advances," *Front. Immun.*, 3:3, 2012.

Hoover et al., "The structure of human macrophage inflammatory protein-3alpha /CCL20. Linking antimicrobial and CC chemokine receptor-6-binding activities with human beta-defensins," *J. Biol. Chem.*, 277(40):37647-37654, 2002.

Hui & Hashimoto, "Pathways for Potentiation of Immunogenicity during Adjuvant-Assisted Immunizations with Plasmodium falciparum Major Merozoite Surface Protein 1," *Infection Immun.*, 66(11):5329-5336, 1998.

Hurwitz et al., "CTLA-4 blockade synergizes with tumor-derived granulocyte-macrophage colony-stimulating factor for treatment of an experimental mammary carcinoma," *Proc. Natl. Acad. Sci. USA*, 95(17):10067-10071, 1998.

International Preliminary Report on Patentability issued in International Application No. PCT/US18/66731, dated Jul. 2, 2020.

International Search Report and Written Opinion issued in International Application No. PCT/US18/66731, dated May 9, 2019.

Invitation to Pay Additional Fees issued in International Application No. PCT/US18/66731, dated Mar. 12, 2019.

Iordanescu, "Recombinant plasmid obtained from two different, compatible staphylococcal plasmids," *J. Bacteriol.*, 12:597-601, 1975.

Ito et al., "Purification and Characterization of Methioninase from *Pseudomonas putida*," *J. Biochem.*, 79:1263-1272, 1976.

Jena et al., "Redirecting T-cell specificity by introducing a tumor-specific chimeric antigen receptor," *Blood*, 116(7):1035-1144, 2010.

Jiang et al., "Comprehensive evaluation of NT5E/CD73 expression and its prognostic significance in distinct types of cancers," *BMC Cancer*, 18:267, 2018.

Kadariya et al., "Mice heterozygous for germ-line mutations in methylthioadenosine phosphorylase (MTAP) die prematurely of T-cell lymphoma," *Cancer Research*, 69(14):5961-5969, 2009.

Keyel et al., "Methylthioadenosine reprograms macrophage activation through adenosine receptor stimulation," *PLoS One*, 9(8):e104210, 2014.

Kim et al., "Downregulation of methylthioadenosine phosphorylase by homozygous deletion in gastric carcinoma," *Genes, Chromosomes and Cancer*, 50(6):421-433, 2011.

Kirovski et al., "Down-regulation of methylthioadenosine phosphorylase (MTAP) induces progression of hepatocellular carcinoma via accumulation of 5'-deoxy-5'-methylthioadenosine (MTA)," *American Journal of Pathology*, 178(3):1145-1152, 2011.

Lewandowski et al., "Towards area-based in vitro metabolic engineering: Assembly of Pfs enzyme onto patterned microfabricated chips." *Biotechnology Progress*, 24(5):1042-1051, 2008.

Marjon et al., "MTAP Deletions in Cancer Create Vulnerability to Targeting of the MAT2A/PRMT5/RIOK1," *Axis. Cell Rep.*, 15(3):574-587 2016.

Mellor et al., "Efficient synthesis of enzymatically active calf chymosin in *Saccharomyces cerevisiae*," *Gene*, 24:1-14, 1983.

Mokyr et al., "Realization of the Therapeutic Potential of CTLA-4 Blockade in Low-Dose Chemotherapy-treated Tumor-bearing Mice," *Cancer Res*, 58:5301-5304, 1998.

(56) References Cited

OTHER PUBLICATIONS

Morello et al., "Soluble CD73 as biomarker in patients with metastatic melanoma patients treated with nivolumab," *Journal of Translational Medicine*, 15:244, 2017.
Nassar et al., "A model combining clinical and genomic factors to predict response to PD-1/PD-L1 blockade in advanced urothelial carcinoma," *Br. J. Cancer*, 122(4):555-563, 2020.
Nechushtan et al., "Adenocarcinoma cells are targeted by the new GnRH-PE66 chimeric toxin through specific gonadotropin-releasing hormone binding sites," *J. Biol. Chem.*, 272(17):11597-11603, 1997.
Office Communication issued in U.S. Appl. No. 16/950,622, dated Apr. 5, 2021.
Office Communication issued in U.S. Appl. No. 16/950,622, dated Aug. 4, 2021.
Onda et al., "In vitro and in vivo cytotoxic activities of recombinant immunotoxin 8H9(Fv)-PE38 against breast cancer, osteosarcoma, and neuroblastoma," *Cancer Research*, 64(4):1419-1424, 2004.
Pardoll, "The blockade of immune checkpoints in cancer immunotherapy," *Nat Rev Cancer*, 12(4):252-264, 2012.
Park et al., "Treating cancer with genetically engineered T cells," *Trends Biotechnol.*, 29(11):550-557, 2011.
Penttila et al., "A versatile transformation system for the cellulolytic filamentous fungus *Trichoderma reesei*," *Gene*, 61:155-164, 1987.
Peters et al., "A mouse model for cystinuria type I," *Hum. Mol. Genet.*, 12:2109-2120, 2003.
Qin, Xiao-Qiang, et al. "Interferon-β gene therapy inhibits tumor formation and causes regression of established tumors in immune-deficient mice." *Proceedings of the National Academy of Sciences* 95.24 (1998): 14411-14416.
Rau et al., "Single-chain Fv antibody-alkaline phosphatase fusion proteins produced by one-step cloning as rapid detection tools for ELISA," *Journal of Immunoassay and Immunochemistry*, 23(2):129-143, 2002.
Rizvi et al., "Molecular Determinants of Response to Anti-Programmed Cell Death (PD)-1 and Anti-Programmed Death-Ligand 1 (PD-L1) Blockade in Patients With Non-Small-Cell Lung Cancer Profiled With Targeted Next-Generation Sequencing," *J. Clin. Oncol.*, 36(7):633-641, 2018.
Schellenberger, Volker, et al. "A recombinant polypeptide extends the in vivo half-life of peptides and proteins in a tunable manner." *Nature biotechnology* 27.12 (2009): 1186-1190.
Schneider et al., "NIH Image to ImageJ: 25 Years of Image Analysis," *Nature Methods*, 9:2012.
Sek et al., "Targeting Adenosine Receptor Signaling in Cancer Immunotherapy," *International J. of Mol. Sciences*, 19:3837, 2018.
Sibakov et al., "Isolation and the 5'-end nucleotide sequence of *Bacillus licheniformis* a-amylase genem" *Eur. J. Biochem.*, 145:567-572, 1984.
Singh et al., "Picomolar transition state analogue inhibitors of human 5'-methylthioadenosine phosphorylase and X-ray structure with MT-Immucillin-A," *Biochemistry*, 43(1):9-18, 2004.
Stevens et al., "Direct and tumor microenvironment mediated influences of 5'-deoxy-5'-(methylthio) adenosine on tumor progression of malignant melanoma," *Journal of Cellular Biochemistry*, 106(2):210-219, 2009.
Stevens et al., "Quantification of intermediates of the methionine and polyamine metabolism by liquid chromatography-tandem mass spectrometry in cultured tumor cells and liver biopsies," *Journal of Chromatography A*, 1217(19):3282-3288, 2010.
Stevens et al., "Quantitative analysis of 5'-deoxy-5'-methylthioadenosine in melanoma cells by liquid chromatography-stable isotope ratio tandem mass spectrometry," *Journal of Chromatography B*, 876(1):123-128, 2008.
Stone et al., "Strategies for optimizing the serum persistence of engineered human arginase I for cancer therapy," *Journal of Controlled Release*, 158:171-179, 2012.
Strobl et al., "Selective PRMT5 Inhibitors Suppress Human CDS + T Cells by Upregulation of p53 and Impairment of the AKT Pathway Similar to the Tumor Metabolite MTA," *Molecular Cancer Therapeutics*, 19(2):409-419, 2020.
Sun et al., "Fasting inhibits colorectal cancer growth by reducing M2 polarization of tumor-associated macrophages," *Oncotarget*, 8:74649-74660, 2017.
Tiziani et al., "Metabolomics of the tumor microenvironment in pediatric acute lymphoblastic leukemia," *PLoS One*, 8:e82859, 2013.
Tiziani et al., "Optimized metabolite extraction from blood serum for 1H nuclear magnetic resonance spectroscopy," *Analytical Biochemistry*, 377:16-23, 2008.
Vandenbark et al., "Inhibition of lymphocyte transformation by a naturally occurring metabolite: 5'-Methylthioadenosine," *Cellular Immunology*, 49(1):26-33, 1980.
Vijayan et al., "Targeting immunosuppressive adenosine in cancer," *Nature Reviews Cancer*, 17:709, 2017.
Von Minckwitz et al., "Phase I clinical study of the recombinant antibody toxin scFv(FRP5)-ETA specific for the ErbB2/HER2 receptor in patients with advanced solid malignomas," *Breast Cancer Research*, 7(5):R617-R626, 2005.
Ward, Heterologous gene expression in Aspergillus. In: *Proceedings of the EMBO-ALKO Workshop on Molecular Biology of Filamentous Fungi*. Nevalainen, H. and Penttila, M. (Eds.). Foundation for Biotechnical and Industrial Fermentation Research, Helsinki, 6:119-128, 1989.
Webb et al., "PRMT5-Selective Inhibitors Suppress Inflammatory T Cell Responses and Experimental Autoimmune Encephalomyelitis." *Journal of Immunology*, 198(4):1439-1451, 2017.
Winthrop et al., "Selection and characterization of anti-MUC-1 scFvs intended for targeted therapy," *Clinical Cancer Research*, 9(10 Pt 2):3845S-3853S, 2003.
Woollard et al., "Independent Loss of Methylthioadenosine Phosphorylase (MTAP) in Primary Cutaneous T-Cell Lymphoma," *Journal of Investigative Dermatology*, 136(6):1238-1246, 2016.
Yu et al., "Ecto-5'-nucleotidase expression is associated with the progression of renal cell carcinoma," *Oncology Letters*, 9:2485-2494, 2015.
Dozier & Distefano, "Site-specific PEGylation of therapeutic proteins," *International Journal of Molecular Sciences*, 16.10:25831-25864, 2015.
International Search Report and Written Opinion issued in International Application No. PCT/US21/12291, dated Apr. 28, 2021.
Peciak et al., "Site-selective protein conjugation at histidine," *Chemical Science*, 10:427-439, 2019.
Christopher et al., "Methylthioadenosine phosphorylase, a gene frequently codeleted with p16cdkN2a/ARF, acts as a tumor suppressor in a breast cancer cell line," Cancer Res., 62:6639-6944, 2002.
Fishburn et al., "The pharmacology of PEGylation: Balancing PD with PK to generate novel therapeutics," Journal of Pharmaceutical Sciences, 97:4167-4183, 2008.
Munshi et al., "6-thioguanine: a drug with unrealized potential for cancer therapy," Oncologist, 19:760-765, 2014.
Nobori et al., "Genomic cloning of methylthioadenosine phosphorylase: A purine metabolic enzyme deficient in multiple different cancers," PNAS, 93:6203-6208, 1996.
Office Communication issued in U.S. Appl. No. 16/956,340, dated Nov. 17, 2021.
Office Communication issued in U.S. Appl. No. 17/516,639, dated Feb. 1, 2022.
Podust et al., "Extension of in vivo half-life of biologically active molecules by XTEN protein polymers," J. Controlled Release, 240:52-66, 2016.
Sleep et al, "Albumin as a versatile platform for drug half-life extension," Biochimica et Biophysica Acta, 1830: 5526-5534, 2013.

\* cited by examiner

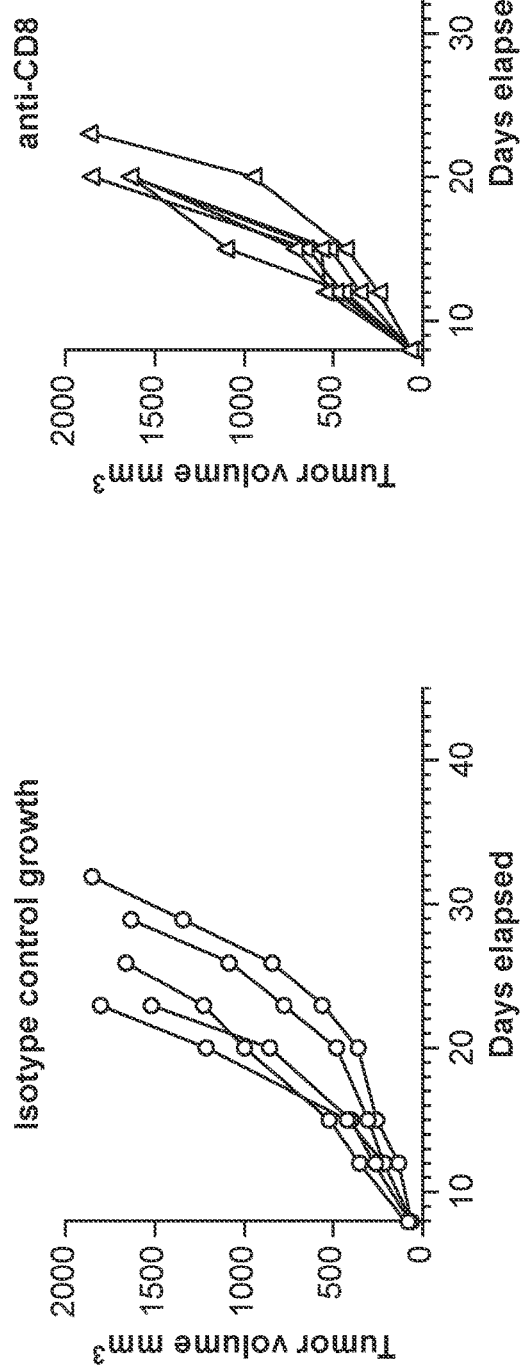
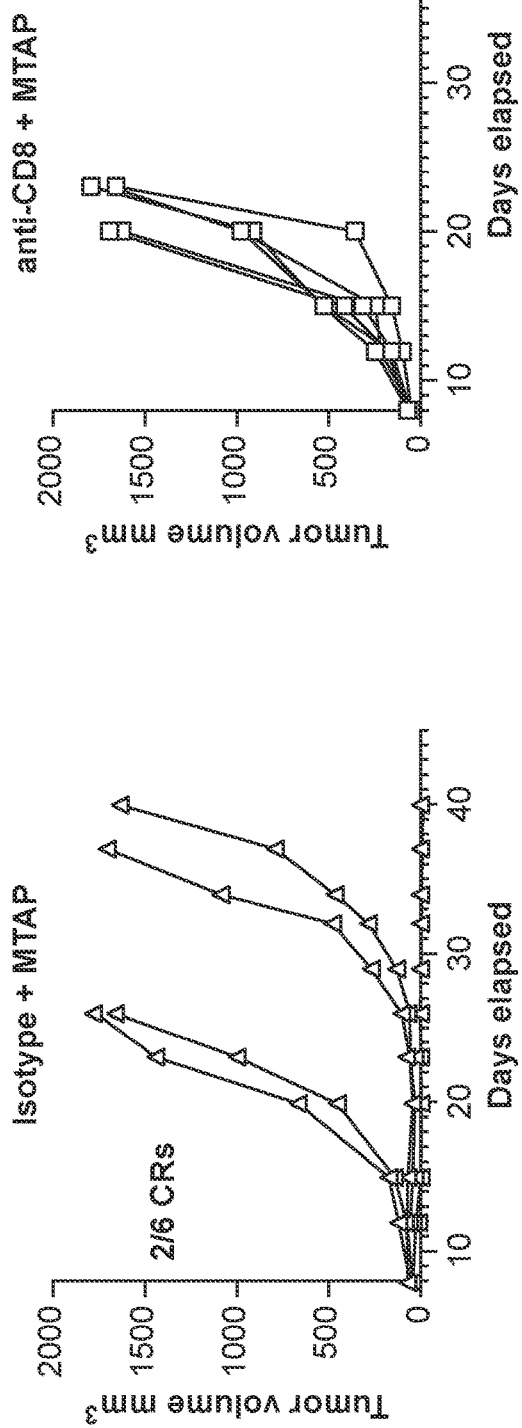
FIG. 6A
FIG. 6B
FIG. 6C
FIG. 6D

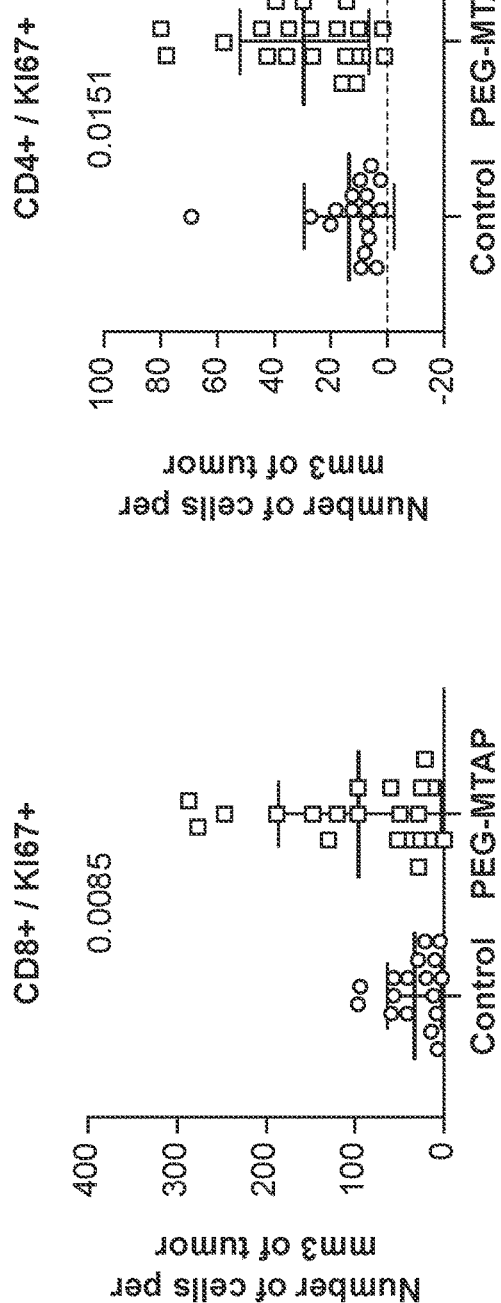
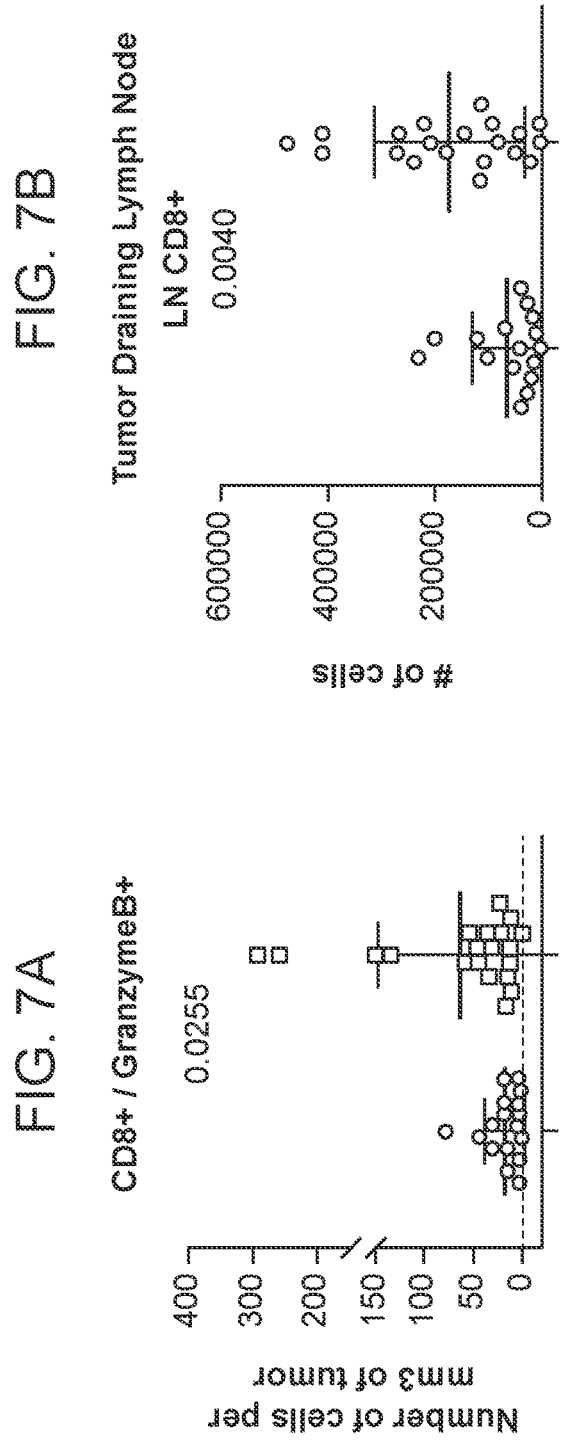

SEQUENCE LISTING

```
<160> NUMBER OF SEQ ID NOS: 35

<210> SEQ ID NO 1
<211> LENGTH: 283
<212> TYPE: PRT
<213> ORGANISM: Homo sapiens

<400> SEQUENCE: 1

Met Ala Ser Gly Thr Thr Thr Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
    50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Thr Met Arg Pro Gln Ser Phe Tyr Asp Gly Ser
        115                 120                 125

His Ser Cys Ala Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
    210                 215                 220

Lys Glu His Glu Glu Ala Val Ser Val Asp Arg Val Leu Lys Thr Leu
```

```
                     225                 230                 235                 240

Lys Glu Asn Ala Asn Lys Ala Lys Ser Leu Leu Leu Thr Thr Ile Pro
                    245                 250                 255

Gln Ile Gly Ser Thr Glu Trp Ser Glu Thr Leu His Asn Leu Lys Asn
                260                 265                 270

Met Ala Gln Phe Ser Val Leu Leu Pro Arg His
                275                 280

<210> SEQ ID NO 2
<211> LENGTH: 851
<212> TYPE: DNA
<213> ORGANISM: Homo sapiens

<400> SEQUENCE: 2
atggcatcgg gaacaaccac gacagccgta aagattggga tcataggggg cacaggactt     60
gatgaccctg aaattttgga aggtcgcact gagaagtacg tagacacccc attcggtaaa    120
cctagcgatg ccctgattct ggcaaaatc aaaaatgtgg attgcgtcct tcttgcccgc     180
cacggacgtc aacataccat catgccatcg aaagtcaatt atcaggcaaa tatatgggca    240
ttgaaggagg agggctgcac ccacgttatt gtgacgacag cttgtggatc gcttcgcgag    300
gagattcaac tggtgacat tgttattata gatcaattca ttgaccgcac gacaatgcgc     360
ccgcaatcgt tctatgacgg ctctcacagt tgtgcgcggg cgtgtgcca catcccaatg     420 gccgagccct tttgcccaaa aacccgcgag gtacttattg agacggcgaa aaaattggga    480
ctgcgttgtc attccaaggg tactatggta actatcgagg ggccgcgttt tagtagccgg    540
ccgaatcgtt catgttccgc acttggggag cggacgtcat taatatgaca actgtcccag    600
aagttgtttt agccaaagag gcgggaatat gctacgcaag cattgctatg gcgactgatt    660
acgactgctg gaaagagcac gaggaagcag tctcagtaga tcgcgtttta aaaacattaa    720
aggagaacgc taataaggcg aaatcccttt tgttgaccac tattcccag attggttcca      780 ctgagtggtc cgaaaccttg cacaacctga gaacatggcc cagttctcc gtactgcttc     840 cgcgccatta a                                                        851

<210> SEQ ID NO 3
<211> LENGTH: 283
<212> TYPE: PRT
<213> ORGANISM: Artificial Sequence
<220> FEATURE:
<223> OTHER INFORMATION: Synthetic polypeptide

<400> SEQUENCE: 3

Met Ala Ser Gly Thr Thr Thr Ala Val Lys Ile Gly Ile Ile Gly
1                   5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
        50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
                100                 105                 110
```

Phe Ile Asp Arg Thr Thr Met Arg Pro Gln Ser Phe Tyr Asp Gly Ser
            115                 120                 125

His Ser Cys Ala Arg Gly Val Cys His Ile Pro Met Ala Glu Pro Phe
        130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
            195                 200                 205

Gly Ile Cys Tyr Ala Ser Ile Ala Met Ala Thr Asp Tyr Asp Cys Trp
210                 215                 220

Arg Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro
                245                 250                 255

Gln Ile Gly Ser Thr Glu Trp Ser Glu Thr Leu His Asn Leu Lys Asn
            260                 265                 270

Met Ala Gln Phe Ser Val Leu Leu Pro Arg His
            275                 280

<210> SEQ ID NO 4
<211> LENGTH: 849
<212> TYPE: DNA
<213> ORGANISM: Artificial Sequence
<220> FEATURE:
<223> OTHER INFORMATION: Synthetic polynucleotide

<400> SEQUENCE: 4
atggcatcgg gaacaaccac gacagccgta aagattggga tcatagggggg cacaggactt    60
gatgaccctg aaattttgga aggtcgcact gagaagtacg tagacacccc attcggtaaa   120
cctagcgatg ccctgattct gggcaaaatc aaaaatgtgg attgcgtcct tcttgcccgc   180
cacggacgtc aacataccat catgccatcg aaagtcaatt atcaggcaaa tatatgggca   240
ttgaaggagg agggctgcac ccacgttatt gtgacgacag cttgtggatc gcttcgcgag   300
gagattcaac tggtgacat tgttattata gatcaattca ttgaccgcac gacaatgcgc   360
ccgcaatcgt tctatgacgg ctctcacagt tgtgcgcggg gcgtgtgcca catcccaatg   420
gccgagccct tttgcccaaa acccgcgag gtacttattg agacggcgaa aaaattggga   480
ctgcgttgtc attccaaggg tactatggta actatcgagg ggccgcgttt tagtagccgt   540
gccgaatcgt tcatgttccg cacttgggga gcggacgtca ttaatatgac aactgtccca   600
gaagttgttt tagccaaaga ggcgggaata tgctacgcaa gcattgctat ggcgactgat   660
tacgactgct ggcgtgagca cgaggaagca gtctcagtag atcgcgtttt aaaaacatta   720
aaggagaacg ctaataaggc gaaatccctt ttgttgacca ctattcccca gattggttcc   780
actgagtggt ccgaaacctt gcacaacctg aagaacatgg cccagttctc cgtactgctt   840
ccgcgccat                                                           849

<210> SEQ ID NO 5
<211> LENGTH: 283
<212> TYPE: PRT
<213> ORGANISM: Artificial Sequence
<220> FEATURE:
<223> OTHER INFORMATION: Synthetic polypeptide

<400> SEQUENCE: 5

```
Met Ala Ser Gly Thr Thr Thr Ala Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
                35                  40                  45

Lys Ile Lys Asn Val Asp Cys Val Leu Leu Ala Arg His Gly Arg Gln
            50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
                100                 105                 110

Phe Ile Asp Arg Thr Thr Met Arg Pro Gln Ser Phe Tyr Asp Gly Ser
            115                 120                 125

His Ser Cys Ala Arg Gly Val Cys His Ile Pro Met Ala Glu Pro Phe
        130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Thr Trp Gly Ala Asp
                180                 185                 190

Val Ile Asn Met Thr Thr Val Pro Glu Val Val Leu Ala Lys Glu Ala
            195                 200                 205

Gly Ile Cys Tyr Ala Ser Ile Ala Met Ala Thr Asp Tyr Asp Cys Trp
        210                 215                 220

Lys Glu His Glu Glu Ala Val Ser Val Asp Arg Val Leu Arg Thr Leu
225                 230                 235                 240

Lys Glu Asn Ala Asn Lys Ala Lys Ser Leu Leu Thr Thr Ile Pro
                245                 250                 255

Gln Ile Gly Ser Thr Glu Trp Ser Glu Thr Leu His Asn Leu Lys Asn
                260                 265                 270

Met Ala Gln Phe Ser Val Leu Leu Pro Arg His
                275                 280
```

<210> SEQ ID NO 6
<211> LENGTH: 849
<212> TYPE: DNA
<213> ORGANISM: Artificial Sequence
<220> FEATURE:
<223> OTHER INFORMATION: Synthetic polynucleotide

<400> SEQUENCE: 6

```
atggcatcgg gaacaaccac gacagccgta aagattggga tcataggggg cacaggactt      60
gatgaccctg aaattttgga aggtcgcact gagaagtacg tagacacccc attcggtaaa     120
cctagcgatg ccctgattct gggcaaaatc aaaaatgtgg attgcgtcct tcttgcccgc     180
cacggacgtc aacataccat catgccatcg aaagtcaatt atcaggcaaa tatatgggca     240
ttgaaggagg agggctgcac ccacgttatt gtgacgacag cttgtggatc gcttcgcgag     300
```

-continued

```
gagattcaac ctggtgacat tgttattata gatcaattca ttgaccgcac gacaatgcgc    360
ccgcaatcgt tctatgacgg ctctcacagt tgtgcgcggg gcgtgtgcca catcccaatg    420
gccgagccct tttgcccaaa aacccgcgag gtacttattg agacggcgaa aaaattggga    480
ctgcgttgtc attccaaggg tactatggta actatcgagg ggccgcgttt tagtagccgt    540
gccgaatcgt tcatgttccg cacttgggga gcggacgtca ttaatatgac aactgtccca    600
gaagttgttt tagccaaaga ggcgggaata tgctacgcaa gcattgctat ggcgactgat    660
tacgactgct ggaaagagca cgaggaagca gtctcagtag atcgcgtttt acgcacatta    720
aaggagaacg ctaataaggc gaaatccctt ttgttgacca ctattcccca gattggttcc    780
actgagtggt ccgaaacctt gcacaacctg aagaacatgg cccagttctc cgtactgctt    840
ccgcgccat                                                            849
```

<210> SEQ ID NO 7
<211> LENGTH: 283
<212> TYPE: PRT
<213> ORGANISM: Macaca mulatta

<400> SEQUENCE: 7

```
Met Ala Ser Gly Thr Thr Thr Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
    50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Thr Val Arg Pro Gln Ser Phe Tyr Asp Gly Ser
        115                 120                 125

His Ser Cys Ala Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
    210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Thr Glu Trp Ser Glu Thr Leu His Asn Leu Lys Asn
            260                 265                 270
```

```
Met Ala Gln Phe Ser Val Leu Leu Pro Arg His
            275                 280
```

<210> SEQ ID NO 8
<211> LENGTH: 283
<212> TYPE: PRT
<213> ORGANISM: Callithrix jacchus

<400> SEQUENCE: 8

```
Met Ala Ser Ser Thr Thr Thr Val Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
                35                  40                  45

Lys Ile Lys Asn Val Asp Cys Val Leu Leu Ala Arg His Gly Arg Gln
            50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
                100                 105                 110

Phe Ile Asp Arg Thr Thr Met Arg Pro Gln Ser Phe Tyr Asp Gly Ser
            115                 120                 125

His Ser Cys Ala Arg Gly Val Cys His Ile Pro Met Ala Glu Pro Phe
        130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Leu Arg Thr Trp Gly Ala Asp
                180                 185                 190

Val Ile Asn Met Thr Thr Val Pro Glu Val Val Leu Ala Lys Glu Ala
            195                 200                 205

Gly Ile Cys Tyr Ala Ser Ile Ala Met Ala Thr Asp Tyr Asp Cys Trp
        210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro
                245                 250                 255

Gln Ile Gly Ser Met Glu Trp Ser Glu Thr Leu His Ser Leu Lys Asn
                260                 265                 270

Met Ala Gln Phe Ser Val Leu Leu Pro Arg His
            275                 280
```

<210> SEQ ID NO 9
<211> LENGTH: 283
<212> TYPE: PRT
<213> ORGANISM: Saimiri boliviensis boliviensis

<400> SEQUENCE: 9

```
Met Ala Ser Ser Thr Thr Thr Val Val Lys Ile Gly Ile Ile Gly
1               5                   10                  15

Gly Thr Gly Leu Asp Asp Pro Glu Ile Leu Glu Gly Arg Thr Glu Lys
                20                  25                  30
```

Tyr Val Asp Thr Pro Phe Gly Lys Pro Ser Asp Ala Leu Ile Leu Gly
    35                  40                  45

Lys Ile Lys Asn Val Asp Cys Val Leu Leu Ala Arg His Gly Arg Gln
 50                  55                  60

His Thr Ile Met Pro Ser Lys Val Asn Tyr Gln Ala Asn Ile Trp Ala
 65                  70                  75                  80

Leu Lys Glu Glu Gly Cys Thr His Val Ile Val Thr Thr Ala Cys Gly
                 85                  90                  95

Ser Leu Arg Glu Glu Ile Gln Pro Gly Asp Ile Val Ile Ile Asp Gln
                100                 105                 110

Phe Ile Asp Arg Thr Thr Val Arg Pro Gln Ser Phe Tyr Asp Gly Ser
            115                 120                 125

His Ser Cys Ala Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
    210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro
                245                 250                 255

Gln Ile Gly Ser Met Glu Trp Ser Glu Thr Leu His Ser Leu Lys Asn
            260                 265                 270

Met Ala Gln Phe Ser Val Leu Leu Pro Arg His
        275                 280

<210> SEQ ID NO 10
<211> LENGTH: 283
<212> TYPE: PRT
<213> ORGANISM: Aotus nancymaae

<400> SEQUENCE: 10

Met Ala Ser Ser Thr Thr Thr Val Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
 50                  55                  60

His Thr Ile Met Pro Ser Lys Val Asn Tyr Gln Ala Asn Ile Trp Ala
 65                  70                  75                  80

Leu Lys Glu Glu Gly Cys Thr His Val Ile Val Thr Thr Ala Cys Gly
                 85                  90                  95

Ser Leu Arg Glu Glu Ile Gln Pro Gly Asp Ile Val Ile Ile Asp Gln
                100                 105                 110

Phe Ile Asp Arg Thr Thr Met Arg Pro Gln Ser Phe Tyr Asp Gly Ser
            115                 120                 125

```
His Ser Cys Ala Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Tyr Met Leu Arg Thr Trp Gly Ala Asp
                180                 185                 190

Val Ile Asn Met Thr Thr Val Pro Glu Val Val Leu Ala Lys Glu Ala
                195                 200                 205

Gly Ile Cys Tyr Ala Ser Ile Ala Met Ala Thr Asp Tyr Asp Cys Trp
        210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Met Glu Trp Ser Glu Thr Leu His Ser Leu Lys Asn
                260                 265                 270

Met Ala Gln Phe Ser Val Leu Leu Pro Arg His
                275                 280

<210> SEQ ID NO 11
<211> LENGTH: 283
<212> TYPE: PRT
<213> ORGANISM: Camelus dromedarius

<400> SEQUENCE: 11

Met Ala Ser Gly Ala Thr Pro Ala Ala Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
                100                 105                 110

Phe Ile Asp Arg Thr Thr Ile Arg Pro Gln Ser Phe Tyr Asp Gly Ser
            115                 120                 125

His Ser Cys Ala Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Ile Thr Ile Glu Gly Pro Arg
                165                 170                 175

Phe Ser Ser Arg Ala Glu Ser Phe Met Phe Arg Thr Trp Gly Ala Asp
                180                 185                 190

Val Ile Asn Met Thr Thr Val Pro Glu Val Val Leu Ala Lys Glu Ala
                195                 200                 205

Gly Met Cys Tyr Ala Ser Ile Ala Met Ala Thr Asp Tyr Asp Cys Trp
```

```
            210                 215                 220
Lys Glu His Glu Glu Ala Val Ser Val Asp Arg Val Leu Lys Thr Leu
225                 230                 235                 240

Lys Glu Asn Ala Asn Lys Ala Lys Ser Leu Leu Ser Thr Ile Pro
                245                 250                 255

Gln Ile Gly Ser Val Glu Trp Ser Glu Thr Leu His Asn Leu Lys Asn
                260                 265                 270

Met Ala Gln Phe Ser Val Leu Leu Pro Arg His
                275                 280

<210> SEQ ID NO 12
<211> LENGTH: 283
<212> TYPE: PRT
<213> ORGANISM: Ochotona princeps

<400> SEQUENCE: 12

Met Ala Ser Gly Ala Ala Thr Thr Ala Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Leu Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Thr Thr Arg Pro Gln Thr Phe Tyr Asp Gly Ser
        115                 120                 125

His Ser Cys Ala Arg Gly Val Cys His Ile Pro Met Val Glu Pro Phe
130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Ile Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
    210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Ala Ile Pro
                245                 250                 255

Gln Ile Gly Ser Thr Glu Trp Ser Glu Thr Leu His Asn Leu Lys Asn
                260                 265                 270

Met Ala Gln Phe Ser Val Leu Leu Pro Arg His
                275                 280

<210> SEQ ID NO 13
<211> LENGTH: 284
```

```
<212> TYPE: PRT
<213> ORGANISM: Oryctolagus cuniculus

<400> SEQUENCE: 13

Met Ala Ser Gly Ala Ala Thr Thr Ala Ala Val Lys Ile Gly Ile Ile
1               5                   10                  15

Gly Gly Thr Gly Leu Asp Asp Pro Glu Ile Leu Glu Gly Arg Thr Glu
            20                  25                  30

Lys Tyr Val Asp Thr Pro Phe Gly Lys Pro Ser Asp Ala Leu Ile Leu
        35                  40                  45

Gly Lys Ile Lys Asn Val Asp Cys Val Leu Leu Ala Arg His Gly Arg
    50                  55                  60

Gln His Thr Ile Met Pro Ser Lys Val Asn Tyr Gln Ala Asn Ile Trp
65                  70                  75                  80

Ala Leu Lys Glu Glu Gly Cys Thr His Val Ile Val Thr Thr Ala Cys
                85                  90                  95

Gly Ser Leu Arg Glu Glu Ile Gln Pro Gly Asp Ile Val Ile Ile Asp
            100                 105                 110

Gln Phe Ile Asp Arg Thr Met Thr Arg Pro Gln Thr Phe Tyr Asp Gly
        115                 120                 125

Ser His Ser Cys Ala Arg Gly Val Cys His Ile Pro Met Ala Glu Pro
    130                 135                 140

Phe Cys Pro Lys Thr Arg Glu Val Leu Ile Glu Thr Ala Lys Lys Leu
145                 150                 155                 160

Gly Leu Arg Cys His Ser Lys Gly Thr Met Val Thr Ile Glu Gly Pro
                165                 170                 175

Arg Phe Ser Ser Arg Ala Glu Ser Phe Met Phe Arg Thr Trp Gly Ala
            180                 185                 190

Asp Val Ile Asn Met Thr Thr Val Pro Glu Val Val Leu Ala Lys Glu
        195                 200                 205

Ala Gly Ile Cys Tyr Ala Ser Ile Ala Met Ala Thr Asp Tyr Asp Cys
    210                 215                 220

Trp Lys Glu His Glu Glu Ala Val Ser Val Asp Arg Val Leu Lys Thr
225                 230                 235                 240

Leu Lys Glu Asn Ala Asn Lys Ala Lys Ser Leu Leu Leu Thr Thr Ile
                245                 250                 255

Pro Gln Ile Gly Ser Thr Glu Trp Ser Glu Thr Leu His Asn Leu Lys
            260                 265                 270

Asn Met Ala Gln Phe Ser Val Leu Leu Pro Arg His
        275                 280

<210> SEQ ID NO 14
<211> LENGTH: 283
<212> TYPE: PRT
<213> ORGANISM: Mustela putorius furo

<400> SEQUENCE: 14

Met Ala Ser Gly Ala Thr Pro Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
    50                  55                  60
```

```
His Thr Ile Met Pro Ser Lys Val Asn Tyr Gln Ala Asn Ile Trp Ala
 65                  70                  75                  80

Leu Lys Glu Glu Gly Cys Thr His Ile Val Thr Thr Ala Cys Gly
             85                  90                  95

Ser Leu Arg Glu Glu Ile Gln Pro Gly Asp Ile Val Ile Ile Asp Gln
             100                 105                 110

Phe Ile Asp Arg Thr Thr Lys Arg Pro Gln Thr Phe Tyr Asp Gly Ser
             115                 120                 125

His Ser Cys Thr Arg Gly Val Cys His Ile Pro Met Ala Glu Pro Phe
             130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
             165                 170                 175

Phe Ser Ser Arg Ala Glu Ser Phe Met Phe Arg Thr Trp Gly Ala Asp
             180                 185                 190

Val Ile Asn Met Thr Thr Val Pro Glu Val Val Leu Ala Lys Glu Ala
             195                 200                 205

Gly Ile Cys Tyr Ala Ser Ile Ala Met Ala Thr Asp Tyr Asp Cys Trp
210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
             245                 250                 255

Gln Ile Gly Ser Met Glu Trp Ser Glu Thr Leu His Asn Leu Lys Asn
             260                 265                 270

Met Ala Gln Phe Ser Val Leu Leu Pro Arg His
             275                 280

<210> SEQ ID NO 15
<211> LENGTH: 283
<212> TYPE: PRT
<213> ORGANISM: Ailuropoda melanoleuca

<400> SEQUENCE: 15

Met Ala Ser Gly Ala Thr Pro Thr Ala Val Lys Ile Gly Ile Ile Gly
 1               5                  10                  15

Gly Thr Gly Leu Asp Asp Pro Glu Ile Leu Glu Gly Arg Thr Glu Lys
             20                  25                  30

Tyr Val Asp Thr Pro Phe Gly Lys Pro Ser Asp Ala Leu Ile Leu Gly
             35                  40                  45

Lys Ile Lys Asn Val Asp Cys Val Leu Leu Ala Arg His Gly Arg Gln
 50                  55                  60

His Thr Ile Met Pro Ser Lys Val Asn Tyr Gln Ala Asn Ile Trp Ala
 65                  70                  75                  80

Leu Lys Glu Glu Gly Cys Thr His Ile Val Thr Thr Ala Cys Gly
             85                  90                  95

Ser Leu Arg Glu Glu Ile Gln Pro Gly Asp Ile Val Ile Ile Asp Gln
             100                 105                 110

Phe Ile Asp Arg Thr Thr Lys Arg Pro Gln Thr Phe Tyr Asp Gly Ser
             115                 120                 125

His Ser Cys Ala Arg Gly Val Cys His Ile Pro Met Ala Glu Pro Phe
             130                 135                 140

Cys Pro Lys Thr Arg Glu Val Leu Thr Glu Thr Ala Lys Lys Leu Gly
145                 150                 155                 160
```

Leu Arg Cys His Ser Lys Gly Thr Met Val Thr Ile Glu Gly Pro Arg
            165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
            195                 200                 205

Gly Ile Cys Tyr Ala Ser Ile Ala Met Ala Thr Asp Tyr Asp Cys Trp
            210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Ala Ile Pro
            245                 250                 255

Gln Ile Gly Ser Met Glu Trp Ser Glu Thr Leu His Asn Leu Lys Asn
            260                 265                 270

Met Ala Gln Phe Ser Val Leu Leu Pro Arg His
            275                 280

<210> SEQ ID NO 16
<211> LENGTH: 283
<212> TYPE: PRT
<213> ORGANISM: Galeopterus variegatus

<400> SEQUENCE: 16

Met Ala Ser Gly Ala Ala Thr Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
            85                  90                  95

Ser Leu Arg Asp Glu Ile Gln Pro Gly Asp Ile Val Ile Ile Asp Gln
            100                 105                 110

Phe Ile Asp Arg Thr Thr Lys Arg Pro Gln Ser Phe Tyr Asp Gly Ser
            115                 120                 125

His Ser Cys Ala Arg Gly Val Cys His Ile Pro Met Ala Glu Pro Phe
            130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
            165                 170                 175

Phe Ser Ser Arg Met Glu Ser Phe Leu Phe Arg Thr Trp Gly Ala Asp
            180                 185                 190

Val Ile Asn Met Thr Thr Val Pro Glu Val Val Leu Ala Lys Glu Ala
            195                 200                 205

Gly Ile Cys Tyr Ala Ser Ile Ala Met Ala Thr Asp Tyr Asp Cys Trp
            210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro

```
                    245                 250                 255
Gln Ile Gly Ser Met Glu Trp Ser Glu Thr Leu His Asn Leu Lys Asn
                260                 265                 270
Met Ala Gln Phe Ser Ile Leu Val Pro Arg His
                275                 280

<210> SEQ ID NO 17
<211> LENGTH: 344
<212> TYPE: PRT
<213> ORGANISM: Camelus ferus

<400> SEQUENCE: 17

Met Pro Gln Ala Thr Pro Met Glu Pro Gly Ser Gln Gln Ala Pro Ala
1               5                   10                  15
Asn Ser Asp Phe Gln Leu Thr Met Lys Phe Asn Glu Ser Arg Ala Ala
                20                  25                  30
Arg Val Asn Pro Leu Arg Ala Ser Ser Pro Arg Val Ala Ala Pro
            35                  40                  45
Ser Gln Arg Arg His Gly Leu Arg Cys His Ser Arg Gly Arg Asp Ser
        50                  55                  60
Gly Ala Thr Pro Ala Ala Val Lys Ile Gly Ile Ile Gly Gly Thr Gly
65                  70                  75                  80
Leu Asp Asp Pro Glu Ile Leu Glu Gly Arg Thr Glu Lys Tyr Val Asp
                85                  90                  95
Thr Pro Phe Gly Lys Pro Ser Asp Ala Leu Ile Leu Gly Lys Ile Lys
                100                 105                 110
Asn Val Asp Cys Val Leu Leu Ala Arg His Gly Arg Gln His Thr Ile
            115                 120                 125
Met Pro Ser Lys Val Asn Tyr Gln Ala Asn Ile Trp Ala Leu Lys Glu
        130                 135                 140
Glu Gly Cys Thr His Val Ile Val Thr Thr Ala Cys Gly Ser Leu Arg
145                 150                 155                 160
Glu Glu Ile Gln Pro Gly Asp Ile Val Ile Asp Gln Phe Ile Asp
                165                 170                 175
Arg Thr Thr Ile Arg Pro Gln Ser Phe Tyr Asp Gly Ser His Ser Cys
                180                 185                 190
Ala Arg Gly Val Cys His Ile Pro Met Ala Glu Pro Phe Cys Pro Lys
            195                 200                 205
Thr Arg Glu Val Leu Ile Glu Thr Ala Lys Lys Leu Gly Leu Arg Cys
        210                 215                 220
His Ser Lys Gly Thr Met Val Thr Ile Lys Gly Pro Arg Phe Ser Ser
225                 230                 235                 240
Arg Ala Glu Ser Phe Met Phe Arg Thr Trp Gly Ala Asp Val Ile Asn
                245                 250                 255
Met Thr Thr Val Pro Glu Val Val Leu Ala Lys Glu Ala Gly Met Cys
                260                 265                 270
Tyr Ala Ser Ile Ala Met Ala Thr Asp Tyr Asp Cys Trp Lys Glu His
            275                 280                 285
Glu Glu Ala Val Ser Val Asp Arg Val Leu Lys Thr Leu Lys Glu Asn
        290                 295                 300
Ala Asn Lys Ala Lys Ser Leu Leu Leu Ser Thr Ile Pro Gln Ile Gly
305                 310                 315                 320
Ser Val Glu Trp Ser Gly Thr Leu His Asn Leu Lys Asn Met Ala Gln
                325                 330                 335
```

```
Phe Ser Val Leu Leu Pro Arg His
            340
```

<210> SEQ ID NO 18
<211> LENGTH: 283
<212> TYPE: PRT
<213> ORGANISM: Hipposideros armiger

<400> SEQUENCE: 18

```
Met Ala Ser Cys Ala Thr Pro Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
    50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Thr Thr Arg Pro Gln Thr Phe Tyr Asp Gly Ser
        115                 120                 125

His Ser Cys Ala Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Leu Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Ile Pro Glu Val Val Leu Ala Lys Glu Ala
        195                 200                 205

Gly Leu Cys Tyr Ala Ser Ile Ala Met Ala Thr Asp Tyr Asp Cys Trp
    210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro
                245                 250                 255

Gln Val Gly Ser Met Glu Trp Ser Glu Thr Leu His Asn Leu Lys Asn
            260                 265                 270

Met Ala Gln Phe Ser Val Leu Leu Pro Arg His
        275                 280
```

<210> SEQ ID NO 19
<211> LENGTH: 283
<212> TYPE: PRT
<213> ORGANISM: Felis catus

<400> SEQUENCE: 19

```
Met Ala Ser Gly Ala Thr Pro Ala Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30
```

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
 50                  55                  60

His Ser Ile Met Pro Ser Lys Val Asn Tyr Gln Ala Asn Ile Trp Ala
 65                  70                  75                  80

Leu Lys Glu Glu Gly Cys Thr His Val Ile Val Thr Ala Cys Gly
                85                  90                  95

Ser Leu Arg Glu Glu Ile Gln Pro Gly Asp Ile Val Ile Ile Asp Gln
                100                 105                 110

Phe Ile Asp Arg Thr Thr Ile Arg Pro Gln Thr Phe Tyr Asp Gly Ser
            115                 120                 125

His Ser Cys Ala Arg Gly Val Cys His Ile Pro Met Ala Glu Pro Phe
130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Met Glu Trp Ser Glu Thr Leu Gln Asn Leu Lys Asn
            260                 265                 270

Thr Ala Gln Phe Ser Val Leu Leu Pro Arg His
            275                 280

<210> SEQ ID NO 20
<211> LENGTH: 283
<212> TYPE: PRT
<213> ORGANISM: Odobenus rosmarus divergens

<400> SEQUENCE: 20

Met Ala Ser Gly Ala Ile Pro Thr Ala Val Lys Ile Gly Ile Ile Gly
 1               5                  10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
 50                  55                  60

His Thr Ile Met Pro Ser Lys Val Asn Tyr Gln Ala Asn Ile Trp Ala
 65                  70                  75                  80

Leu Lys Glu Glu Gly Cys Thr His Val Ile Val Thr Ala Cys Gly
                85                  90                  95

Ser Leu Arg Glu Glu Ile Gln Pro Gly Asp Ile Val Ile Ile Asp Gln
                100                 105                 110

Phe Ile Asp Arg Thr Thr Lys Arg Pro Gln Thr Phe Tyr Asp Gly Ser
            115                 120                 125

```
His Ser Ser Thr Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Thr Trp Gly Ala Asp
                180                 185                 190

Val Ile Asn Met Thr Thr Val Pro Glu Val Val Leu Ala Lys Glu Ala
                195                 200                 205

Gly Ile Cys Tyr Ala Ser Ile Ala Met Ala Thr Asp Tyr Asp Cys Trp
            210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Met Glu Trp Ser Glu Thr Leu His Asn Leu Lys Asn
                260                 265                 270

Met Ala Gln Phe Ser Val Leu Leu Pro Arg His
                275                 280

<210> SEQ ID NO 21
<211> LENGTH: 283
<212> TYPE: PRT
<213> ORGANISM: Ictidomys tridecemlineatus

<400> SEQUENCE: 21

Met Ala Ser Gly Ala Ala Thr Thr Ala Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Val Ile Asp Gln
                100                 105                 110

Phe Ile Asp Arg Thr Thr Met Arg Pro Gln Thr Phe Tyr Asp Gly Cys
            115                 120                 125

His Ser Cys Thr Arg Gly Val Cys His Ile Pro Leu Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Ile Val Thr Ile Glu Gly Pro Arg
                165                 170                 175

Phe Ser Ser Arg Ala Glu Ser Phe Met Phe Arg Thr Trp Gly Ala Asp
                180                 185                 190

Val Ile Asn Met Thr Thr Val Pro Glu Val Val Leu Ala Lys Glu Ala
                195                 200                 205

Gly Ile Cys Tyr Ala Gly Ile Ala Met Ala Thr Asp Tyr Asp Cys Trp
```

```
                210                 215                 220
Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Ala Ile Pro
            245                 250                 255

Gln Ile Gly Ser Met Glu Trp Ser Glu Thr Leu His Asn Leu Lys Asn
            260                 265                 270

Met Ala Gln Phe Ser Val Leu Leu Pro Arg His
            275                 280

<210> SEQ ID NO 22
<211> LENGTH: 283
<212> TYPE: PRT
<213> ORGANISM: Leptonychotes weddellii

<400> SEQUENCE: 22

Met Ala Ser Gly Ala Thr Pro Thr Ala Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
50                  55                  60

His Thr Ile Met Pro Ser Lys Val Asn Tyr Gln Ala Asn Ile Trp Ala
65                  70                  75                  80

Leu Lys Glu Glu Gly Cys Thr His Ile Ile Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Thr Lys Arg Pro Gln Thr Phe Tyr Asp Gly Ser
            115                 120                 125

His Ser Ser Thr Arg Gly Val Cys His Ile Pro Val Ala Glu Pro Phe
            130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Val Val Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
            195                 200                 205

Gly Ile Cys Tyr Ala Ser Ile Ala Met Ala Thr Asp Tyr Asp Cys Trp
        210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
            245                 250                 255

Gln Ile Gly Ser Met Glu Trp Ser Glu Thr Leu His Asn Leu Lys Asn
            260                 265                 270

Met Ala Gln Phe Ser Val Leu Leu Pro Arg His
            275                 280

<210> SEQ ID NO 23
<211> LENGTH: 283
```

```
<212> TYPE: PRT
<213> ORGANISM: Rhinolophus sinicus

<400> SEQUENCE: 23

Met Ala Ser Gly Ala Thr Pro Thr Ala Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
        50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
                100                 105                 110

Phe Ile Asp Arg Thr Thr Thr Arg Pro Gln Thr Phe Tyr Asp Gly Ser
            115                 120                 125

Arg Ser Cys Ser Arg Gly Val Cys His Ile Pro Met Ala Glu Pro Phe
        130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Leu Thr Ile Glu Gly Pro Arg
                165                 170                 175

Phe Ser Ser Arg Ser Glu Ser Ile Met Phe Arg Thr Trp Gly Ala Asp
            180                 185                 190

Val Ile Asn Met Thr Thr Ile Pro Glu Val Val Leu Ala Lys Glu Ala
                195                 200                 205

Gly Leu Cys Tyr Ala Ser Ile Ala Met Ala Thr Asp Tyr Asp Cys Trp
        210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Met Glu Trp Ser Glu Thr Leu His Asn Leu Lys Asn
                260                 265                 270

Met Ala Gln Phe Ser Val Leu Leu Pro Arg His
                275                 280

<210> SEQ ID NO 24
<211> LENGTH: 283
<212> TYPE: PRT
<213> ORGANISM: Castor canadensis

<400> SEQUENCE: 24

Met Ala Leu Ser Ala Ala Gly Thr Ala Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
        50                  55                  60
```

```
His Thr Ile Met Pro Ser Lys Val Asn Tyr Gln Ala Asn Ile Trp Ala
 65                  70                  75                  80

Leu Lys Glu Glu Gly Cys Thr His Val Ile Val Thr Thr Ala Cys Gly
                 85                  90                  95

Ser Leu Arg Glu Glu Ile Gln Pro Gly Asp Ile Val Ile Ile Asp Gln
                100                 105                 110

Phe Ile Asp Arg Thr Ser Ile Arg Pro Gln Thr Phe Tyr Asp Gly Ser
            115                 120                 125

His Ser Cys Ser Arg Gly Val Cys His Ile Pro Met Ala Glu Pro Phe
130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Val Val Thr Ile Glu Gly Pro Arg
                165                 170                 175

Phe Ser Ser Arg Ala Glu Ser Phe Met Phe Arg Thr Trp Gly Ala Asp
            180                 185                 190

Ile Ile Asn Met Thr Thr Val Pro Glu Val Ile Leu Ala Lys Glu Ala
            195                 200                 205

Gly Ile Cys Tyr Ala Ser Ile Ala Met Ala Thr Asp Tyr Asp Cys Trp
210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Met Glu Trp Ser Glu Thr Leu His Asn Leu Lys Asn
            260                 265                 270

Met Ala Gln Phe Ser Val Leu Leu Pro Arg His
            275                 280

<210> SEQ ID NO 25
<211> LENGTH: 283
<212> TYPE: PRT
<213> ORGANISM: Chrysochloris asiatica

<400> SEQUENCE: 25

Met Ala Ser Gly Ala Ala Thr Thr Ala Val Lys Ile Gly Ile Ile Gly
  1               5                  10                  15

Gly Thr Gly Leu Asp Asp Pro Asp Ile Leu Glu Gly Arg Thr Glu Lys
                 20                  25                  30

Tyr Val Asp Thr Pro Phe Gly Lys Pro Ser Asp Ala Leu Ile Leu Gly
             35                  40                  45

Lys Ile Lys Asn Val Asp Cys Val Leu Leu Ala Arg His Gly Arg Gln
 50                  55                  60

His Thr Ile Met Pro Ser Lys Val Asn Tyr Gln Ala Asn Ile Trp Ala
 65                  70                  75                  80

Leu Lys Glu Gln Gly Cys Thr His Ile Ile Val Thr Thr Ala Cys Gly
                 85                  90                  95

Ser Leu Arg Glu Glu Ile Gln Pro Gly Asp Ile Ile Leu Ile Asp Gln
                100                 105                 110

Phe Ile Asp Arg Thr Ser Ile Arg Pro Gln Thr Phe Tyr Asp Gly Ser
            115                 120                 125

Arg Ser Cys Ala Arg Gly Val Cys His Ile Pro Met Ala Glu Pro Phe
130                 135                 140

Cys Pro Lys Thr Arg Glu Val Leu Ile Glu Thr Ala Lys Lys Leu Gly
145                 150                 155                 160
```

```
Leu Arg Cys His Ser Lys Gly Thr Met Ile Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
    210                 215                 220

Lys Glu His Glu Glu Ala Val Ser Val Asp Lys Val Leu Lys Asn Leu
225                 230                 235                 240

Lys Glu Asn Ala Asn Lys Ala Lys Ser Leu Leu Leu Thr Thr Ile Pro
                245                 250                 255

Gln Ile Gly Ser Met Glu Trp Ser Glu Thr Leu His Asn Leu Lys Asn
            260                 265                 270

Met Ala Gln Phe Ser Val Leu Val Pro Arg His
        275                 280

<210> SEQ ID NO 26
<211> LENGTH: 283
<212> TYPE: PRT
<213> ORGANISM: Myotis lucifugus

<400> SEQUENCE: 26

Met Ala Ser Gly Ala Thr Leu Pro Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
    50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Thr Met Arg Pro Gln Thr Phe Tyr Asp Gly Ser
        115                 120                 125

His Ser Cys Ala Arg Gly Val Cys His Ile Pro Met Ala Glu Pro Phe
    130                 135                 140

Cys Pro Lys Thr Arg Glu Val Leu Thr Glu Thr Ala Lys Lys Leu Gly
145                 150                 155                 160

Leu Arg Tyr His Ser Lys Gly Thr Met Leu Thr Ile Glu Gly Pro Arg
                165                 170                 175

Phe Ser Ser Arg Ala Glu Ser Ile Met Phe Arg Thr Trp Gly Ala Asp
            180                 185                 190

Val Ile Asn Met Thr Thr Val Pro Glu Val Val Leu Ala Lys Glu Ala
        195                 200                 205

Gly Leu Cys Tyr Ala Ser Ile Ala Met Ala Thr Asp Tyr Asp Cys Trp
    210                 215                 220

Lys Glu His Glu Glu Val Val Ser Val Asp Arg Val Leu Lys Thr Leu
225                 230                 235                 240

Lys Glu Asn Ala Asn Lys Ala Lys Ser Leu Leu Leu Thr Thr Ile Pro
```

```
                        245                 250                 255
Gln Ile Gly Ser Met Glu Trp Ser Glu Thr Leu His Asn Leu Lys Asn
                260                 265                 270
Met Ala Gln Phe Ser Val Leu Leu Pro Arg His
            275                 280
```

<210> SEQ ID NO 27
<211> LENGTH: 283
<212> TYPE: PRT
<213> ORGANISM: Pteropus alecto

<400> SEQUENCE: 27

```
Met Val Pro Gly Ala Ser Pro Thr Ala Val Lys Ile Gly Ile Ile Gly
1               5                   10                  15
Gly Thr Gly Leu Asp Asp Pro Glu Ile Leu Glu Gly Arg Thr Glu Lys
                20                  25                  30
Tyr Val Asp Thr Pro Phe Gly Lys Pro Ser Asp Ala Leu Ile Leu Gly
            35                  40                  45
Lys Ile Lys Asn Val Asp Cys Val Leu Leu Ala Arg His Gly Arg Gln
50                  55                  60
His Thr Ile Met Pro Ser Lys Val Asn Tyr Gln Ala Asn Ile Trp Ala
65                  70                  75                  80
Leu Lys Glu Glu Gly Cys Thr His Val Ile Val Thr Thr Ala Cys Gly
                85                  90                  95
Ser Leu Arg Glu Glu Ile Gln Pro Gly Asp Ile Val Ile Ile Asp Gln
                100                 105                 110
Phe Ile Asp Arg Thr Thr Thr Arg Pro Gln Thr Phe Tyr Asp Gly Ser
            115                 120                 125
His Pro Cys Ala Arg Gly Val Cys His Ile Pro Met Ala Glu Pro Phe
130                 135                 140
Cys Pro Lys Thr Arg Glu Val Leu Ile Glu Thr Ala Lys Lys Leu Gly
145                 150                 155                 160
Leu Arg Cys His Ser Lys Gly Thr Met Leu Thr Ile Glu Gly Pro Arg
                165                 170                 175
Phe Ser Ser Arg Ala Glu Ser Phe Met Phe Arg Gly Trp Gly Ala Asp
            180                 185                 190
Val Ile Asn Met Thr Thr Val Pro Glu Val Val Leu Ala Lys Glu Ala
        195                 200                 205
Gly Leu Cys Tyr Ala Ser Ile Ala Met Ala Thr Asp Tyr Asp Cys Trp
    210                 215                 220
Lys Glu His Glu Glu Ala Val Ser Val Asp Arg Val Leu Lys Thr Leu
225                 230                 235                 240
Lys Glu Asn Ala Asn Lys Ala Lys Ser Leu Leu Leu Thr Thr Ile Pro
                245                 250                 255
Gln Ile Gly Ser Met Glu Trp Ser Glu Thr Leu His Asn Leu Lys Asn
                260                 265                 270
Met Ala Gln Phe Ser Val Leu Leu Pro Arg His
            275                 280
```

<210> SEQ ID NO 28
<211> LENGTH: 283
<212> TYPE: PRT
<213> ORGANISM: Tupaia chinensis

<400> SEQUENCE: 28

Met Ala Ser Gly Ala Ala Asn Asn Ala Val Lys Ile Gly Ile Ile Gly

```
  1               5                  10                 15
Gly Thr Gly Leu Asp Asp Pro Glu Ile Leu Glu Gly Arg Thr Glu Lys
            20                 25                 30

Tyr Val Asp Thr Pro Phe Gly Lys Pro Ser Asp Ala Leu Ile Leu Gly
            35                 40                 45

Lys Ile Lys Asn Val Asp Cys Val Leu Leu Ala Arg His Gly Arg Gln
 50                 55                 60

His Thr Ile Met Pro Ser Lys Val Asn Tyr Gln Ala Asn Ile Trp Ala
 65                 70                 75                 80

Leu Lys Glu Glu Gly Cys Thr His Val Ile Val Thr Thr Ala Cys Gly
                85                 90                 95

Ser Leu Arg Glu Glu Ile Gln Pro Gly Asp Ile Val Ile Ile Asp Gln
                100                105                110

Phe Ile Asp Arg Thr Thr Ile Arg Pro Gln Thr Phe Tyr Asp Gly Ser
            115                120                125

His Pro Cys Ala Arg Gly Val Cys His Ile Pro Val Ala Glu Pro Phe
        130                135                140

Cys Pro Lys Thr Arg Glu Val Leu Ile Glu Thr Ala Lys Lys Leu Gly
145                150                155                160

Leu Arg Cys His Ser Lys Gly Thr Met Val Thr Ile Glu Gly Pro Arg
                165                170                175

Phe Ser Arg Ala Glu Ser Phe Met Phe Arg Thr Trp Gly Ala Asp
            180                185                190

Val Ile Asn Met Thr Thr Val Pro Glu Val Val Leu Ala Lys Glu Ala
            195                200                205

Gly Ile Cys Tyr Ala Ser Ile Ala Met Ala Thr Asp Tyr Asp Cys Trp
        210                215                220

Lys Glu His Glu Glu Ala Val Ser Val Asp Arg Val Leu Lys Thr Leu
225                230                235                240

Lys Glu Asn Ala Asn Lys Ala Lys Ser Leu Leu Thr Thr Ile Pro
                245                250                255

Leu Ile Gly Ser Met Glu Trp Ser Glu Thr Leu His Asn Leu Lys Asn
                260                265                270

Thr Ala Gln Phe Ser Val Leu Leu Pro Arg His
                275                280

<210> SEQ ID NO 29
<211> LENGTH: 283
<212> TYPE: PRT
<213> ORGANISM: Loxodonta africana

<400> SEQUENCE: 29

Met Ala Ser Ser Ala Ala Thr Thr Thr Val Lys Ile Gly Ile Ile Gly
1               5                  10                 15

Gly Thr Gly Leu Asp Asp Pro Glu Ile Leu Glu Gly Arg Thr Glu Lys
            20                 25                 30

Tyr Val Asp Thr Pro Phe Gly Lys Pro Ser Asp Ala Leu Ile Leu Gly
            35                 40                 45

Lys Ile Lys Asn Val Asp Cys Val Leu Leu Ala Arg His Gly Arg Gln
 50                 55                 60

His Thr Ile Met Pro Ser Lys Val Asn Tyr Gln Ala Asn Ile Trp Ala
 65                 70                 75                 80

Leu Lys Glu Glu Gly Cys Thr His Val Ile Val Thr Thr Ala Cys Gly
                85                 90                 95
```

```
Ser Leu Arg Glu Glu Val Gln Pro Gly Asp Ile Val Ile Asp Gln
            100                 105                 110

Phe Ile Asp Arg Thr Thr Thr Arg Pro Gln Thr Phe Tyr Asp Gly Ser
            115                 120                 125

Arg Ser Cys Ala Arg Gly Val Cys His Ile Pro Met Ala Glu Pro Phe
130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Ile Thr Ile Glu Gly Pro Arg
                165                 170                 175

Phe Ser Ser Arg Ala Glu Ser Leu Met Phe Arg Thr Trp Gly Ala Asp
                180                 185                 190

Val Ile Asn Met Thr Thr Val Pro Glu Val Val Leu Ala Lys Glu Ala
                195                 200                 205

Gly Ile Cys Tyr Ala Ser Ile Ala Met Ala Thr Asp Tyr Asp Cys Trp
                210                 215                 220

Lys Glu His Glu Glu Ala Val Ser Val Asp Arg Val Leu Lys Thr Leu
225                 230                 235                 240

Lys Glu Asn Ala Asn Lys Ala Thr Ser Val Leu Leu Thr Thr Ile Pro
                245                 250                 255

Gln Ile Gly Ser Met Glu Trp Ser Glu Thr Leu His Asn Leu Lys Asn
                260                 265                 270

Met Ala Gln Phe Ser Val Leu Leu Pro Arg His
                275                 280

<210> SEQ ID NO 30
<211> LENGTH: 283
<212> TYPE: PRT
<213> ORGANISM: Erinaceus europaeus

<400> SEQUENCE: 30

Met Ala Ser Gly Ala Ala Thr Pro Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
50                  55                  60

His Thr Ile Met Pro Ser Arg Val Asn Tyr Gln Ala Asn Ile Trp Ala
65                  70                  75                  80

Leu Lys Glu Glu Gly Cys Thr His Ile Ile Val Thr Thr Ala Cys Gly
                85                  90                  95

Ser Leu Arg Glu Glu Ile Gln Pro Gly Asp Ile Val Ile Asp Gln
            100                 105                 110

Phe Ile Asp Arg Thr Thr Lys Arg Ala Gln Thr Phe Tyr Asp Gly Ser
            115                 120                 125

His Ser Cys Ala Arg Gly Val Cys His Ile Pro Val Ala Glu Pro Phe
130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Thr Trp Gly Ala Asp
                180                 185                 190
```

```
Val Ile Asn Met Thr Thr Val Pro Glu Val Val Leu Ala Lys Glu Ala
            195                 200                 205

Gly Ile Cys Tyr Ala Ser Ile Ala Met Ala Thr Asp Tyr Asp Cys Trp
            210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro
            245                 250                 255

Gln Ile Gly Ser Met Glu Trp Ser Gly Thr Leu His Asn Leu Lys Asn
            260                 265                 270

Met Ala His Phe Ser Val Leu Leu Pro Arg His
            275                 280

<210> SEQ ID NO 31
<211> LENGTH: 280
<212> TYPE: PRT
<213> ORGANISM: Mandrillus leucophaeus

<400> SEQUENCE: 31

Met Ala Ser Gly Thr Thr Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
            85                  90                  95

Ser Leu Arg Glu Glu Ile Gln Pro Gly Asp Ile Val Ile Ile Asp Gln
            100                 105                 110

Phe Ile Asp Arg Thr Thr Met Arg Pro Gln Ser Phe Tyr Asp Gly Ser
            115                 120                 125

His Ser Cys Ala Arg Gly Val Cys His Ile Pro Met Ala Glu Pro Phe
            130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
            165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
            195                 200                 205

Gly Ile Cys Tyr Ala Ser Ile Ala Met Ala Thr Asp Tyr Asp Cys Trp
            210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro
            245                 250                 255

Gln Ile Gly Ser Thr Glu Trp Ser Glu Thr Leu His Asn Leu Lys Val
            260                 265                 270

Arg Ser Ala Phe Tyr Leu Leu Pro
```

275                 280

<210> SEQ ID NO 32
<211> LENGTH: 283
<212> TYPE: PRT
<213> ORGANISM: Eptesicus fuscus

<400> SEQUENCE: 32

Met Ala Ser Gly Ala Thr Pro Thr Ala Val Lys Ile Gly Ile Val Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
    50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Ala Met Arg Pro Gln Thr Phe Tyr Asp Gly Asn
        115                 120                 125

His Ser Cys Ala Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Tyr His Ser Lys Gly Thr Val Leu Thr Ile Glu Gly Pro Arg
                165                 170                 175

Phe Ser Ser Arg Ala Glu Ser Ile Met Phe Arg Thr Trp Gly Ala Asp
            180                 185                 190

Val Ile Asn Met Thr Thr Val Pro Glu Val Val Leu Ala Lys Glu Ala
        195                 200                 205

Gly Leu Cys Tyr Ala Ser Ile Ala Met Ala Thr Asp Tyr Asp Cys Trp
    210                 215                 220

Lys Glu His Glu Glu Val Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Met Glu Trp Ser Glu Thr Leu His Asn Leu Lys Asn
            260                 265                 270

Met Ala Gln Phe Ser Val Leu Leu Pro Arg His
        275                 280

<210> SEQ ID NO 33
<211> LENGTH: 334
<212> TYPE: PRT
<213> ORGANISM: Pan troglodytes

<400> SEQUENCE: 33

Met Ala Ser Gly Thr Thr Thr Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly

```
            35                  40                  45
Lys Ile Lys Asn Val Asp Cys Val Leu Leu Ala Arg His Gly Arg Gln
             50                  55                  60

His Thr Ile Met Pro Ser Lys Val Asn Tyr Gln Ala Asn Ile Trp Ala
 65                  70                  75                  80

Leu Lys Glu Glu Gly Cys Thr His Val Ile Val Thr Thr Ala Cys Gly
                 85                  90                  95

Ser Leu Arg Glu Glu Ile Gln Pro Gly Asp Ile Val Ile Ile Asp Gln
            100                 105                 110

Phe Ile Asp Arg Thr Thr Met Arg Pro Gln Ser Phe Tyr Asp Gly Ser
            115                 120                 125

His Ser Cys Ala Arg Gly Val Cys His Ile Pro Met Ala Glu Pro Phe
            130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Leu Ala Lys Glu Ala
            195                 200                 205

Gly Ile Cys Tyr Ala Ser Ile Ala Met Ala Thr Asp Tyr Asp Cys Trp
            210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro
                245                 250                 255

Gln Ile Gly Ser Thr Glu Trp Ser Glu Thr Leu His Asn Leu Lys Met
            260                 265                 270

Ile Lys Phe Gln Met Ile Leu Ser Glu Gly Tyr His Pro Phe Asn Ile
            275                 280                 285

Gln Glu Ser Pro Phe Tyr Arg Gly Leu Leu Asp Phe Pro Ser Val Gly
            290                 295                 300

His Gly Arg Gly Glu Ile Leu Pro Leu Ser Pro Leu Asp Leu Ala Gly
305                 310                 315                 320

Tyr Cys Phe Gln Gln Pro Met Gln Pro Pro Cys Pro Asp Ser
            325                 330

<210> SEQ ID NO 34
<211> LENGTH: 280
<212> TYPE: PRT
<213> ORGANISM: Nomascus leucogenys

<400> SEQUENCE: 34

Met Ala Ser Gly Thr Thr Thr Thr Ala Val Lys Ile Gly Ile Gly
 1               5                  10                  15

Gly Thr Gly Leu Asp Asp Pro Glu Ile Leu Glu Gly Arg Thr Glu Lys
             20                  25                  30

Tyr Val Asp Thr Pro Phe Gly Lys Pro Ser Asp Ala Leu Ile Leu Gly
             35                  40                  45

Lys Ile Lys Asn Val Asp Cys Val Leu Leu Ala Arg His Gly Arg Gln
             50                  55                  60

His Thr Ile Met Pro Ser Lys Val Asn Tyr Gln Ala Asn Ile Trp Ala
 65                  70                  75                  80
```

```
Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Thr Met Arg Pro Gln Ser Phe Tyr Asp Gly Ser
            115                 120                 125

His Ser Cys Ala Arg Gly Val Cys His Ile Pro Met Ala Glu Pro Phe
        130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
            195                 200                 205

Gly Ile Cys Tyr Ala Ser Ile Ala Met Ala Thr Asp Tyr Asp Cys Trp
        210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Thr Glu Trp Ser Glu Thr Leu His Asn Leu Lys Val
            260                 265                 270

Arg Ser Ala Val Gln Leu Pro Pro
        275                 280

<210> SEQ ID NO 35
<211> LENGTH: 283
<212> TYPE: PRT
<213> ORGANISM: Trichechus manatus latirostris

<400> SEQUENCE: 35

Met Ala Ser Gly Ala Thr Thr Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Ile Ile Ile Asp Gln
            100                 105                 110

Phe Ile Asp Arg Thr Thr Val Arg Pro Gln Thr Phe Tyr Asp Gly Ser
            115                 120                 125

Cys Ser Ser Ala Arg Gly Val Gly His Ile Pro Met Ala Glu Pro Phe
        130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Val Ile Thr Ile Glu Gly Pro Arg
                165                 170                 175
```

```
Phe Ser Ser Arg Ala Glu Ser Leu Met Phe Arg Thr Trp Gly Ala Asp
            180                 185                 190

Val Ile Asn Met Thr Thr Val Pro Glu Val Val Leu Ala Lys Glu Ala
            195             200             205

Gly Val Cys Tyr Ala Ser Ile Ala Met Ala Thr Asp Tyr Asp Cys Trp
        210             215             220

Lys Glu His Glu Glu Ala Val Ser Val Asp Lys Val Leu Lys Thr Leu
225             230             235             240

Lys Glu Asn Ala Asn Lys Ala Lys Ser Leu Leu Leu Thr Thr Ile Pro
                245             250             255

Gln Ile Gly Ser Met Glu Trp Ser Glu Thr Leu His Asn Leu Lys Asn
            260             265             270

Met Ala Gln Phe Ser Val Leu Leu Pro Arg His
            275             280
```

HUMAN METHYLTHIOADENOSINE/ADENOSINE DEPLETING ENZYME VARIANTS FOR CANCER THERAPY

CROSS REFERENCE

This application is a national phase application under 35 U.S.C. § 371 of International Application No. PCT/US2021/012291, filed Jan. 6, 2021, which claims the priority benefit of U.S. provisional application No. 62/958,161, filed Jan. 7, 2020, each of which is hereby incorporated by reference in its entirety

STATEMENT REGARDING FEDERALLY SPONSORED RESEARCH

This invention was made with government support under Grant No. R01 CA189623 and R01 CA240700 awarded by the National Institutes of Health. The government has certain rights in the invention.

SEQUENCE LISTING

The instant application contains a Sequence Listing which has been submitted electronically in ASCII format and is hereby incorporated by reference in its entirety. The ASCII copy, created on Jan. 6, 2021, is named UTFBP1227WO_ST25 and is 84722 bytes in size.

BACKGROUND OF THE INVENTION

Field

The present invention relates generally to the fields of medicine and biology. More particularly, it concerns enzymes that deplete methylthioadenosine (MTA) and/or adenosine (ADO) for the treatment of cancer. Even more particularly, it concerns the engineering, pharmacological optimization, and process development of human enzymes with MTA and/or ADO degrading activity suitable for human therapy.

Description of Related Art

Homozygous genetic deletion at chromosome 9p21.3 of methylthioadenosine phosphorylase (MTAP) is a common event observed in ~30-40% of osteosarcomas, pancreatic cancers, and chordomas, with even higher losses (60-75%) noted in mesothelioma, T-cell acute lymphoblastic leukemias, and gliomas (Bertino et al., 2011). MTAP catabolizes methylthioadenosine (MTA), a byproduct of polyamine synthesis, into methylthioribose-1'-phosphate (MTR-1'-P) and adenine, which are recycled into the methionine and purine salvage pathways. MTAP loss is correlated with aggressive disease and worse outcomes. MTAP deletion in solid tumors and lymphomas results in an accumulation and increased secretion of its substrate—MTA (Stevens et al., 2008; Stevens et al., 2009; Stevens et al., 2010). A study in melanoma cells reported that significantly higher MTA concentrations in tumors versus in normal tissue correlated with more pronounced characteristics of invasiveness and malignancy (Stevens et al., 2009). Similarly, MTAP deficiency in hepatocellular carcinoma (HCC) also showed a strong correlation with increased MTA levels and HCC proliferation and increased the pro-tumorigenic gene expression profile in hepatic stellate cells (Kirovski et al., 2011).

Loss of the MTAP gene was commonly thought to be a simple bystander co-deletion along with CDKN2A, a cell cycle regulator, due to their proximity on chromosome 9p21. However, in studies of gastric carcinoma and cutaneous T-cell lymphomas, MTAP deletions were found to occur independently of CDKN2A loss and correlate with worse outcomes (Kim et al., 2011; Woollard et al., 2016). In a murine knockout model, it was found that while homozygous MTAP$^{-/-}$ null mice have an embryonically lethal phenotype, MTAP$^{+/-}$ heterozygotes develop normally but die prematurely of T-cell lymphoma (Kadariya et al., 2009). In line with these findings, the autosomal dominant hereditary malignancy, diaphyseal medullary stenosis with malignant fibrous histiocytoma (DMSMFH), results from mutations within the MTAP gene that lead to exon skipping, alternative splicing, and ultimately a dysfunctional MTAP gene product, indicative of a tumor suppressive role independent of CDKN2A (Camacho-Vanegas et al., 2012).

Deletion or repression of MTAP leads to the buildup and excretion of MTA, which has been shown to have potent immunosuppressive properties. Incubation with MTA halts the proliferation and differentiation of nave lymphocytes and is cytotoxic to activated human T cells. In particular, MTA halts the expansion of antigen-specific CD8$^+$ T cells, prevents the upregulation of activation markers, such as CD25 and CD69, and induces apoptosis in pre-stimulated cytotoxic T lymphocytes (Henrich et al., 2016). Earlier reports have also indicated that exogenous MTA inhibits DNA synthesis, protein synthesis, and proliferation of human lymphocyte cultures stimulated with antigens or allogeneic cells, an effect that could be reversed by washing the cells free of MTA (Vandenbark et al., 1980). Mechanistically, recent reports have indicated that the SAM dependent protein arginine methyltransferases (PRMTs) that regulate chromatin remodeling and gene expression by methylation of histones play a significant role in facilitating the immunosuppressive effects of MTA. In particular, PRMT5 expression was shown to play an essential role in memory T cell activation and expansion (Webb, Amici et al. 2017). It has been reported that while MTA is not a significant inhibitor of most methyltransferases, it is a quite potent inhibitor of PRMT5 with a $K_1$ of 0.26 µM (Marjon, Cameron et al. 2016) and thus likely contributes to the immunosuppressive mechanism of action of MTA. For example, both MTA and PRMT5 inhibitors have been shown to reduce T-cell proliferation, viability, and functionality (Strobl, Schaffer et al. 2020).

MTA may also act as an agonist of the adenosine receptors A2a and A2b, creating a tolerogenic phenotype in macrophages (Keyel et al., 2014). Similarly, in experiments with malignant melanoma, MTA was observed to cause a tumor promoting role in fibroblasts by induction of basic fibroblast growth factor (bFGF) and matrix metalloproteinase 3 (MMP3) (Stevens et al., 2009). The evidence that the consequence of MTAP deletion acts to suppress immune effector cells and promote tolerogenic stromal cell phenotypes through the buildup of MTA now suggests a clear mechanism for why this is one of the most common gene deletions in cancer. Tumor excreted MTA may be considered an immune checkpoint that helps tumor cells evade immune surveillance and elimination.

SUMMARY OF THE INVENTION

Provided herein, in some embodiments, are compositions. In an aspect, a composition comprises a polypeptide having methylthioadenosine phosphorylase activity, wherein at least one amino acid residue of the polypeptide has been engineered to eliminate a conjugation site.

In some embodiments, the polypeptide comprises an amino acid sequence with at least 80% homology to at least 100 consecutive amino acids of SEQ ID NO: 1 and comprises amino acids corresponding to Threonine 18, Threonine 197, Serine 178, Valine 233 and Methionine 196 of SEQ ID NO: 1. In some embodiments, the at least one amino acid residue of the polypeptide comprises a first lysine or a first cysteine. In some embodiments, an amino acid corresponding to Lysine 225 of SEQ ID NO: 1 that is engineered to eliminate a conjugation site. In some embodiments, an amino acid corresponding to Lysine 238 of SEQ ID NO: 1 is engineered to eliminate a conjugation site. In some embodiments, the amino acid corresponding to Lysine 225 or the amino acid corresponding to Lysine 238 are substituted with Arginine.

In some embodiments, a $K_{cat}/K_m$ of said polypeptide for phosphorolysis of methylthioadenosine into methylthioribose-phosphate and adenine is at least $1.5 \times 10^5 M^{-1} s^{-1}$. In some embodiments, a $K_{cat}/K_m$ of said polypeptide for phosphorolysis of methylthioadenosine into methylthioribose-phosphate and adenine is from about $1.5 \times 10^5 \ M^{-1} s^{-1}$ to $3.0 \times 10^5 M^{-1} s^{-1}$. In some embodiments, a $K_{cat}/K_m$ of said polypeptide for phosphorolysis of methylthioadenosine into methylthioribose-phosphate and adenine is at least 50% of a $V_{max}$ of a methylthioadenosine phosphorylase comprising SEQ ID NO: 1. In some embodiments, a $V_{max}$ of the polypeptide for phosphorolysis of methylthioadenosine into methylthioribose-phosphate and adenine is at least 50% of a $V_{max}$ of a methylthioadenosine phosphorylase comprising SEQ ID NO: 1. In some embodiments, a $K_m$ of the polypeptide for phosphorolysis of methylthioadenosine into methylthioribose-phosphate and adenine is no more than twice a $K_m$ of a methylthioadenosine phosphorylase comprising SEQ ID NO: 1.

In some embodiments, the composition comprises at least one polymer conjugated to the polypeptide described herein and thereof, wherein the polymer increases a serum half-life of the polypeptide compared to an unconjugated polypeptide. In some embodiments, the at least one polymer is a polyethylene glycol. In some embodiments, the polyethylene glycol has an average molecular weight of about 5000 kDa. In some embodiments, the polyethylene glycol has an average molecular weight of about 500 kDa to about 1000 kDa, about 800 kDa to about 1600 kDa, about 1500 kDa to about 3000 kDa, about 2000 kDa to about 4000 kDa, about 2500 kDa to about 5000 kDa, about 3000 kDa to about 6000 kDa, about 4,000 kDa to about 8,000 kDa, about 6,000 kDa to about 12,000 kDa, about 10,000 kDa to about 20,000 kDa, or about 15,000 kDa to about 30,000 kDa. In some embodiments, the at least one polymer is conjugated to a second lysine or a second cysteine of the polypeptide.

In some embodiments, the composition comprises a population of polypeptides described herein and thereof, wherein the population comprises trimers of the polypeptides. In some embodiments, the composition comprises a population of polypeptides described herein and thereof, wherein at least 80% of the polypeptides comprise the at least one polymer. In some embodiments, the at least 80% of the polypeptides comprise at least three of the at least one polymer. In some embodiments, the least 80% of the polypeptides comprise at least six of the at least one polymer. In some embodiments, the number of polymers per polypeptide comprises a Gaussian distribution. In some embodiments, the Gaussian distribution has a mode of 2±1, 3±1, 4±1, or 6±1 polymers per polypeptide. In some embodiments, the Gaussian distribution has a mode of 8±3 polymers per polypeptide.

In some embodiments, a $K_{cat}/K_m$ of said polypeptide for phosphorolysis of methylthioadenosine into methylthioribose-phosphate and adenine is at least $1.5 \times 10^5 M^{-1} s^{-1}$. In some embodiments, a $K_{cat}/K_m$ of said polypeptide for phosphorolysis of methylthioadenosine into methylthioribose-phosphate and adenine is from about $1.5 \times 10^5 1\backslash 4^{-1} s^{-1}$ to $3.0 \times 10^5 M^{-1} s^{-1}$. In some embodiments, a $K_{cat}/K_m$ of said polypeptide for phosphorolysis of methylthioadenosine into methylthioribose-phosphate and adenine is at least 50% of a $V_{max}$ of a methylthioadenosine phosphorylase comprising SEQ ID NO: 1. In some embodiments, a $V_{max}$ of the methylthioadenosine phosphorylase activity of the polypeptide is at least 50% of a $V_{max}$ of the methylthioadenosine phosphorylase activity of a methylthioadenosine phosphorylase comprising SEQ ID NO: 1. In some embodiments, a $K_m$ of the methylthioadenosine phosphorylase activity of the polypeptide is no more than twice a $K_m$ of the methylthioadenosine phosphorylase activity of a methylthioadenosine phosphorylase comprising SEQ ID NO: 1.

In some embodiments, the composition further comprises a heterologous peptide segment. In some embodiments, the heterologous peptide segment comprises a targeting moiety. In some embodiments, the targeting moiety comprises an antibody or fragment thereof, or a peptide.

Provided herein, in some embodiments, are nucleic acids. In an aspect, a nucleic acid comprises a nucleotide sequence encoding the polypeptide described herein and thereof.

In some embodiments, the nucleic acid is codon optimized for expression in bacteria, fungus, insects, or mammals. In some embodiments, the nucleic acid is codon optimized for expression in bacteria. In some embodiments, the bacteria are *E. coli*. In some embodiments, the nucleic acid comprises a sequence according to one of SEQ ID NOs: 4 and 6.

Provided herein, in some embodiments, are expression vectors. In an aspect, an expression vector can comprise the nucleic acid described herein and thereof.

Provided herein, in some embodiments, are host cells. In an aspect, a host cell comprises the nucleic acid described herein and thereof.

In some embodiments, the host cell is a bacterial cell, a fungal cell, an insect cell, or a mammalian cell. In some embodiments, the bacterial cell is an *E. coli* cell.

Provided herein, in some embodiments, are pharmaceutical formulations. In some embodiments, a pharmaceutical formulation comprises the composition described herein and thereof in a pharmaceutically acceptable carrier.

Provided herein, in some embodiments, are methods of treating a patient with a tumor. In an aspect, a method of treating a patient with a tumor comprises administering to the patient an effective amount of a composition comprising a polypeptide having methylthioadenosine phosphorylase activity, wherein the polypeptide has a serum-half of at least 36 hours.

In some embodiments, the composition is the pharmaceutical formulation described herein and thereof. In some embodiments, the patient was previously diagnosed with the tumor. In some embodiments, the patient has a solid tumor. In some embodiments, the tumor comprises a hematological tumor. In some embodiments, the tumor comprises a melanoma. In some embodiments, the tumor comprises a breast carcinoma. In some embodiments, the tumor comprises a colon carcinoma. In some embodiments, the tumor comprises an osteosarcoma, a pancreatic cancer, a chordoma, a mesothelioma, a T-cell ALL, a glioma, a renal cell carcinoma, a melanoma, a squamous cell carcinoma, a gallbladder cancer, a gastric cancer, or a hepatocellular carcinoma. In some embodiments, the tumor has an MTAP deletion. In some embodiments, the tumor has a decreased level of a methylthioadenosine phosphorylase polypeptide relative to a reference level. In some embodiments, the tumor has a decreased level of methylthioadenosine phosphorylase activity relative to a reference level. In some embodiments, the tumor has an increased level of CD73 relative to a reference level. In some embodiments, the tumor has an increased level of CD39 relative to a reference level. In some embodiments, the tumor has an increased level of MTA relative to a reference level. In some embodiments, the tumor has an increased level of ADO relative to a reference level. In some embodiments, the reference level is a level in a healthy subject. In some embodiments, the reference level is a level in a healthy tissue of the patient.

In some embodiments, the patient is a human patient. In some embodiments, the formulation is administered intratumorally, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage. In some embodiments, the pharmaceutical composition increases a sensitivity to an immunotherapy. In some embodiments, the patient has previously failed to respond to an administration of an immune checkpoint inhibitor.

In some embodiments, the method further comprises administering at least a second anticancer therapy to the subject. In some embodiments, the second anticancer therapy comprises a surgical therapy, chemotherapy, radiation therapy, cryotherapy, hormone therapy, immunotherapy or cytokine therapy. In some embodiments, the second anticancer therapy comprises an immune checkpoint inhibitor.

In some embodiments, the immune checkpoint inhibitor comprises an anti-PD-L1 antibody. In some embodiments, the anti-PD-L1 antibody comprises atezolizumab, avelumab, durvalumab, BMS-036559, or CK-301. In some embodiments, the immune checkpoint inhibitor comprises an anti-PD1 antibody. In some embodiments, the anti-PD1 antibody comprises nivolumab, pembrolizumab, pidilizumab, AMP-223, AMP-514, cemiplimab, or PDR-001. In some embodiments, the immune checkpoint inhibitor comprises an anti-CTLA-4 antibody. In some embodiments, the anti-CTLA-4 therapy comprises ipilimumab or tremelimumab. In some embodiments, the second anticancer therapy comprises an adoptive T-cell therapy. In some embodiments, the adoptive T-cell therapy is administered following the administration of the MTAP enzyme.

Provided herein, in some embodiments, are methods of treating a patient with a tumor. In an aspect, a method of treating a patient with a tumor comprises administering to the patient an adoptive T-cell therapy comprising T-cells that are engineered to express the MTAP enzyme. In some embodiments, metastasis of the cancer is delayed, reduced, or prevented.

Provided herein, in some embodiments, are uses of the MTAP enzyme described herein and thereof, the nucleic acid described herein and thereof, or the pharmaceutical composition described herein and thereof for manufacture of a medicament for therapeutic application to a patient having a tumor.

Provided herein are engineered mammalian MTAP enzymes (i.e., MTase enzymes) such that MTA and/or ADO in serum and tumor microenvironments can be efficiently degraded. The MTase enzymes and/or ADO degrading enzymes modified as described herein provide novel enzymes that comprise human, primate, mammalian, or prokaryotic polypeptide sequences having MTA- and/or ADO-degrading catalytic activity as compared to the native enzyme. As such, these modified enzymes may be suitable for cancer therapy and have low immunogenicity and improved serum stability. Without being bound by theory, any given MTase enzyme may efficiently degrade MTA only or may efficiently degrade both MTA and ADO.

Accordingly, in one embodiment there are provided modified polypeptides, particularly MTAP enzyme variants with MTA- and/or ADO-degrading activity. For example, the variant may be derived from a human enzyme, such as human MTAP. For example, an enzyme variant may have an amino acid sequence that is at least 95%, 96%, 97%, 98%, or 99% identical to a native MTAP sequence. The native polypeptides may have a MTAP sequence according to any one of SEQ ID NOs: 1 and 7-35. For example, an enzyme variant may have an amino acid sequence that is at least 95% identical to SEQ ID NO: 1. In certain aspects, there may be a polypeptide comprising a modified MTase capable of degrading MTA and/or ADO. In some embodiments, the polypeptide may be capable of degrading MTA and/or ADO under physiological conditions. For example, the polypeptide may have a catalytic efficiency for MTA and/or ADO ($k_{cat}/K_M$) of at least or about 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$ $s^{-1}M^{-1}$ or any range derivable therein.

To increase serum stability, the modified MTase may be linked to one or more polyether molecules. In a particular embodiment, the polyether may be polyethylene glycol (PEG). The modified polypeptide may be linked to PEG via specific amino acid residues, such as lysine or cysteine.

In some embodiments, the native MTase may be modified by one or more other modifications, such as chemical modifications, substitutions, insertions, deletions, and/or truncations. In a particular embodiment, the native MTase may be modified by substitutions. For example, the number of substitutions may be one, two, three, four or more.

In some cases, provided are compositions comprising a population of PEGylated native human methylthioadenosine phosphorylase (MTAP) enzymes, wherein the PEGylated MTAP enzymes each comprise a homotrimer of polypeptides each comprising a sequence at least 95% identical to SEQ ID NO: 1, wherein at least about 80% of the PEGylated MTAP enzymes comprise 1, 2, 3, 4, or 5 polyethylene glycol (PEG) molecules per subunit. In some aspects, the at least about 80% of the PEGylated MTAP enzymes comprising 1, 2, 3, 4, or 5 PEG molecules per subunit have a Gaussian distribution of PEG molecules per subunit. In some aspects, the at least about 80% of the PEGylated MTAP enzymes comprising 1, 2, 3, 4, or 5 PEG molecules per subunit have a mode of 3±1 PEG molecules per subunit. In some aspects, no more than 20% of the PEGylated MTAP enzymes comprise 0, 6, 7, 8, or more PEG molecules per subunit. In some aspects, the PEG molecules have a molecular weight of about 5000.

In some cases, provided are polypeptides comprising a variant of a native human methylthioadenosine phosphorylase (MTAP) enzyme, wherein the variant MTAP comprises a sequence at least 95% identical to SEQ ID NO: 1 and comprises a K225R (see, e.g., SEQ ID NO: 3) or K238R (see, e.g., SEQ ID NO: 5) substitution relative to SEQ ID NO: 1. In this case, the polypeptides may be PEGylated to any extent desirable.

In some aspects, the present invention also contemplates polypeptides comprising the modified MTase linked to a heterologous amino acid sequence. For example, the modified MTase may be linked to the heterologous amino acid sequence as a fusion protein. In a particular embodiment, the modified MTase may be linked to amino acid sequences, such as an IgG Fc, albumin, an albumin binding peptide, or an XTEN polypeptide for increasing the in vivo half-life.

In some aspects, a nucleic acid encoding such a modified MTase is contemplated. In one aspect, the nucleic acid has been codon optimized for expression in bacteria. In particular embodiments, the bacteria is E. coli. In other aspects, the nucleic acid has been codon optimized for expression in a fungus (e.g., yeast), in insect cells, or in mammalian cells. The present invention further contemplates vectors, such as expression vectors, containing such nucleic acids. In particular embodiments, the nucleic acid encoding the modified MTase is operably linked to a promoter, including but not limited to heterologous promoters. In one embodiment, a modified MTase may be delivered to a target cell by a vector (e.g., a gene therapy vector). Such viruses may have been modified by recombinant DNA technology to enable the expression of the modified MTase-encoding nucleic acid in the target cell. These vectors may be derived from vectors of non-viral (e.g., plasmids) or viral (e.g., adenovirus, adeno-associated virus, retrovirus, lentivirus, herpes virus, or vaccinia virus) origin. Non-viral vectors are preferably complexed with agents to facilitate the entry of the DNA across the cellular membrane. Examples of such non-viral vector complexes include the formulation with polycationic agents which facilitate the condensation of the DNA and lipid-based delivery systems. An example of a lipid-based delivery system would include liposome-based delivery of nucleic acids.

In still further aspects, the present invention further contemplates host cells comprising such vectors. The host cells may be bacteria (e.g., E. coli), fungal cells (e.g., yeast), insect cells, or mammalian cells.

In some embodiments, the vectors are introduced into host cells for expressing the modified MTase. The proteins may be expressed in any suitable manner. In one embodiment, the proteins are expressed in a host cell such that the protein is glycosylated. In another embodiment, the proteins are expressed in a host cell such that the protein is aglycosylated.

In some embodiments, the polypeptides or nucleic acids are in a pharmaceutical formulation comprising a pharmaceutically acceptable carrier. The polypeptide may be a native PEGylated MTase polypeptide or a modified MTase polypeptide. The nucleic acid may encode a native PEGylated MTase polypeptide or a modified MTase polypeptide.

In one embodiment, methods are provided for treating a patient having or at risk of developing cancer comprising administering to the subject a therapeutically effective amount of a formulation comprising an MTase as described above. The patient may be any animal, such as a mouse. For example, the patient may be a mammal, particularly a primate, and more particularly a human patient.

In some aspects, the tumor is a solid tumor. In some aspects, the tumor is a hematological tumor. In some aspects, the tumor is an osteosarcoma, a pancreatic cancer, a chordoma, a mesothelioma, a T-cell ALL, a glioma, a renal cell carcinoma, a melanoma, a squamous cell carcinoma, a gallbladder cancer, a gastric cancer, or a hepatocellular carcinoma.

In some aspects, the tumor has decreased levels of MTAP. In certain aspects, the tumor has an MTAP deletion. In some aspects, the tumor has an increased level of CD73 relative to a reference sample. In some aspects, the tumor has an increased level of CD73 and, optionally, a decreased level of MTAP relative to a reference level. In some aspects, the tumor has an increased level of CD39 relative to a reference sample. In some aspects, the tumor has an increased level of MTA relative to a reference level. In some aspects, the tumor has an increased level of ADO relative to a reference level. In some aspects, the reference level is a level in a healthy tissue in the patient. In some aspects, the reference level is a level in a healthy subject.

In some aspects, the patient has previously been treated for cancer and the enzyme is administered to prevent the recurrence of cancer. In some aspects, the method is a method of preventing metastasis. In some aspects, the method is a method for increasing sensitivity to immunotherapy. In some aspects, the patient has previously failed to respond to the administration of an immune checkpoint inhibitor. In some aspects, the method further comprises administering at least a second anti-cancer therapy to the subject. In some aspects, the second anti-cancer therapy is an immune checkpoint blockade, an adoptive T cell therapy, a surgical therapy, chemotherapy, radiation therapy, cryotherapy, hormone therapy, immunotherapy or cytokine therapy. In some aspects, the second anticancer therapy comprises an adoptive T cell therapy, an anti-PD1 antibody, an anti-CTLA-4 antibody, and/or an anti-PD-L1 antibody. In certain aspects, the anti-PD-L1 antibody comprises atezolizumab, avelumab, durvalumab, BMS-036559, or CK-301. In certain aspects, the anti-PD1 antibody comprises nivolumab, pembrolizumab, pidilizumab, AMP-223, AMP-514, cemiplimab, or PDR-001. In certain aspects, the anti-CTLA-4 therapy comprises ipilimumab or tremelimumab. In some aspects, the adoptive T-cell therapy is administered following the administration of the variant MTAP enzyme. In some aspects, the adoptive T-cell therapy comprises cells that are engineered to express the variant MTAP enzyme.

In some embodiments, the cancer is any cancer that is sensitive to MTA depletion. In one embodiment, the present invention contemplates a method of treating a tumor cell or a cancer patient comprising administering a formulation comprising such a polypeptide. In some embodiments, the administration occurs under conditions such that at least a portion of the cells of the cancer are killed. In another embodiment, the formulation comprises such a modified MTase with MTA-degrading activity at physiological conditions and further comprising an attached polyethylene glycol chain. In some embodiment, the formulation is a pharmaceutical formulation comprising any of the above discussed MTase variants and pharmaceutically acceptable excipients. Such pharmaceutically acceptable excipients are well known to those of skill in the art. All of the above MTase variants may be contemplated as useful for human therapy.

In an in vivo application, treating a tumor cell includes contacting the nutrient medium for a population of tumor cells with the MTase. In this embodiment, the medium can be blood, lymphatic fluid, spinal fluid and the like bodily fluid where MTA-depletion is desired.

In accordance with certain aspects of the present invention, such a formulation containing the modified MTase can be administered intravenously, intradermally, intraarterially, intraperitoneally, intralesionally, intracranially, intraarticularly, intraprostaticaly, intrapleurally, intrasynovially, intratracheally, intranasally, intravitreally, intravaginally, intrarectally, intratumorally, intramuscularly, subcutaneously, subconjunctival, intravesicularlly, mucosally, intrapericardially, intraumbilically, intraocularly, orally, topically, by inhalation, infusion, continuous infusion, localized perfusion, via a catheter, via a lavage, in lipid compositions (e.g., liposomes), or by other method or any combination of the forgoing as would be known to one of ordinary skill in the art.

In one embodiment, a composition comprising a modified MTase or a nucleic acid encoding a modified MTase is provided for use in the treatment of a tumor in a subject. In another embodiment, the use of a modified MTase or a nucleic acid encoding a modified MTase in the manufacture of a medicament for the treatment of a tumor is provided. The modified MTase may be any modified MTase of the embodiments.

Embodiments discussed in the context of methods and/or compositions of the invention may be employed with respect to any other method or composition described herein. Thus, an embodiment pertaining to one method or composition may be applied to other methods and compositions of the invention as well.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings ("FIGURE" or "FIGUREs" herein), of which:

FIG. 1A provides an SDS-PAGE gel of the *Homo sapiens* MTAP (hs-MTAP) polypeptide reacted with a 0, 10, 20, 50, or 100-fold molar excess (X) of PEG. FIGS. 1B-E compare the reaction kinetics of mock-PEGylated hs-MTAP polypeptide and hs-MTAP polypeptides modified with 10×PEG (FIG. 1B), 20×PEG (FIG. 1C), 50×PEG (FIG. 1D), and 100×PEG (FIG. 1E).

FIG. 2A provides an SDS-PAGE gel of hs-MTAP polypeptides with K225R and K238R substitutions reacted with 0× or 100×PEG. Comparison of reaction kinetics between the hs-MTAP-K225R polypeptide with 0× and 100×PEG (FIG. 2B) and hs-MTAP-K238R polypeptide with 0× and 100×PEG (FIG. 2C) are shown.

FIG. 3A shows that when treated with an anti-PD-L1 antibody, non-small cell lung carcinoma (NSCLC) patients homozygous for CDKN2A (CDKN2A−/−) had a shorter progression free survival compared to that of the NSCLC patients with wildtype CDKN2A or heterozygous CDKN2A mutant. FIG. 3B shows that deletion of one or both copies of MTAP contributes to immunosuppression in head and neck cancer. A statistically significant reduction in CD8A was only observed with deletion of the MTAP locus.

FIG. 4A illustrates how a PEGylated MTAP polypeptide might degrade MTA in the tumor microenvironment to potentiate T-cell infiltration. FIG. 4B shows a bar graph of the MTA level in the microenvironment of a leukemia allograft tumor (L1210) at 0, 4, or 24 hours after the addition of 50 mg/kg hs-MTAP.

FIGS. 5A-5B are line graphs showing the growth of MTAP+/+ (FIG. 5A) and MTAP−/− (FIG. 5B) B6-F10 melanoma cell allograft tumors in mice treated with or without a PEGylated-MTAP polypeptide (PEG-MTAP). PEG-MTAP treatment did not alter the growth of MTAP+/+ tumors compared to that of control. In contrast, PEG-MTAP treatment significantly reduce the growth of MTAP−/− tumors compared to that of control. Moreover, complete remission (CR) was observed in three out of seven mice with MTAP−/− tumors. FIG. 5C shows a Kaplan-Meier plot of survival of the mice in FIG. 5B. The average survival of mice treated with PEG-MTAP was about 32 days, 11 days more than that of control (21 days).

FIGS. 6A-D. CD8+ T-cells are required for inhibition of B6-F10 melanoma cell allograft tumor growth by MTAP. MTAP treatment significantly reduces the growth of the tumor (FIG. 6C) when compared to untreated controls (FIG. 6A). Two of six mice also achieved complete remission (CR). An anti-CD8 antibody increased the tumor growth (FIG. 6B) and blocks the effectiveness of the MTAP treatment (FIG. 6D).

FIGS. 7A-D. PEG-MTAP treatment can increase the numbers of CD8+/K167+ (FIG. 7A), CD4+/K167+ (FIG. 7B), and CD8+/GranzymeB+ (FIG. 7C) tumor infiltrating lymphocytes (TILs) in the tumor microenvironment of B6-F10 melanoma allograft tumors and the number of total lymphocytes in tumor draining lymph nodes (FIG. 7D).

FIG. 8A shows that PEG-hs-MTAP administration increased the percentage of CD4+ cells in the TCRβ+ cells. FIG. 8B shows that PEG-hs-MTAP administration increased the percentage of TCRβ−, NK1.1+ cells in CD45+ cells. FIG. 8C shows that PEG-hs-MTAP administration increased the percentage of CD8+/Granzyme B+ cells that are Ki67+.

FIG. 9A shows the growth of L1210 leukemia cell allograft tumors in mice after treatment with a MTAN polypeptide from *Salmonella enterica* (PEG-se-MTAN) or PBS vehicle control. PEG-se-MTAN significantly delayed the growth of the L1210 tumor. FIG. 9B shows a Kaplan-Meier plot of survival of the treated and untreated mice of FIG. 9A (p<0.0035). Treatment with PEG-se-MTAN increased the survival of mice with L1210 murine leukemia allograft tumors.

FIG. 11A shows the relationship of the tumor volume (mm$^3$) and time (days elapsed) following treatment with a vehicle (top left), PEG-MTAN polypeptide (top right), anti-CTLA4 antibody (bottom left), or a combination of the PEG-MTAN polypeptide and anti-CTLA4 antibody (bottom right). While individual administration of the PEG-MTAN polypeptide (50 mg/kg) or the anti-CTLA4 antibody (10 mg/kg, clone UC10-4F10-11, Bio X Cell) suppressed the growth of the tumor, their combination provided a stronger inhibition that those of either treatment alone. FIG. 11B shows the number of lung metastases following treatment with the vehicle, PEG-MTAN polypeptide, anti-CTLA4, or the combination of PEG-MTAN polypeptide and anti-CTLA4 antibody. The PEG-MTAN polypeptide (50 mg/kg), the anti-CTLA4 antibody (10 mg/kg, clone UC10-4F10-11, Bio X Cell), or their combination significantly reduced the number of lung metastases.

DETAILED DESCRIPTION OF THE INVENTION

Figure 1A:
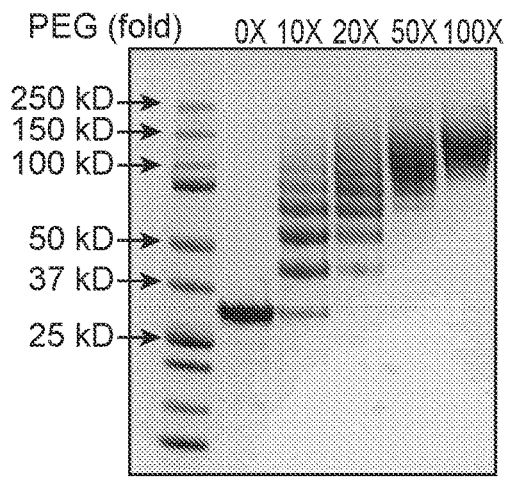
FIGS. 1A-E. Defined PEGylation and its impact on the pharmacological kinetics of an MTAP polypeptide from *Homo sapiens*.

Provided herein are polypeptides, nucleic acids, vectors, host cells, methods, pharmaceutical compositions, and kits to provide a PEGylated MTAP polypeptide for cancer therapy. In some instances, a PEGylated MTAP polypeptide may have a higher catalytic activity or protein stability in an extracellular environment comprising serum.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Definitions

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, the variation that exists among the study subjects, or a value that is within 10% of a stated value.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

The terms "contacted" and "exposed," when applied to a cell, are used herein to describe the process by which a therapeutic construct is delivered to a target organ or are placed in direct juxtaposition with the target cell.

"Homology" or "identity" or "similarity" can refer to sequence similarity between two peptides or between two nucleic acid molecules. Homology can be determined by comparing a position in each sequence which can be aligned for purposes of comparison. When a position in the compared sequence can be occupied by the same base or amino acid, then the molecules can be homologous at that position. A degree of homology between sequences can be a function of the number of matching or homologous positions shared by the sequences. An "unrelated" or "non-homologous" sequence shares less than 40% identity, or alternatively less than 25% identity, with one of the sequences of the disclosure. Sequence homology can refer to a % identity of a sequence to a reference sequence. As a practical matter, whether any particular sequence can be at least 50%, 60%, 70%, 80%, 85%, 90%, 92%, 95%, 96%, 97%, 98% or 99% identical to any sequence described herein (which can correspond with a particular nucleic acid sequence described herein), such particular polypeptide sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence, the parameters can be set such that the percentage of identity can be calculated over the full length of the reference sequence and that gaps in sequence homology of up to 5% of the total reference sequence can be allowed.

The terms "polynucleotide", "oligonucleotide", or "nucleic acid" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), an exon, an intron, intergenic DNA (including, without limitation, heterochromatic DNA), messenger RNA (mRNA), cDNA, a recombinant polynucleotide, a branched polynucleotide, a plasmid, a vector, isolated DNA of a sequence, isolated RNA of a sequence. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double and single stranded molecules. Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent, or other interaction. Unless otherwise specified or required, any embodiment of this disclosure that is a polynucleotide encompasses both the double stranded form and each of two complementary single stranded forms known or predicted to make up the double stranded form.

Polynucleotides useful in the methods of the disclosure can comprise natural nucleic acid sequences and variants thereof, artificial nucleic acid sequences, or a combination of such sequences. In some embodiments, polynucleotides of the disclosure refer to a DNA sequence. In some embodiments, the DNA sequence is interchangeable with a similar RNA sequence. In some embodiments, polynucleotides of the disclosure refer to an RNA sequence. In some embodiments, the RNA sequence is interchangeable with a similar DNA sequence. In some embodiments, Us and Ts of a polynucleotide may be interchanged in a sequence provided herein.

"Canonical amino acids" refer to those 20 amino acids found naturally in the human body. Substitution, mutation, or replacement variants typically contain the exchange of one amino acid for another at one or more sites within the protein and may be designed to modulate one or more properties of the polypeptide, particularly its effector functions and/or bioavailability.

Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

The term "protein", "peptide", and "polypeptide" are used interchangeably and in their broadest sense to refer to a compound of two or more subunit amino acids, amino acid analogs or peptidomimetics. The terms also encompass an amino acid polymer that has been modified; for example, disulfide bond formation, glycosylation, lipidation, acetylation, phosphorylation, or any other manipulation, such as conjugation with a labeling component.

The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

The terms "cell," and "cells," and "cell population," used interchangeably, intend one or more mammalian cells. The term includes progeny of a cell or cell population. Those skilled in the art will recognize that "cells" include progeny of a single cell, and there are variations between the progeny and its original parent cell due to natural, accidental, or deliberate mutation or change.

The term "immunotherapy" refers to treatment of disease (e.g., cancer) by modulating an immune response to a disease antigen.

The term "cancer cell" as used herein refers to a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth or development in an immunocompromised non-human animal model, or any appropriate indicator of cellular transformation. "Cancer cell" may be used interchangeably herein with "tumor cell" or "cancerous cell" and encompasses cancer cells of a solid tumor and a liquid tumor. "Cancer" may be used interchangeably herein with "tumor".

The term "solid tumor" or "solid cancer" as used herein refers to tumors that usually do not contain cysts or liquid areas. Solid tumors can include brain and other central nervous system tumors (including but not limited to tumors of the meninges, brain, spinal cord, cranial nerves and other parts of central nervous system, e.g. glioblastomas or medulla blastomas); head or neck cancer; breast tumors; circulatory system tumors (including but not limited to heart, mediastinum and pleura, and other intrathoracic organs, vascular tumors and tumor-associated vascular tissue); excretory system tumors (including but not limited to tumors of kidney, renal pelvis, ureter, bladder, other and unspecified urinary organs); gastrointestinal tract tumors (including but not limited to tumors of oesophagus, stomach, small intestine, colon, colorectal, rectosigmoid junction, rectum, anus and anal canal, tumors involving the liver and intrahepatic bile ducts, gall bladder, other and unspecified parts of biliary tract, pancreas, other and digestive organs); oral cavity tumors (including but not limited to tumors of lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx); reproductive system tumors (including but not limited to tumors of vulva, vagina, Cervix uteri, Corpus uteri, uterus, ovary, and other sites associated with female genital organs, placenta, penis, prostate, testis, and other sites associated with male genital organs); respiratory tract tumors (including but not limited to tumors of nasal cavity and middle ear, accessory sinuses, larynx, trachea, bronchus and lung, e.g. small cell lung cancer or non-small cell lung cancer); skeletal system tumors (including but not limited to tumors of bone and articular cartilage of limbs, bone articular cartilage and other sites); skin tumors (including but not limited to malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneum and peritoneum, eye and adnexa, thyroid, adrenal gland and other endocrine glands and related structures, secondary and unspecified malignant neoplasm of lymph nodes, secondary malignant neoplasm of respiratory and digestive systems and secondary malignant neoplasm of other sites.

The term "liquid cancer" or "liquid tumor" as used herein refers to cancer cells that are present in body fluids, such as blood, lymph and bone marrow. Liquid cancers include leukemia, myeloma, myelodysplastic syndrome (MDS), and liquid lymphomas. Liquid lymphomas include lymphomas that contain cysts or liquid areas. Liquid cancers as used herein do not include solid tumors, such as sarcomas and carcinomas or solid lymphomas that do not contain cysts or liquid areas.

As used herein, the term "conjugate" refers to at least two molecules or molecular moieties being linked together by a covalent bond. A molecule or molecular moiety is considered to be "conjugated" to another molecule or molecular moiety once they are linked by the bond. Hence, "unconjugated" molecules or molecular moieties are not linked by a covalent bond.

The term "PEGylation" refers to the process of covalent attachment of a polyethylene glycol (PEG) molecule(s) to another molecule including but not limited to a protein or a drug. A protein that has undergone PEGylation can be referred to as being "PEGylated". A PEGylated polypeptide may have properties that are qualitatively or quantitively different from a comparable polypeptide without a PEGylation or a polypeptide not PEGylated.

The term "effective amount" is an amount sufficient to effect beneficial or desired clinical results. An effective amount can be administered in one or more administrations. For purposes of this application, an effective amount of an antibody or polypeptide is an amount that is sufficient to diagnose, palliate, ameliorate, stabilize, reverse, slow or delay the progression of the disease state.

As used herein, the term "fusion protein" refers to a chimeric protein containing proteins or protein fragments operably linked in a non-naturally occurring way. A fusion protein may comprise a protein comprised of domains from more than one naturally occurring or recombinantly produced protein, where generally each domain serves a different function. In this regard, the term "linker" refers to a protein fragment that is used to link these domains together optionally to preserve the conformation of the fused protein domains and/or prevent unfavorable interactions between the fused protein domains which may compromise their respective functions.

As used herein, the term "half-life" (½-life; T ½) refers to the time that would be required for the concentration of a polypeptide thereof to fall by half in vitro or in vivo, for example, after injection in a mammal.

The terms "in operable combination", "in operable order", and "operably linked" refer to a linkage wherein the components so described are in a relationship permitting them to function in their intended manner, for example, a linkage of nucleic acid sequences in such a manner that a nucleic acid molecule capable of directing the transcription of a given gene or the synthesis of desired protein molecule, or a linkage of amino acid sequences in such a manner so that a fusion protein is produced.

The term "$K_M$" as used herein refers to the Michaelis-Menten constant for an enzyme and is defined as the concentration of the specific substrate at which a given enzyme yields one-half its maximum velocity in an enzyme catalyzed reaction. $K_M$ may be used to measure the substrate binding affinity of an enzyme.

The term "$k_{cat}$" as used herein refers to the turnover number or the number of substrate molecules each enzyme site converts to product per unit time, and in which the enzyme is working at maximum efficiency. $k_{cat}$ may be used to measure the catalytic rate of an enzyme.

The term "$k_{cat}/K_M$" as used herein is the specificity constant, which is a measure of how efficiently an enzyme converts a substrate into product. $k_{cat}/K_M$ may be used to measure the catalytic efficiency of an enzyme.

The term "$V_{max}$" as used herein refers to the maximal rate of an enzymatic reaction. An enzymatic reaction may reach maximum velocity when the enzyme is saturated with substrates. $V_{max}$ may be a product of $k_{cat}$ and enzyme concentration. $V_{max}$ may be used to measure the catalytic rate of an enzyme.

The term "catalytic activity" as used herein refers to any qualitative or quantitative properties of the enzymatic kinetics of substrate conversion or production of an enzyme. Catalytic activity may be measured using $K_M$, $k_{cat}$, $V_{max}$, or any derivatives herein and thereof. Other enzymatic kinetics measure may also be used.

The term "MTase" refers to any enzyme that catalyzes the phosphorolysis or hydrolysis of MTA into methylthioribose-1-phosphate (MTR-1-R) or methylthioribose (MTR) and adenine as well as the phosphorolysis or hydrolysis of adenosine into ribose-1-phosphate or ribose and adenine. It can have roles in the metabolism of polyamine and the adenine and methionine salvage pathway. It can include primate forms of, or particularly, human forms of MTAP, or prokaryotic forms of MTAN.

The term "MTAP" refers to the methylthioadenosine phosphorylase. It can catalyze the phosphorolysis of MTA into methylthioribose-1-phosphate (MTR-1-R) and adenine as well as the phosphorolysis of adenosine into ribose-1-phosphate and adenine. A human form of MTAP may be referred to as *Homo sapiens* MTAP or hs-MTAP. Unless otherwise specified, MTAP may mean the polypeptide or the gene or nucleic acid encoding an MTAP polypeptide. Unless otherwise specified, MTAP may also mean a PEGylated MTAP polypeptide or PEG-conjugated MTAP polypeptide.

The term "MTAN" refers to the methylthioadenosine nucleosidase. It can catalyze the hydrolysis of MTA into methylthioribose (MTR) and adenine as well as the hydrolysis of adenosine into ribose and adenine. A prokaryotic form of MTAN can comprise bacterial MTAN, e.g., a *Salmonella enterica* MTAN or se-MTAN. Unless otherwise specified, MTAN may mean the polypeptide or the gene or nucleic acid encoding an MTAN polypeptide. Unless otherwise specified, MTAN may also mean a PEGylated MTAN polypeptide or PEG-conjugated MTAN polypeptide.

The term "human" refers to *Homo sapiens*.

The term "conjugation site" of a polypeptide refers to an amino acid residue or chemical group that serves as the site for a covalent bonding, attachment, conjugation, or linkage to another entity. One exemplary entity is a PEG polymer.

A PEGylated Methylthioadenosine Phosphorylase (MTAP) Polypeptide for Treating Cancer An MTase, in some instances, can be used to treat a disease. In some instances, a disease can comprise a cancer. In other cases, a disease can comprise a disease associated with an immune system. In some cases, a disease can comprise a condition associated with a defect in methylthioadenosine phosphorylase activity. A defect in methylthioadenosine phosphorylase activity, in some case, can arise from a genetic or non-genetic loss, inhibition, mutation, or down-regulation of MTAP.

An MTase, in some instances, can have an methylthioadenosine phosphorylase activity. In some cases, an methylthioadenosine phosphorylase activity can comprise an enzymatic activity that can carry out phosphorolysis of methylthioadenosine (MTA) into methylthioribose-phosphate and adenine. In some case, an MTase can comprise a MTAP polypeptide. In some case, an MTase can comprise a human MTAP polypeptide. In other cases, an MTase can comprise an enzymatic activity that can carry out hydrolysis of MTA to methylthioribose and adenine. In some cases, an MTase can comprise a bacterial MTAN such as a *Salmonella enterica* MTAN. In some instances, an methylthioadenosine phosphorylase activity can convert phosphate and S-methyl-5'thioadenosine into adenine and S-methyl-5-thio-α-D-ribose 1-phosphate. In some instances, an methylthioadenosine phosphorylase activity may be inhibited by 5'-methylthiotubercin or 5'-chloroformycin. In some cases, MTAP's activity can be found in bacteria, yeast, mouse, bovine, human, or other organisms.

In some cases, an MTase can comprise a polypeptide that can catabolize MTA or adenosine (ADO). In some embodiments, an MTase can degrade extracellular or intracellular MTA or ADO. In some cases, extracellular MTA or ADO can be present in tumor microenvironment (TME). In other embodiments, extracellular MTA or ADO can be present in serum. In some embodiments, an MTase can degrade MTA or ADO in serum. In other embodiments, an MTase can degrade MTA or ADO in TME.

In some embodiments, an MTase can comprise a bacterial, fungal, plant, or animal polypeptide with an MTA or ADO degradation activity. In some cases, an MTase polypeptide sequence can comprise a mammalian MTAP polypeptide that can degrade MTA or ADO. In some embodiments, an MTAP polypeptide sequence can comprise a human polypeptide that can degrade MTA or ADO. In other aspects, an MTase can comprise either a naturally occurring or modified MTAP polypeptide capable of degrading ADO or MTA. In yet other aspects, an MTase can comprise either a naturally occurring or modified MTAN or prokaryotic MTAN capable of degrading ADO or MTA. In some aspects, an MTase polypeptide can be capable of degrading ADO or MTA under physiological conditions. In other cases, an MTase polypeptide can be capable of degrading ADO or MTA under in vitro conditions.

In some cases, an MTAP polypeptide can comprise a naturally occurring or a non-naturally occurring MTAP polypeptide. A naturally occurring MTAP polypeptide can comprise an MTAP polypeptide with a wildtype sequence. In some embodiments, a naturally occurring MTAP polypeptide may be modified by one or more other modifications, such as chemical modifications, substitutions, insertions, deletions, fusion, or truncations. In some embodiments, a naturally occurring MTAP polypeptide can be modified by substitutions. In some embodiments, a naturally occurring MTAP polypeptide can be modified by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more substitutions. In some embodiments, a naturally occurring MTAP polypeptide can be modified by a conservative substitution, a non-conservative substitution, a deletion or an insertion at a site that is outside of its active site, base-binding site, or methylthioribose-binding site and still maintain its catalytic activity. In other cases, a naturally occurring MTAP polypeptide can be modified in a location that can modulate the protein binding activity, protein stability, protein localization, non-substrate binding activity, chemical modification activity, protein ability to be chemically modified, protein folding, protein transport, any derivatives herein and thereof, or any combination herein and thereof. A modulation described herein and thereof can comprise an increase or decrease.

In some embodiments, an MTAP polypeptide can comprise the sequence or a portion thereof of SEQ ID NO: 1.

In some cases, an MTAP polypeptide with MTAP activity can comprise sequence having about, at least 60%, 65%, 70%, 75%, 80%, 85%, 90%, 95%, 96%, 97%, 98%, 99% or 100% identity (or any range derivable therein) to SEQ ID NO: 1 or a portion thereof. In some embodiments, an MTAP polypeptide with MTAP activity can comprise at least or up to about 10, 20, 30, 40, 50, 60, 70, 80, 90, 100, 110, 120, 130, 140, 150, 160, 170, 180, 190, 200, 210, 220, 230, 240, 250, 260, 270, 280, or 284 residues of SEQ ID NO: 1. In some cases, an MTAP polypeptide with MTAP activity can comprise 1-10, 5-15, 10-20, 15-25, 20-30, 25-35, 30-40, 35-45, 40-50, 45-55, 50-60, 55-65, 60-70, 65-75, 70-80, 75-85, 80-90, 85-95, 90-100, 95-105, 100-110, 105-115, 110-120, 115-125, 120-130, 125-135, 130-140, 135-145, 140-150, 145-155, 150-160, 155-165, 160-170, 165-175, 170-180, 175-185, 180-190, 185-195, 190-200, 195-205, 200-210, 205-215, 210-220, 215-225, 220-230, 225-235, 230-240, 235-245, 240-250, 245-255, 250-260, 255-265, 260-270, 265-275, 270-280, or 275-284 residues of SEQ ID NO: 1. In some cases, an MTAP polypeptide with MTAP activity can comprise a sequence having about at least 80% identity to at least 200 amino acids of SEQ ID NO: 1. In some cases, an MTAP polypeptide with MTAP activity can comprise sequence having about at least 80% identity to at least 200 amino acids of SEQ ID NO: 1 and Thr18, Thr197, Ser178, Val233 and Met196 of SEQ ID NO: 1.

In some cases, three MTAP polypeptides can combine as a homotrimer with three identical submits of about 32 kDa. In other cases, two MTAP polypeptides can combine as a homodimer (Appleby et al., 1999). In some instances, an MTAP polypeptide homotrimer can comprise three identical or similar subunits related by C3 symmetry. In some instances, the active site of each MTAP polypeptide in a MTAP polypeptide homotrimer can be located near the interface between each MTAP polypeptide. In some cases, an active site of an MTAP polypeptide with a sequence of SEQ ID NO: 1 can comprise T18, R60, H61, T93, A94, F177, S178, M196, T197, T219, D220, D222, V233, V236, or L237 of the MTAP polypeptide. In some cases, an active site of a first MTAP polypeptide with a sequence of SEQ ID NO: 1 can comprise H137 or L279 of a second MTAP polypeptide with a sequence of SEQ ID NO:1 making an interface of the first MTAP polypeptide in a homotrimer. In some cases, an active of an MTAP polypeptide can comprise a structurally equivalent residue of T18, R60, H61, T93, A94, F177, S178, H137, M196, T197, T219, D220, D222, V233, V236, L237, or L279 of SEQ ID NO: 1. Such a structurally equivalent residue can be identified based on the 3-dimensional structure of the MTAP polypeptide described by Appleby et al., which is herein incorporated by reference in its entirety.

A PEGylated MTAP Polypeptide

In some instances, a PEGylated MTAP polypeptide can have a modified, eliminated, or added property compared to a MTAP polypeptide that is not PEGylated. In some instances, a PEGylated MTAP polypeptide can have a modulated property compared to a MTAP polypeptide that is not PEGylated. In some cases, a PEGylated MTAP polypeptide can a modulated size, solubility, accessibility for proteolytic enzyme, immunogenicity and antigenicity, body-residence, stability, or any combination herein and thereof. In some cases, a PEGylated MTAP polypeptide can have an increase in size, increase in solubility, decreased accessibility for proteolytic enzyme, decrease in immunogenicity and antigenicity, increase in body-residence time and stability, or any combination herein and thereof.

In some cases, an MTAP polypeptide can be PEGylated at a lysine residue. In some instances, an MTAP polypeptide can be engineered to remove a lysine residue to prevent the lysine residue from being PEGylated. In some instances, an MTAP polypeptide can be engineered to replace a lysine residue with another amino acid to prevent the lysine residue from being PEGylated. In some cases, the lysine residue that is substituted with another amino acid in an MTAP polypeptide can be located close to an active site or a binding site. In some cases, substituting a lysine residue close to an active site or binding site can prevent PEGylation at that lysine residue. In some cases, substituting a lysine residue close to an active site or a binding site can prevent a PEG molecule or a PEGylation reaction from affecting the catalytic activity or substrate specificity of the MTAP polypeptide. In some embodiments, a lysine residue of an MTAP polypeptide being substituted or deleted can comprise lysine (or K) 11, 32, 40, 49, 51, 71, 82, 147, 157, 158, 166, 206, 225, 238, 241, 246, 248, 271, or any combination thereof of SEQ ID NO: 1. In some cases, a lysine residue of an MTAP polypeptide being substituted or deleted can comprise K225 or K238 or any combination thereof of SEQ ID NO: 1. In some cases, a lysine residue of an MTAP polypeptide can be substituted with any one of the canonical amino acids comprising alanine, arginine, asparagine, aspartic acid, cysteine, glutamine, glutamic acid, glycine, histidine, isoleucine, leucine, methionine, phenylalanine, proline, serine, threonine, tryptophan, tyrosine, valine, or derivatives herein and thereof. In other cases, a lysine of an MTAP polypeptide can be substituted with any natural or non-natural amino acid residue or any derivative herein and thereof. In some cases, a lysine of an MTAP polypeptide can be substituted with an arginine.

In some cases, an MTAP polypeptide can be PEGylated at a cysteine residue. In some instances, an MTAP polypeptide can be engineered to remove a cysteine residue to prevent the cysteine residue from being PEGylated. In some instances, an MTAP polypeptide can be engineered to replace a cysteine residue with another amino acid to prevent the cysteine residue from being PEGylated. In some cases, the cysteine being replaced with another amino acid in an MTAP polypeptide can be located close to an active site or a binding site. In some cases, substituting a cysteine residue close to an active site or a binding can prevent PEGylation at that cysteine residue. In some cases, substituting a cysteine residue close to an active site or a biding site can prevent a PEG molecule or a PEGylation reaction from affecting the catalytic activity or substrate specificity of an MTAP polypeptide. In some instances, a cysteine residue of an MTAP polypeptide being replaced or deleted can comprise cysteine (or C) 55, 86, 95, 131, 136, 145, 163, 211, 223, or any combination thereof of SEQ ID NO: 1. In some cases, a lysine residue of an MTAP polypeptide being substituted or deleted can comprise C96, C136, or C223 or any combination thereof of SEQ ID NO: 1. In some cases, a cysteine residue of an MTAP polypeptide can be substituted with any one of canonical amino acids comprising alanine, arginine, asparagine, aspartic acid, glutamine, glutamic acid, glycine, histidine, isoleucine, leucine, lysine, methionine, phenylalanine, proline, serine, threonine, tryptophan, tyrosine, valine, or derivatives herein and thereof. In other cases, a cysteine of an MTAP polypeptide can be substituted with any natural or non-natural amino acid residue or any derivative herein and thereof. In some cases, a cysteine of an MTAP polypeptide can be substituted with an arginine.

In some embodiments, an MTAP polypeptide can comprise a mutation corresponding to a K225R mutation of SEQ ID NO: 1. In some instances, an MTAP polypeptide with a K225R mutation can comprise the sequence or a portion thereof of SEQ ID NO: 3.

In some cases, an MTAP polypeptide can comprise sequence having about, at least 60%, 65%, 70%, 75%, 80%, 85%, 90%, 95%, 96%, 97%, 98%, 99% or 100% identity (or any range derivable therein) to SEQ ID NO: 3 or a portion thereof. In some embodiments, an MTAP polypeptide can comprise at least or up to about 10, 20, 30, 40, 50, 60, 70, 80, 90, 100, 110, 120, 130, 140, 150, 160, 170, 180, 190, 200, 210, 220, 230, 240, 250, 260, 270, 280, or 284 residues of SEQ ID NO: 3. In some cases, an MTAP polypeptide can comprise 1-10, 5-15, 10-20, 15-25, 20-30, 25-35, 30-40, 35-45, 40-50, 45-55, 50-60, 55-65, 60-70, 65-75, 70-80, 75-85, 80-90, 85-95, 90-100, 95-105, 100-110, 105-115, 110-120, 115-125, 120-130, 125-135, 130-140, 135-145, 140-150, 145-155, 150-160, 155-165, 160-170, 165-175, 170-180, 175-185, 180-190, 185-195, 190-200, 195-205, 200-210, 205-215, 210-220, 215-225, 220-230, 225-235, 230-240, 235-245, 240-250, 245-255, 250-260, 255-265, 260-270, 265-275, 270-280, or 275-284 residues of SEQ ID NO: 3. In some cases, an MTAP polypeptide can comprise sequence having about at least 80% identity to at least 200 amino acids of SEQ ID NO: 3. In some cases, an MTAP polypeptide can comprise sequence having about at least 80% identity to at least 200 amino acids of SEQ ID NO: 3 and Thr18, Thr197, Ser178, Val233 and Met196 of SEQ ID NO: 3.

In some embodiments, an MTAP polypeptide can comprise a mutation corresponding to a K238R mutation of SEQ ID NO: 1. In some instances, an MTAP polypeptide with a K238R mutation can comprise the sequence or a portion thereof of SEQ ID NO: 5.

In some cases, an MTAP polypeptide can comprise sequence having about, at least 60%, 65%, 70%, 75%, 80%, 85%, 90%, 95%, 96%, 97%, 98%, 99% or 100% identity (or any range derivable therein) to SEQ ID NO: 5 or a portion thereof. In some embodiments, an MTAP polypeptide can comprise at least or up to about 10, 20, 30, 40, 50, 60, 70, 80, 90, 100, 110, 120, 130, 140, 150, 160, 170, 180, 190, 200, 210, 220, 230, 240, 250, 260, 270, 280, or 284 residues of SEQ ID NO: 5. In some cases, an MTAP polypeptide can comprise 1-10, 5-15, 10-20, 15-25, 20-30, 25-35, 30-40, 35-45, 40-50, 45-55, 50-60, 55-65, 60-70, 65-75, 70-80, 75-85, 80-90, 85-95, 90-100, 95-105, 100-110, 105-115, 110-120, 115-125, 120-130, 125-135, 130-140, 135-145, 140-150, 145-155, 150-160, 155-165, 160-170, 165-175, 170-180, 175-185, 180-190, 185-195, 190-200, 195-205, 200-210, 205-215, 210-220, 215-225, 220-230, 225-235, 230-240, 235-245, 240-250, 245-255, 250-260, 255-265, 260-270, 265-275, 270-280, or 275-284 residues of SEQ ID NO: 5. In some cases, an MTAP polypeptide can comprise sequence having about at least 80% identity to at least 200 amino acids of SEQ ID NO: 5. In some cases, an MTAP polypeptide can comprise sequence having about at least 80% identity to at least 200 amino acids of SEQ ID NO: 5 and Thr18, Thr197, Ser178, Val233 and Met196 of SEQ ID NO: 5.

In some instances, a measurement of the methylthioadenosine phosphorylase activity of any MTAP or MTAN polypeptides described herein and thereof can comprise measuring the $V_0$, $V_{max}$, $K_M$, $k_{cat}$, or a combination thereof of the MTAP polypeptides. In some cases, the measurement can comprise an in vitro reaction. In other cases, the measurement can comprise an in vivo reaction.

In some instances, a PEGylated or non-PEGylated wildtype or variant MTAP polypeptide or a PEGylated or non-PEGylated MTAP polypeptide with a K225R mutation or K238R mutation can have a $k_{cat}/K_M$ for MTA or ADO of at least about $1 \times 10^4$ $M^{-1}s^{-1}$ $2 \times 10^4$ $M^{-1}s^{-1}$, $3 \times 10^4$ $M^{-1}s^{-1}$ $4 \times 10^4$ $M^{-1}s^{-1}$, $5 \times 10^4$ $M^{-1}s^{-1}$, $6 \times 10^4$ $M^{-1}s^{-1}$, $7 \times 10^4$ $M^{-1}s^{-1}$, $8 \times 10^4$ $M^{-1}s^{-1}$, $9 \times 10^4$ $M^{-1}s^{-1}$, $1 \times 10^5$ $M^{-1}s^{-1}$, $1.1 \times 10^5$ $M^{-1}s^{-1}$, $1.2 \times 10^5$ $M^{-1}s^{-1}$, $1.3 \times 10^5$ $M^{-1}s^{-1}$, $1.4 \times 10^5$ $M^{-1}s^{-1}$, $1.5 \times 10^5$ $M^{-1}s^{-1}$, $1.6 \times 10^5$ $M^{-1}s^{-1}$, $1.7 \times 10^5$ $M^{-1}s^{-1}$, $1.8 \times 10^5$ $M^{-1}s^{-1}$, $1.9 \times 10^5$ $M^{-1}s^{-1}$, $2 \times 10^5$, $2.1 \times 10^5$ $M^{-1}s^{-1}$, $2.2 \times 10^5$ $M^{-1}s^{-1}$, $2.3 \times 10^5$ $M^{-1}s^{-1}$, $2.4 \times 10^5$ $M^{-1}s^{-1}$, $2.5 \times 10^5$ $M^{-1}s^{-1}$, $2.6 \times 10^5$ $M^{-1}s^{-1}$, $2.7 \times 10^5$ $M^{-1}s^{-1}$, $2.8 \times 10^5$ $M^{-1}s^{-1}$, $2.9 \times 10^5$ $M^{-1}s^{-1}$, $3 \times 10^5$ $M^{-1}s^{-1}$, $3.1 \times 10^5$ $M^{-1}s^{-1}$, $3.2 \times 10^5$ $M^{-1}s^{-1}$, $3.3 \times 10^5$ $M^{-1}s^{-1}$, $3.4 \times 10^5$ $M^{-1}s^{-1}$, $3.5 \times 10^5$ $M^{-1}s^{-1}$, $3.6 \times 10^5$ $M^{-1}s^{-1}$, $3.7 \times 10^5$ $M^{-1}s^{-1}$, $3.8 \times 10^5$ $M^{-1}s^{-1}$, $3.9 \times 10^5$ $M^{-1}s^{-1}$, $4 \times 10^5$ $M^{-1}s^{-1}$, $4.1 \times 10^5$ $M^{-1}s^{-1}$, $4.2 \times 10^5$ $M^{-1}s^{-1}$, $4.3 \times 10^5$ $M^{-1}s^{-1}$, $4.4 \times 10^5$ $M^{-1}s^{-1}$, $4.5 \times 10^5$ $M^{-1}s^{-1}$, $4.6 \times 10^5$ $M^{-1}s^{-1}$, $4.7 \times 10^5$ $M^{-1}s^{-1}$, $4.8 \times 10^5$ $M^{-1}s^{-1}$, $4.9 \times 10^5$ $M^{-1}s^{-1}$, $5 \times 10^5$ $M^{-1}s^{-1}$, $6 \times 10^5$ $M^{-1}s^{-1}$, $7 \times 10^5$ $M^{-1}s^{-1}$, $8 \times 10^5$ $M^{-1}s^{-1}$, $9 \times 10^5$ $M^{-1}s^{-1}$, $1 \times 10^6$ $M^{-1}s^{-1}$, $2 \times 10^6$ $M^{-1}s^{-1}$, $3 \times 10^6$ $M^{-1}s^{-1}$, $4 \times 10^6$ $M^{-1}s^{-1}$, or $5 \times 10^6$ $M^{-1}s^{-1}$. In some cases, a PEGylated or non-PEGylated wildtype or variant MTAP polypeptide or a PEGylated or non-PEGylated MTAP polypeptide with a K225R mutation or K238R mutation can have a $k_{cat}/K_M$ for MTA or ADO from $1 \times 10^4$ to $2 \times 10^4$ $M^{-1}s^{-1}$, from $1.5 \times 10^4$ to $2.5 \times 10^4$ $M^{-1}s^{-1}$, from $2 \times 10^4$ to $3 \times 10^4$ $M^{-1}s^{-1}$, from $2.5 \times 10^4$ to $3.5 \times 10^4$ $M^{-1}s^{-1}$, from $3 \times 10^4$ to $4 \times 10^4$ $M^{-1}s^{-1}$, from $3.5 \times 10^4$ to $4.5 \times 10^4$ $M^{-1}s^{-1}$, from $4 \times 10^4$ to $5 \times 10^4$ $M^{-1}s^{-1}$, from $4.5 \times 10^4$ to $5.5 \times 10^4$ $M^{-1}s^{-1}$, from $5 \times 10^4$ to $6 \times 10^4$ $M^{-1}s^{-1}$, from $5.5 \times 10^4$ to $6.5 \times 10^4$ $M^{-1}s^{-1}$, from $6 \times 10^4$ to $7 \times 10^4$ $M^{-1}s^{-1}$, from $6.5 \times 10^4$ to $7.5 \times 10^4$ $M^{-1}s^{-1}$, from $7 \times 10^4$ to $8 \times 10^4$ $M^{-1}s^{-1}$, from $7.5 \times 10^4$ to $8.5 \times 10^4$ $M^{-1}s^{-1}$, from $8 \times 10^4$ to $9 \times 10^4$ $M^{-1}s^{-1}$, from $8.5 \times 10^4$ to $1 \times 10^5$ $M^{-1}s^{-1}$, from $9 \times 10^5$ to $1.1 \times 10^5$ $M^{-1}s^{-1}$, from $1 \times 10^5$ to $1.2 \times 10^5$ $M^{-1}s^{-1}$, from $1.1 \times 10^5$ to $1.3 \times 10^5$ $M^{-1}s^{-1}$, from $1.2 \times 10^5$ to $1.4 \times 10^5$ $M^{-1}s^{-1}$, from $1.3 \times 10^5$ to $1.5 \times 10^5$ $M^{-1}s^{-1}$, from $1.4 \times 10^5$ to $1.6 \times 10^5$ $M^{-1}s^{-1}$, from $1.5 \times 10^5$ to $1.7 \times 10^5$ $M^{-1}s^{-1}$, from $1.6 \times 10^5$ to $1.8 \times 10^5$ $M^{-1}s^{-1}$, from $1.7 \times 10^5$ to $1.9 \times 10^5$ $M^{-1}s^{-1}$, from $1.8 \times 10^5$ to $2 \times 10^5$ $M^{-1}s^{-1}$, from $1.9 \times 10^5$ to $2.1 \times 10^5$ $M^{-1}s^{-1}$, from $2 \times 10^5$ to $2.2 \times 10^5$ $M^{-1}s^{-1}$, from $2.1 \times 10^5$ to $2.3 \times 10^5$ $M^{-1}s^{-1}$, from $2.2 \times 10^5$ to $2.4 \times 10^5$ $M^{-1}s^{-1}$, from $2.3 \times 10^5$ to $2.5 \times 10^5$ $M^{-1}s^{-1}$, from $2.4 \times 10^5$ to $2.6 \times 10^5$ $M^{-1}s^{-1}$, from $2.5 \times 10^5$ to $2.7 \times 10^5$ $M^{-1}s^{-1}$, from $2.6 \times 10^5$ to $2.8 \times 10^5$ $M^{-1}s^{-1}$, from $2.7 \times 10^5$ to $2.9 \times 10^5$ $M^{-1}s^{-1}$, from $2.8 \times 10^5$ to $3 \times 10^5$ $M^{-1}s^{-1}$, from $2.9 \times 10^5$ to $3.1 \times 10^5$ $M^{-1}s^{-1}$, from $3 \times 10^5$ to $3.2 \times 10^5$ $M^{-1}s^{-1}$, from $3.1 \times 10^5$ to $3.3 \times 10^5$ $M^{-1}s^{-1}$, from $3.2 \times 10^5$ to $3.4 \times 10^5$ $M^{-1}s^{-1}$, from $3.3 \times 10^5$ to $3.5 \times 10^5$ $M^{-1}s^{-1}$, from $3.4 \times 10^5$ to $3.6 \times 10^5$ $M^{-1}s^{-1}$, from $3.5 \times 10^5$ to $3.7 \times 10^5$ $M^{-1}s^{-1}$, from $3.6 \times 10^5$ to $3.8 \times 10^5$ $M^{-1}s^{-1}$, from $3.7 \times 10^5$ to $3.9 \times 10^5$ $M^{-1}s^{-1}$, from $3.8 \times 10^5$ to $4 \times 10^5$ $M^{-1}s^{-1}$, from $3.9 \times 10^5$ to $4.1 \times 10^5$ $M^{-1}s^{-1}$, from $4 \times 10^5$ to $4.2 \times 10^5$ $M^{-1}s^{-1}$, from $4.1 \times 10^5$ to $4.3 \times 10^5$ $M^{-1}s^{-1}$, from $4.2 \times 10^5$ to $4.4 \times 10^5$ $M^{-1}s^{-1}$, from $4.3 \times 10^5$ to $4.5 \times 10^5$ $M^{-1}s^{-1}$, from $4.4 \times 10^5$ to $4.6 \times 10^5$ $M^{-1}s^{-1}$, from $4.5 \times 10^5$ to $4.7 \times 10^5$ $M^{-1}s^{-1}$, from $4.6 \times 10^5$ to $4.8 \times 10^5$ $M^{-1}s^{-1}$, from $4.7 \times 10^5$ to $4.9 \times 10^5$ $M^{-1}s^{-1}$, from $4.8 \times 10^5$ to $5 \times 10^5$ $M^{-1}s^{-1}$. In some instances, a PEGylated or non-PEGylated wildtype or variant MTAP polypeptide or a PEGylated or non-PEGylated MTAP polypeptide with a K225R mutation or K238R mutation can have a $k_{cat}/K_M$ for MTA or ADO from about $1.9 \times 10^5$ to about $2.3 \times 10^5$ $M^{-1}s^{-1}$. In some cases, In some cases, a PEGylated or non-PEGylated wildtype or variant MTAP polypeptide or a PEGylated or non-PEGylated MTAP polypeptide with a K225R mutation or K238R mutation can have a $k_{cat}/K_M$ for MTA or ADO of about $1.9 \times 10^5$ $M^{-1}s^{-1}$. In some instances, a PEGylated or non-PEGylated wildtype or variant MTAP polypeptide or a PEGylated or non-PEGylated MTAP polypeptide with a K225R mutation or K238R mutation can have a $k_{cat}/K_M$ for MTA or ADO of about $2.3 \times 10^5$ $M^{-1}s^{-1}$. In some instances, a PEGylated or non-PEGylated wildtype or variant MTAP polypeptide or a PEGylated or non-PEGylated MTAP polypeptide with a K225R mutation or K238R mutation can have a $k_{cat}/K_M$ for MTA or ADO from about $1.5 \times 10^5$ to about $3 \times 10^5$ $M^{-1}s^{-1}$. In some cases, In some cases, a PEGylated or non-PEGylated wildtype or variant MTAP polypeptide or a PEGylated or non-PEGylated MTAP polypeptide with a K225R mutation or K238R mutation can have a $k_{cat}/K_M$ for MTA or ADO of at least about $1.5 \times 10^5$ $M^{-1}s^{-1}$. In some instances, a PEGylated or non-PEGylated wildtype or variant MTAP polypeptide or a PEGylated or non-PEGylated MTAP polypeptide with a K225R mutation or K238R mutation can have a $k_{cat}/K_M$ for MTA or ADO of about $3 \times 10^5$ $M^{-1}s^{-1}$.

In some instances, the methylthioadenosine phosphorylase activity of a PEGylated or non-PEGylated MTAP polypeptide with a K225R mutation or K238R mutation or a PEGylated or non-PEGylated MTAP polypeptide with a lysine or cysteine mutation can have a $V_{max}$ of at least 30%, 40%, 50%, 60%, 70%, 80%, 90%, or 100% of that of a PEGylated or non-PEGylated MTAP polypeptide comprising SEQ ID NO: 1. In some instances, the methylthioadenosine phosphorylase activity of a PEGylated or non-PEGylated MTAP polypeptide with a K225R mutation or K238R mutation or a PEGylated or non-PEGylated MTAP polypeptide with a lysine or cysteine mutation can have a $V_{max}$ from 30 to 50%, from 40 to 60%, from 50 to 70%, from 60 to 80%, from 70 to 90%, or from 80 to 100% of that of a PEGylated or non-PEGylated MTAP polypeptide comprising SEQ ID NO: 1. In some instances, the methylthioadenosine phosphorylase activity of a PEGylated or non-PEGylated MTAP polypeptide with a K225R mutation or K238R mutation or a PEGylated or non-PEGylated MTAP polypeptide with a lysine or cysteine mutation can have a $V_{max}$ at least 50% of that of a PEGylated or non-PEGylated MTAP polypeptide comprising SEQ ID NO: 1.

In some instances, the methylthioadenosine phosphorylase activity of a PEGylated or non-PEGylated MTAP polypeptide with a K225R mutation or K238R mutation or a PEGylated or non-PEGylated MTAP polypeptide with a lysine or cysteine mutation can have a $k_{cat}/K_M$ of at least 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, or 200% of that of a PEGylated or non-PEGylated MTAP polypeptide comprising SEQ ID NO: 1. In some instances, the methylthioadenosine phosphorylase activity of a PEGylated or non-PEGylated MTAP polypeptide with a K225R mutation or K238R mutation or a PEGylated or non-PEGylated MTAP polypeptide with a lysine or cysteine mutation can have a $K_M$ from 30 to 50%, from 40 to 60%, from 50 to 70%, from 60 to 80%, from 70 to 90%, from 80 to 100%, from 90 to 110%, from 100 to 150%, from 120 to 180%, from 150 to 200%, from 170 to 220%, from 200 to 250%, from 220 to 270%, from 250 to 350%, from 300 to 400%, from 350 to 450%, or from 400 to 500% of that of a PEGylated or non-PEGylated MTAP polypeptide comprising SEQ ID NO: 1. In some instances, the methylthioadenosine phosphorylase activity of a PEGylated or non-PEGylated MTAP polypeptide with a K225R mutation or K238R mutation or a PEGylated or non-PEGylated MTAP polypeptide with a lysine or cysteine mutation can have a $K_M$ no more than twice, or 200%, of that of a PEGylated or non-PEGylated MTAP polypeptide comprising SEQ ID NO: 1.

In some instances, the methylthioadenosine phosphorylase activity of a PEGylated or non-PEGylated MTAP polypeptide with a K225R mutation or K238R mutation or a PEGylated or non-PEGylated MTAP polypeptide with a lysine or cysteine mutation can have a $k_{cat}$ 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 910%, 920%, 930%, 940%, 950%, 960%, 970%, 980%, 990%, or 1000% of that of a PEGylated or non-PEGylated MTAP polypeptide comprising SEQ ID NO: 1. In some instances, the methylthioadenosine phosphorylase activity of a PEGylated or non-PEGylated MTAP polypeptide with a K225R mutation or K238R mutation or a PEGylated or non-PEGylated MTAP polypeptide with a lysine or cysteine mutation can have a $k_{cat}$ from 30 to 50%, from 40 to 60%, from 50 to 70%, from 60 to 80%, from 70 to 90%, from 80 to 100%, from 90 to 110%, from 100 to 150%, from 120 to 180%, from 150 to 200%, from 170 to 220%, from 200 to 250%, from 220 to 270%, from 250 to 350%, from 300 to 400%, from 350 to 450%, from 400 to 500%, from 450 to 550%, from 500 to 600%, from 550 to 650%, from 600 to 700%, from 650 to 750%, from 700 to 800%, from 750 to 850%, from 800 to 900%, from 850 to 950%, or from 900 to 1,000% of that of a PEGylated or non-PEGylated MTAP polypeptide comprising SEQ ID NO: 1. In some instances, the methylthioadenosine phosphorylase activity of a PEGylated or non-PEGylated MTAP polypeptide with a K225R mutation or K238R mutation or a PEGylated or non-PEGylated MTAP polypeptide with a lysine or cysteine mutation can have a $k_{cat}$ at least 50% of that of a PEGylated or non-PEGylated MTAP polypeptide comprising SEQ ID NO: 1.

In some instances, the methylthioadenosine phosphorylase activity of a PEGylated or non-PEGylated MTAP polypeptide with a K225R mutation or K238R mutation or a PEGylated or non-PEGylated MTAP polypeptide with a lysine or cysteine mutation can have a $k_{cat}/K_M$ 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 910%, 920%, 930%, 940%, 950%, 960%, 970%, 980%, 990%, or 1000% of that of a PEGylated or non-PEGylated MTAP polypeptide comprising SEQ ID NO: 1. In some instances, the methylthioadenosine phosphorylase activity of a PEGylated or non-PEGylated MTAP polypeptide with a K225R mutation or K238R mutation or a PEGylated or non-PEGylated MTAP polypeptide with a lysine or cysteine mutation can have a $k_{cat}/K_M$ from 30 to 50%, from 40 to 60%, from 50 to 70%, from 60 to 80%, from 70 to 90%, from 80 to 100%, from 90 to 110%, from 100 to 150%, from 120 to 180%, from 150 to 200%, from 170 to 220%, from 200 to 250%, from 220 to 270%, from 250 to 350%, from 300 to 400%, from 350 to 450%, from 400 to 500%, from 450 to 550%, from 500 to 600%, from 550 to 650%, from 600 to 700%, from 650 to 750%, from 700 to 800%, from 750 to 850%, from 800 to 900%, from 850 to 950%, or from 900 to 1,000% of that of a PEGylated or non-PEGylated MTAP polypeptide comprising SEQ ID NO: 1. In some instances, the methylthioadenosine phosphorylase activity of a PEGylated or non-PEGylated MTAP polypeptide with a K225R mutation or K238R mutation or a PEGylated or non-PEGylated MTAP polypeptide with a lysine or cysteine mutation can have a $k_{cat}/K_M$ at least 50% of that of a PEGylated or non-PEGylated MTAP polypeptide comprising SEQ ID NO: 1.

In some cases, PEGylation of an MTAP polypeptide does not alter the secondary or tertiary structure of the MTAP polypeptide. In other cases, PEGylation of an MTAP polypeptide can alter the secondary or tertiary structure of the MTAP polypeptide, without affecting MTAP activity. In some instances, PEGylation of an MTAP polypeptide may alter the molecular size, charge, or receptor-binding capabilities of the MTAP polypeptide. In some cases, PEGylation of an MTAP polypeptide can reduce clearance of the MTAP polypeptide by the reticuloendothelial system (RES), kidney, spleen, or liver. In some cases, PEGylation of an MTAP polypeptide can increase the circulatory time of the MTAP polypeptide. In some cases, PEGylation of an MTAP polypeptide can create a steric hindrance, mask, or shield of the MTAP polypeptide that prevent its access by an enzyme or protein. In some cases, a steric hindrance, mask, or shield can also decrease the immunogenicity or antigenicity of the MTAP polypeptide. In other cases, a PEG molecule for PEGylation of an MTAP polypeptide can comprise a hydrophilic, flexible, and biocompatible spacer. In other instances, a PEG molecule for PEGylation of an MTAP polypeptide can also comprise maleimide, vinyl sulfones, pyridyl disulfide, amine, carboxylic acids, or NHS esters.

In some cases, PEGylation of an MTAP polypeptide can modulate the serum half-life of the MTAP polypeptide. In other cases, PEGylation of an MTAP polypeptide can increase the serum half-life of the MTAP polypeptide.

PEGylation of an MTase, in some cases, can increase the hydrodynamic radius of the enzyme and hence increase the serum persistence. In certain aspects, the disclosed polypeptide may be conjugated to any targeting agent, such as a ligand having the ability to specifically and stably bind to an external receptor or binding site on a target cell (e.g., U.S. Patent Publ. 2009/0304666).

In some embodiments, PEGylation of an MTAP polypeptide can increase the hydrodynamic radius of the MTAP polypeptide by at least about 30%, 40%, 50%, 60%, 70%, 80%, 90%, 100%, 120%, 140%, 160%, 180%, 200%, 250%, 300%, 350%, 400%, 500%, 600%, 700%, 800%, 900%, or 1000%. In some instances, PEGylation of an MTAP polypeptide can increase the hydrodynamic radius of the MTAP polypeptide by an amount from 30 to 50%, from 40 to 60%, from 50 to 70%, from 60 to 80%, from 70 to 90%, from 80 to 100%, from 90 to 110%, from 100 to 150%, from 120 to 180%, from 150 to 200%, from 170 to 220%, from 200 to 250%, from 220 to 270%, from 250 to 350%, from 300 to 400%, from 350 to 450%, from 400 to 500%, from 450 to 550%, from 500 to 600%, from 550 to 650%, from 600 to 700%, from 650 to 750%, from 700 to 800%, from 750 to 850%, from 800 to 900%, from 850 to 950%, or from 900 to 1,000%.

In some embodiments, a PEGylated MTAP polypeptide can have a serum half-life of at least about 1 hours, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, 49 hours, 50 hours, 51 hours, 52 hours, 53 hours, 54 hours, 55 hours, 56 hours, 57 hours, 58 hours, 59 hours, 60 hours, 61 hours, 62 hours, 63 hours, 64 hours, 65 hours, 66 hours, 67 hours, 68 hours, 69 hours, 70 hours, 71 hours, 72 hours, 84 hours, 96 hours, 108 hours, 120 hours, 132 hours, 144 hours, 156 hours, 168 hours, 180 hours, 190 hours, or 200 hours. In other cases, In some embodiments, a PEGylated MTAP polypeptide can have a serum half-life of from 1 to 5 hours, from 2 to 6 hours, from 3 to 7 hours, from 4 to 8 hours, from 5 to 9 hours, from 6 to 10 hours, from 7 to 11 hours, from 8 to 12 hours, from 9 to 13 hours, from 10 to 14 hours, from 11 to 15 hours, from 12 to 16 hours, from 13 to 17 hours, from 14 to 18 hours, from 12 to 24 hours, from 18 to 30 hours, from 24 to 36 hours, from 30 to 42 hours, from 36 to 48 hours, from 42 to 46 hours, from 43 to 47 hours, from 44 to 48 hours, from 45 to 49 hours, from 46 to 50 hours, from 47 to 51 hours, from 48 to 52 hours, from 49 to 53 hours, from 50 to 54 hours, from 51 to 55 hours, from 52 to 56 hours, from 53 to 57 hours, from 54 to 58 hours, from 55 to 59 hours, from 56 to 60 hours, from 57 to 61 hours, from 58 to 62 hours, from 59 to 63 hours, from 60 to 64 hours, from 61 to 65 hours, from 62 to 66 hours, from 63 to 67 hours, from 64 to 68 hours, from 65 to 69 hours, from 66 to 70 hours, from 67 to 71 hours, from 68 to 72 hours, from 66 to 78 hours, from 72 to 84 hours, from 78 to 90 hours, from 84 to 96 hours, from 90 to 102 hours, from 96 to 108 hours, from 102 to 114 hours, from 108 to 120 hours, from 114 to 126 hours, from 120 to 132 hours, from 126 to 138 hours, from 132 to 144 hours, from 138 to 150 hours, from 144 to 156 hours, from 150 to 162 hours, from 156 to 168 hours, from 162 to 174 hours, from 168 to 180 hours, from 174 to 186 hours, from 180 to 192 hours, from 186 to 198 hours, or from 192 to 204 hours. In other cases, a PEGylated polypeptide can have a serum half-life of at least or about 57 hours. In other cases, a PEGylated polypeptide can have a serum half-life of at least or about 36 hours.

In some instances, a PEGylated MTAP polypeptide can have a serum half-life of at least about 10%, 20%, 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, or 1000% longer than that of an MTAP polypeptide not PEGylated. In some instances, a PEGylated MTAP polypeptide can have a serum half-life from 10 to 100%, from 50 to 150%, from 100 to 200%, from 150 to 250%, from 200 to 300%, from 250 to 350%, from 300 to 400%, from 350 to 450%, from 400 to 500%, from 450 to 550%, from 500 to 600%, from 550 to 650%, from 600 to 700%, from 650 to 750%, from 700 to 800%, from 750 to 850%, from 800 to 900%, from 850 to 950%, or from 900 to 1000%, longer than that of an MTAP polypeptide not PEGylated.

In some instances, a PEGylated MTAP polypeptide can have an extracellular half-life of at least about 10%, 20%, 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000% longer than that of an MTAP polypeptide not PEGylated. In some instances, a PEGylated MTAP polypeptide can have an extracellular half-life from 10 to 100%, from 50 to 150%, from 100 to 200%, from 150 to 250%, from 200 to 300%, from 250 to 350%, from 300 to 400%, from 350 to 450%, from 400 to 500%, from 450 to 550%, from 500 to 600%, from 550 to 650%, from 600 to 700%, from 650 to 750%, from 700 to 800%, from 750 to 850%, from 800 to 900%, from 850 to 950%, or from 900 to 1000%, longer than that of an MTAP polypeptide not PEGylated.

In some cases, an MTAP polypeptide comprising a lysine substitution or deletion can allow the MTAP to be maximally PEGylated without decreasing the methylthioadenosine phosphorylase activity of the MTAP polypeptide by more than 10%, 20%, 30%, 40% or 50%. In some cases, an MTAP polypeptide comprising a K225R substitution, a K238R substitution, a structural equivalent thereof, or a combination thereof can allow the MTAP to be maximally PEGylated without decreasing its methylthioadenosine phosphorylase activity level compared to that of a non-PEGylated MTAP polypeptide by more than 10%, 20%, 30%, 40% or 50%. In some cases, an MTAP polypeptide comprising a K225R substitution, a K238R substitution, a structural equivalent thereof, or a combination thereof can allow the MTAP to be maximally PEGylated and prevent the MTAP polypeptide from decreasing its methylthioadenosine phosphorylase activity compared to that of a non-PEGylated MTAP polypeptide. In some cases, an MTAP polypeptide comprising a K225R substitution, a K238R substitution, a structural equivalent thereof, or a combination thereof can increase its methylthioadenosine phosphorylase activity compared to that of a non-PEGylated MTAP polypeptide. In some instances, measuring an methylthioadenosine phosphorylase activity of the MTAP polypeptide can comprise measuring the MTA or ADO-degrading activity. In some cases, the MTA or ADO-degrading activity can be measured by any assay to detect the products resulting from the degradation of MTA or ADO, such as the detection of adenine. In some cases, the MTA or ADO-degrading activity can be measured by any assay to detect the amount of products resulting from the degradation of MTA or ADO, such as the detection of adenine, methylthioribose-phosphate, methylthioribose, or S-methyl-5-thio-α-D-ribose 1-phosphate. In some cases, the MTA or ADO-degrading activity can be measured by any assay to detect the amount of substrates in the degradation of MTA or ADO comprising MTA, ADO, or S-methyl-5'thioadenosine. In other cases, the MTA or ADO-degrading activity can be measured by any assay to detect the inhibitory level of an MTAP polypeptide by inhibitors comprising methylthiotubercin or 5'-chloroformycin.

In some cases, a modification of an MTAP polypeptide can create, induce, or modify to arise or include a desired property for the MTAP polypeptide. In some cases, a desired property can comprise an increase in enzymatic activity or polypeptide abundance of the MTAP polypeptide. In some instances, an MTAP polypeptide can have a modification to modulate its methylthioadenosine phosphorylase activity. Such a modulation can comprise an increase or decrease the methylthioadenosine phosphorylase activity. In some cases, a modification can comprise an increase in expression or stability of an MTAP polypeptide. In some cases, a modification can comprise removing a sequence or structure that can elicit an immune response against an MTAP polypeptide. In other cases, a modification can comprise addition, deletion, or substitution of amino acid residues of an MTAP polypeptide.

In some instances, a modification may comprise a deletion, insertion, or substitution of a nucleotide in a nucleic acid encoding an MTAP polypeptide without affecting the amino acid of the MTAP polypeptide. Such a modification can comprise a modification in the 5' or 3' UTR of a transcript of a nucleic acid encoding an MTAP polypeptide. In some cases, a modification can also comprise any non-coding sequence of a transcript of a nucleic acid encoding an MTAP polypeptide, such as for example, an intron sequence. In other cases, a modification can also comprise a modification in the coding region of a transcript of a nucleic acid encoding an MTAP polypeptide.

In some cases, such amino acid residues can comprise an active site described herein or thereof. In other cases, other residues can also be identified based on structural analysis, homology analysis, or computational prediction. In other cases, a population of polypeptides with different modifications sites may be generated. In some instances, mutant polypeptides with increased MTA and/or ADO-degrading activity may be selected from the mutant population. Selection of desired mutants may include methods for measurement of the methylthioadenosine phosphorylase activity described herein and thereof. In some instances, mutant polypeptides with any desired property described herein and thereof can be selected. In some cases, an MTAP polypeptide can comprise a heterologous peptide or chemical modification. A heterologous polypeptide can comprise any such polypeptides described herein and thereof. In some cases, an MTAP polypeptide can comprise a chemical reaction described herein and thereof.

A PEGylated MTAP polypeptide, in some cases, can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or more PEG molecules. In some instances, a PEGylated MTAP polypeptide can comprise from 1 to 10, from 2 to 11, from 3 to 12, from 4 to 13, from 5 to 14, from 6 to 15, from 7 to 16, from 8 to 17, from 9 to 18, from 10 to 19, from 11 to 20, from 12 to 21, from 13 to 22, from 14 to 23, from 15 to 24, from 16 to 25, from 17 to 26, from 18 to 27, from 19 to 28, from 20 to 29, from 21 to 30, from 22 to 31, from 23 to 32, from 24 to 33, from 25 to 34, from 26 to 35 PEG molecules. In some cases, the number of PEG molecules conjugated to an MTAP polypeptide can follow a Gaussian distribution. In some cases, a PEGylated MTAP polypeptide can have about 80% probability to be conjugated to 1, 2, 3, 4, or 5 PEG molecules. In some cases, a PEGylated MTAP polypeptide can have about 20% probability to be conjugated to 0, 6, 7, or 8 PEG molecules. In other cases, a PEGylated MTAP polypeptide can have about 20% probability to be conjugated to 0, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more PEG molecules. In some cases, a PEGylated MTAP polypeptide can have about 1% probability to be conjugated to more than 8 PEG molecules. In some cases, the mode of the number of PEG molecules conjugated to an MTAP polypeptide can comprise 1±1, 2±1, 3±1, 4±1, 5±1, 6±1, 7±1, 8±1, 9±1, 10±1, 1±2, 2±2, 3±2, 4±2, 5±2, 6±2, 7±2, 8±2, 9±2, 10±2, 1±3, 2±3, 3±3, 4±3, 5±3, 6±3, 7±3, 8±3, 9±3, or 10±3. In some cases, the mode of the number of PEG molecules conjugated to an MTAP polypeptide can comprise 2±1, 3±1, 4±1, or 6±1. In some cases, the mode of the number of PEG molecules conjugated to an MTAP polypeptide can comprise 8±3.

In some instances, said polyethylene glycol has an average molecular weight of about 500 kDa to about 1000 kDa, about 800 kDa to about 1600 kDa, about 1500 kDa to about 3000 kDa, about 2000 kDa to about 4000 kDa, about 2500 kDa to about 5000 kDa, about 3000 kDa to about 6000 kDa, about 4,000 kDa to about 8,000 kDa, about 6,000 kDa to about 12,000 kDa, about 10,000 kDa to about 20,000 kDa, or about 15,000 kDa to about 30,000 kDa.

In some instances, PEG may be conjugated to Lys11, Lys32, Lys40, Lys49, Lys51, Lys71, Lys82, Lys147, Lys158, Lys158, Lys166, Lys206, Lys225, Lys238, Lys241, Lys246, Lys248, or Lys271 of SEQ ID NO: 1 or the corresponding position of a homologous MTAP polypeptide with MTAP enzymatic activity, or any combination thereof. In some instances, PEG may be conjugated to Cys55, Cys86, Cys95, Cys131, Cys136, Cys145, Cys211, or Cys223 of SEQ ID NO: 1 or the corresponding position of a homologous MTAP polypeptide with MTAP enzymatic activity, or any combination thereof.

In some instances, a PEGylated MTAP polypeptide can have a catalytic efficiency for MTA or ADO ($k_{cat}/K_M$) of at least or about 1×10^3, 2×10^3, 3×10^3, 4×10^3, 5×10^3, 6×10^3, 7×10^3, 8×10^3, 9×10^3, 1×10^4, 2×10^4, 3×10^4, 4×10^4, 5×10^4, 6×10^4, 7×10^4, 8×10^4, 9×10^4, 1×10^5, 2×10^5, 3×10^5, 4×10^5, 5×10^5, 6×10^5, 7×10^5, 8×10^5, 9×10^5, 1×10^6, 2×10^6, 3×10^6, 4×10^6, 5×10^6, 6×10^6, 7×10^6, 8×10^6, 9×10^6, 1×10^7, 2×10^7, 3×10^7, 4×10^7, 5×10^7, 6×10^7, 7×10^7, 8×10^7, 9×10^7, 1×10^8, 2×10^8, 3×10^8, 4×10^8, 5×10^8, 6×10^8, 7×10^8, 8×10^8, or 9×10^8 $s^{-1}M^{-1}$. In some instances, an MTAP polypeptide can have a $k_{cat}/K_M$ for MTA or ADO from 0.5×10^3 to 2×10^3, from 1.5×10^3 to 3×10^3, from 2.5×10^3 to 4×10^3, from 3.5×10^3 to 5×10^3, from 4.5×10^3 to 6×10^3, from 5.5×10^3 to 7×10^3, from 6.5×10^3 to 8×10^3, from 7.5×10^3 to 9×10^3, from 8.5×10^3 to 1×10^4, from 0.5×10^4 to 2×10^4, from 1.5×10^4 to 3×10^4, from 2.5×10^4 to 4×10^4, from 3.5× 10^4 to 5×10^4, from 4.5×10^4 to 6×10^4, from 5.5×10^4 to 7×10^4, from 6.5×10^4 to 8×10^4, from 7.5×10^4 to 9×10^4, from 8.5×10^4 to 1×10^5, from 0.5×10^5 to 2×10^5, from 1.5×10^5 to 3×10^5, from 2.5×10^5 to 4×10^5, from 3.5× 10^5 to 5×10^5, from 4.5×10^5 to 6×10^5, from 5.5×10^5 to 7×10^5, from 6.5×10^5 to 8×10^5, from 7.5×10^5 to 9×10^5, from 8.5×10^5 to 1×10^6, from 0.5×10^6 to 2×10^6, from 1.5×10^6 to 3×10^6, from 2.5×10^6 to 4×10^6, from 3.5× 10^6 to 5×10^6, from 4.5×10^6 to 6×10^6, from 5.5×10^6 to 7×10^6, from 6.5×10^6 to 8×10^6, from 7.5×10^6 to 9×10^6, from 8.5×10^6 to 1×10^7, from 0.5×10^7 to 2×10^7, from 1.5×10^7 to 3×10^7, from 2.5×10^7 to 4×10^7, from 3.5× 10^7 to 5×10^7, from 4.5×10^7 to 6×10^7, from 5.5×10^7 to 7×10^7, from 6.5×10^7 to 8×10^7, from 7.5×10^7 to 9×10^7, from 8.5×10^7 to 1×10^8, from 0.5×10^8 to 2×10^8, from 1.5×10^8 to 3×10^8, from 2.5×10^8 to 4×10^8, from 3.5× 10^8 to 5×10^8, from 4.5×10^8 to 6×10^8, from 5.5×10^8 to 7×10^8, from 6.5×10^8 to 8×10^8, or from 7.5×10^8 to 9×10^8 $s^{-1}M^{-1}$. In some instances, a PEGylated MTAP polypeptide can have a $k_{cat}/K_M$ for MTA or ADO of at least or about 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $1\times10^4$, $1\times10^5$, $1\times10^6$ $s^{-1}M^{-1}$ or any range derivable therein. In some instances, an MTAP polypeptide can have a $k_{cat}/K_M$ for MTA or ADO of at least or about $1\times10^5$ $s^{-1}M^{-1}$.

In some embodiments, PEGylated MTAP or MTAN, when administered in a subject bearing a tumor, can increase the number of T-cells infiltrating a tumor microenvironment (TME) by about 10%, 20%, 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000%, 2000%, 3000%, 4000%, 5000%, 6000%, 7000%, 8000%, 9000%, 10000%, or 20000 of the number of T-cells infiltrating the TME without or before the administration. In some embodiments, a PEGylated MTAP, when administered in a subject bearing a tumor, can increase the number of T-cells infiltrating a TME by 10 to 30%, from 20 to 40%, from 30 to 50%, from 40 to 60%, from 50 to 70%, from 60 to 80%, from 70 to 90%, from 80 to 100%, from 90 to 150%, from 100 to 200%, from 150 to 250%, from 200 to 300%, from 250 to 350%, from 300 to 400%, from 350 to 450%, from 400 to 500%, from 450 to 550%, from 500 to 600%, from 550 to 650%, from 600 to 700%, from 650 to 750%, from 700 to 800%, from 750 to 850%, from 800 to 900%, from 850 to 950%, from 900 to 1000%, from 950 to 2000%, from 1500 to 2500%, from 2000 to 3000%, from 2500 to 3500%, from 3000 to 4000%, from 3500 to 4500%, from 4000 to 5000%, from 4500 to 5500%, from 5000 to 6000%, from 5500 to 6500%, from 6000 to 7000%, from 6500 to 7500%, from 7000 to 8000%, from 7500 to 8500%, from 8000 to 9000%, from 8500 to 9500%, from 9000 to 10000%, or from 9500 to 20000% of the number of T-cells infiltrating the TME without or before the administration.

MTAP in Cancer and Immunosuppression

In some cases, MTAP is a marker for cancer. In some cases, a loss-of-function mutation of MTAP can cause or promote cancer. In other cases, a homozygous genetic deletion of MTAP can cause or promote cancer. In other cases, a homozygous genetic deletion or loss-of-function mutation of MTAP can be associated with poor therapeutic outcome. In some cases, a cancer related to the deletion or loss-of-function of MTAP can comprise osteosarcomas, pancreatic cancers, chordomas, mesothelioma, T-cell acute lymphoblastic leukemias, or gliomas. In some instances, a genetic or non-genetic loss or suppression of MTAP or MTAP's activity can increase cancer cell proliferation. In some instances, a genetic or non-genetic loss or suppression of MTAP or MTAP's activity can increase pro-tumorigenic gene expression in cancer or non-cancer cells. In some instances, a genetic or non-genetic loss or suppression of MTAP or MTAP's activity can increase hepatocellular carcinoma proliferation. In some instances, a genetic or non-genetic loss or suppression of MTAP or MTAP's activity can increase pro-tumorigenic gene expression in hepatic stellate cells.

In some instances, a genetic loss of MTAP can result in an increased secretion of MTA and an accumulation of MTA. In some instances, a loss of the MTAP activity can result in an increased secretion of MTA and an accumulation of MTA. In other instances, a repression of MTAP expression can also result in an increased secretion of MTA and an accumulation of MTA. In some cases, an accumulation of MTA can be extracellular. In other cases, an accumulation of MTA can be intracellular. In other instances, a loss or repression of MTAP in a cancer can cause an accumulation MTA in TME. In some instances, a TME can comprise the environment or surrounding tissues around the tumor comprising non-tumor cells, blood vessels, immune cells, fibroblasts, signaling molecules or the extracellular matrix (ECM). In some cases, a cancer with an accumulation of MTA than normal tissues can have a higher degree of invasiveness and malignancy comparing to a cancer without an accumulation of MTA.

In some cases, a risk of cancer associated with the genetic deletion of the chromosome 9q21.3 can comprise the deletion or loss-of-function of MTAP. In some instances, a deletion of MTAP and a deletion of CDKN2A in a chromosome 9q21.3 can independently contribute to the development of a cancer. In some cases, a heterozygous genetic deletion of MTAP is associated with a T-cell lymphoma. In some cases, mutations within the MTAP gene leading to exon skipping, alternative splicing, or a dysfunctional MTAP polypeptide are associated with cancer independently from CDKN2A mutations. In some cases, the cancer can comprise diaphyseal medullary stenosis with malignant fibrous histiocytoma (DMSMFH).

In some cases, an accumulation of MTA can cause immunosuppression. In some cases, an immunosuppression caused by a genetic or non-genetic loss or suppression of MTAP; an accumulation of MTA; or a combination of both can comprise an inhibition of the proliferation or differentiation of T-cells. In some instances, the immunosuppression can comprise an inhibition of the expansion of antigen-specific CD8+ T-cells. In other cases, the immunosuppression can comprise the inhibition of an upregulated expression of CD25 or CD69 in T-cells. In some cases, the immunosuppression can comprise an induction of apoptosis in pre-stimulated cytotoxic T lymphocytes. In some cases, an accumulation of MTA (e.g., adding exogenous MTA) can also inhibit DNA synthesis, protein synthesis, and proliferation of human lymphocyte cultures stimulated with antigens or allogeneic cells. In some instances, the effect of an MTA accumulation can be reversed by removal of MTA (e.g., washing exogenous MTA). In some cases, MTA can act as an agonist of the adenosine receptors A2a and A2b, creating a tolerogenic phenotype in macrophages. In other cases, MTA can also cause tumor in fibroblasts by an induction of basic fibroblast growth factor (bFGF) and matrix metalloproteinase 3 (MMP3). In some cases, MTA excreted by tumor can allow a tumor cell to evade surveillance and elimination by an immune system. In some cases, MTA can cause an immunosuppression by inhibiting PRMT5 receptor on a T-cell. In some cases, MTA can inhibit PRMT5. In some instances, MTA can inhibit PRMT5 in vitro. In other cases, MTA can inhibit PRMT5 in vivo. In some instances, MTA can inhibit PRMT5 with an inhibitor constant of about 0.26 μM. in some cases, an inhibition of PRMT5 by MTA can reduce T-cell proliferation, viability, or functionality.

In some cases, an accumulation of extracellular ADO by a genetic or non-genetic loss or suppression of MTAP or MTAP's activity can also cause immunosuppression. In some cases, an accumulation of ADO in TME can also cause resistance to anti-PD/LI or anti-CTLA4 antibody. In some cases, ADO can be released by dying cells. In some instances, ADO can bind adenosine receptors. In some instances, ADO can bind G-protein coupled ADO receptors comprising MR, A2A3, A2BR, or A3R. In some cases, ADO can be converted from AMP by CD73. In other cases, AMP can be converted from ADP or ATP by CD39.

Treating Cancer with a PEGylated MTAP Polypeptide

In some cases, a PEGylated MTAP polypeptide can be used to treat cancer. In some instances, a cancer can comprise a genetic deletion of an MTAP gene. In other cases, a cancer can comprise a loss-of-function mutation of an MTAP gene. In some instances, a cancer can comprise a loss of activity of an MTAP polypeptide. In some instances, a cancer can comprise a loss or reduction of activity of an MTAP polypeptide without a genetic mutation of the gene encoding the MTAP polypeptide. In some instances, a cancer can comprise a loss or reduction of activity of an MTAP polypeptide without a genetic mutation of the gene encoding the MTAP polypeptide. In some instances, a cancer can comprise a loss or reduction of methylthioadenosine phosphorylase activity. In some instances, loss or reduction of activity of an MTAP polypeptide or a loss of methylthioadenosine phosphorylase activity can be identified based on a comparison to a reference level.

In some cases, a reference level of activity can comprise a level of activity of a normal or healthy tissue or subject. In some cases, a normal or healthy subject may not comprise a disease or condition that would increase or decrease the activity of an MTAP polypeptide or methylthioadenosine phosphorylase. A normal or healthy subject may be healthy. In other cases, a normal or healthy subject may not have cancer. In some instances, a normal or healthy subject may not have a higher risk to develop cancer when compared to an average subject in a population. In other cases, a reference level of activity in a subject can comprise a level of activity of a normal or healthy tissue in the subject. In other cases, a reference level of activity in a subject can comprise a level of activity of a normal or healthy tissue in another subject. In some cases, a reference level of activity in a tissue can comprise a level of activity in a comparable tissue in a healthy state. In other cases, a reference level of activity in a subject can comprise a level of activity of a normal or healthy tissue in another normal or healthy subject. In some cases, a reference level can also be defined in vitro. In some cases, a reference level of the activity of an MTAP polypeptide or methylthioadenosine phosphorylase can comprise the level of the activity of an MTAP polypeptide or methylthioadenosine phosphorylase of a cell with a wildtype sequence, expression level, or abundance level of the MTAP polypeptide.

In some cases, MTAP expression or activity in a cancer or cancer cell is reduced by at least 10%, 20%, 30%, 40%, 50%, 60%, 70%, 80%, or 90% compared to a reference level.

In some cases, treatment with an MTAP polypeptide or PEG-MTAP reduces the extracellular concentration of MTA in the tumor microenvironment by at least 10%, 20%, 30%, 40%, 50%, 60%, 70%, 80%, or 90% The cancer or cancer cell comprising the MTAP deletion can comprise bladder, brain, breast, heme, colon, lung, pancreas, or skin cancer cell.

In some cases, a reference level can comprise a level in a healthy subject. In other cases, a reference level can comprise a level in a tissue in a healthy subject. In some cases, a reference level can comprise a level in a healthy tissue in a subjected being administered with the pharmaceutical compositions described herein and thereof.

In some embodiments, a PEGylated MTAP polypeptide can have a low immunogenicity risk. In other cases, an MTAP polypeptide can have no low immunogenicity risk.

A cancer, in some instances, can comprise malignant cell type, such as those found in a solid tumor or a hematological tumor. In some case, a cancer can comprise a tumor of an organ selected from the group consisting of pancreas, colon, cecum, stomach, gallbladder, skin, brain, head, neck, ovary, kidney, larynx, sarcoma, lung, bladder, melanoma, prostate, and breast. In some case, a cancer can comprise hematological tumors include tumors of the bone marrow, T or B cell malignancies, leukemias, lymphomas, blastomas, myelomas, and the like. In some case, a cancer can also comprise carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, gallbladder cancer, breast cancer, colon cancer, colorectal cancer, endometrial or uterine carcinoma, salivary gland carcinoma, kidney or renal cancer, renal cell carcinoma, prostate cancer, vulval cancer, thyroid cancer, various types of head and neck cancer, head and neck squamous cell carcinoma, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

In some case, a cancer can comprise neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

Nucleic Acid

In some instances, a nucleic acid encoding an MTAP polypeptide can comprise a DNA, RNA, LNA, PNA, or any derivatives herein and thereof that can encode the MTAP polypeptide. In some cases, a nucleic acid comprising SEQ ID NO: 2 encodes an MTAP polypeptide comprising SEQ ID NO: 1. In some cases, a nucleic acid comprising SEQ ID NO: 4 encodes an MTAP polypeptide comprising SEQ ID NO: 3. In some cases, a nucleic acid comprising SEQ ID NO: 6 encodes an MTAP polypeptide comprising SEQ ID NO: 5.

In some cases, nucleic acids encoding an MTAP polypeptide can also be codon-optimized based on the organism used to express the polypeptide.

PEGylation of an MTAP Polypeptide

In some instances, PEGylation of an MTAP polypeptide can be achieved by incubation of a reactive derivative of PEG with the MTAP polypeptide. In some cases, PEGylation can be covalent. In other cases, PEGylation can be non-covalent. In some instances, PEGylation of an MTAP polypeptide can mean an MTAP polypeptide being conjugated to PEG. In other cases, PEGylation can comprise linking a PEG molecule to a native or recombinant MTAP polypeptide, fragment herein and thereof, or portion herein and thereof.

In some instances, a PEG molecule can be attached, conjugate, or linked to an MTAP polypeptide at a lysine, serine, histidine, tyrosine, cysteine, N-terminal amine, phenylalanine, C-terminal cysteine, arginine, aspartic acid, glutamic acid, serine, threonine, asparagine, N-terminus, C-terminus, or any combination herein and thereof of the MTAP polypeptide. In some cases, a PEG molecule can be attached, conjugate, or linked to an MTAP polypeptide at a lysine or cysteine of the MTAP polypeptide. In some instances, the C-terminal carboxylic acid can also be used in PEGylation of an MTAP polypeptide. In some cases, a PEG molecule can be attached, conjugate, or linked to an MTAP polypeptide at a lysine and cysteine of the MTAP polypeptide.

In some instances, a PEG molecule can be activated at each terminus with the same reactive moiety, i.e., the PEG molecule is "homobifunctional". In other cases, a PEG molecule can be activated at each terminus a different reactive moiety, i.e., then the PEG molecule is "heterobifunctional" or "heterofunctional". In some cases, a chemically active or activated derivatives of the PEG molecule can be prepared to attach the PEG molecule to an MTAP polypeptide.

In some instances, a PEG molecule can be attached, conjugate, or linked to an MTAP polypeptide at succinimidyl ester, aldehyde, maleimide, p-nitrophenyl carbonate ester, any derivative herein and thereof, or any combinations herein and thereof. In some cases, the generation of a PEG molecule for PEGylation of an MTAP polypeptide can comprise reacting the PEG molecule with a group that is reactive with hydroxyl groups comprising anhydrides, acid chlorides, chloroformates, or carbonates. In other cases, the generation of a PEG molecule for PEGylation of an MTAP polypeptide can comprise reacting the PEG molecule with a group that is reactive with functional groups comprising aldehyde, esters, or amides. In some cases, a methoxy PEG molecular can be used for PEGylation of an MTAP polypeptide. In some instances, a polyethylene glycol (PEG diol) can also be used for PEGylation of an MTAP polypeptide. In some cases, the diol group can be modified at both ends in order to make a hetero- or homo-dimeric PEGylated MTAP polypeptide.

In some cases, an MTAP polypeptide can be PEGylated at nucleophilic sites. In other cases, a nucleophilic site can comprise an unprotonated thiol group or an amino or amine group. In some instances, an amino or amine group on the side chain of a lysine or the N-terminus of a protein can be used for PEGylation of an MTAP polypeptide. In some cases, a protein can be conjugated to a PEG molecule through the alkylation of an amine or amino group of on the side chain of a lysine or the N-terminus of the protein. In some cases, a PEG-aldehyde, NHS-PEG, PEG tresylate, PEG isothiocyanate or succinimide a PEG molecule can be used to conjugate the amino group on the side chain of a lysine on an MTAP polypeptide. In other cases, succinimidyl carbonate (PEG-SC), benzotriazole carbonate (PEG-BTC), phenyl carbonate, carbonylimidazole, or thiazolidine-2-thione can also be used for PEGylation of an MTAP polypeptide. In some instances, a cyanuric chloride activated a PEG molecule can be used to react with the primary amine groups of a lysine of an MTAP polypeptide. In some instances, a PEG aldehyde derivative (e.g., Methoxy PEG propionaldehyde or mPEG-propionaldehyde) can be used to forma stable secondary amine linkage with an amino group of lysine of an MTAP polypeptide through reductive alkylation using sodium cyanoborohydride. In some cases, a reaction with a low pH can be used to direct PEGylation to specific groups of amino groups. Such specific groups of amino groups can comprise an amino group with low pKa.

In some instances, a unprotonated thiol group can comprise a side chain of a cysteine. In some cases, PEG maleimide, PEG iodoacetate, PEG thiols, or PEG vinylsulfone can be used to PEGylate an MTAP polypeptide at a cysteine. In some cases, a native cysteine can be used for PEGylation. In other cases, a cysteine residue can be engineered into a MTAP polypeptide for PEGylation. Such engineering can comprise adding a cysteine to an MTAP polypeptide. In other cases, a cysteine can replace any amino acid residue of an MTAP polypeptide. In some instances, a cysteine based PEGylation can comprise reacting a maleimide group attached to PEG with a free cysteine. A free cysteine, in some cases, may not be involved in a disulfide bond.

In some instances, PEG can be conjugated to an MTAP polypeptide at a disulfide bond of the MTAP polypeptide. In some cases, disulfide bond based PEGylation can comprise reducing a disulfide under mild conditions and labeling the cysteines involved in the disulfide with a bis(thiol)-specific reagent. In such cases, dithiomaleimide can be used to create the disulfide bond based PEGylation.

In some cases, PEG can be conjugated to an MTAP polypeptide at a tyrosine residue. In some instances, a tyrosine of an MTAP polypeptide can be reacted with a 4-phenyl-3H-1,2,4-triazoline-3,5(4H)-dione (PTAD) to create a covalent bond between MTAP and PEG. In some cases, a PEG-PTAD conjugate can be created first and reacted with a tyrosine of an MTAP polypeptide.

In some cases, a PEGylated can be prepared by direct chemical synthesis of an MTAP polypeptide, wherein the MTAP polypeptide is attached to a solid phase peptide synthesis (SPPS) and PEG is incorporated in one of the coupling steps or through direct chemical attachment of a native chemical feature of the MTAP polypeptide. In some cases, a native chemical feature can comprise a chemical feature present in the PEGylation conjugation site described herein and thereof. In some cases, a native chemical feature can also comprise an alkylating-containing residue. In other cases, an azide-PEG conjugate can be attached to an alkylating-containing residue with the Huisgen 1,3-dipolar cycloaddition. In other cases, PEG can be conjugated to an MTAP polypeptide using an Fmoc-asparagine, where the Fmoc-asparagine is incorporated to the MTAP polypeptide during SPPS.

In some cases, for amine-based PEGylation of an MTAP polypeptide, the parameters to be optimized in the PEGylation reaction can comprise the polypeptide concentration, PEG-to-polypeptide ratio on a molar basis, temperature, or pH, reaction time. In some cases, for thiol-based PEGylation of an MTAP polypeptide, the parameters to be optimized in the PEGylation reaction can comprise the polypeptide concentration, PEG-to-polypeptide ratio on a molar basis, temperature, pH, reaction time, or exclusion of oxygen. In some instances, the PEGylation reaction can affect the stability of an MTAP polypeptide. the reactivity of a PEG molecule should be known before starting a PEGylation reaction. In some cases, for example, if a PEG molecule is only 70% active in a PEGylation reaction of an MTAP polypeptide, the amount of the PEG molecule used should ensure that only active PEG molecules can be counted in the MTAP-to-PEG reaction stoichiometry.

Polyethylene Glycol (PEG)

In some instances, a PEG molecule can comprise a polymer. In some cases, a PEG molecule can comprise homopolymer of ethylene glycol or ethylene oxide. In some cases, a PEG molecule can comprise polyethylene oxide (PEO) or polyoxyethylene (POE). In some cases, a PEG molecule can comprise Formula I:

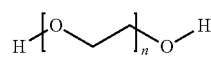

Wherein n is the number of units. In some cases, a PEG molecule can have a molecular weight 44.05n+18.02 g/mol, where n is the number of units as in Formula I. In some instances, the molecular weight of a PEG molecule species can be used to calculate the number of units, such as that of Formula I or derivatives herein and thereof, and vice versa. In some cases, a PEG molecule can also have a formula H—(O—CH2-CH2)n-OH or $C_{2n}H_{4n+2}O_{n+1}$, where n is the number of unit.

In some cases, a PEG molecule can be represented as PEG-N, where N can comprise the number of units, such as n in Formula I. In some cases, a PEG molecule can also have a formula H—(O—CH2-CH2)n-OH or $C_{2n}H_{4n+2}O_{n+1}$, where n is the number of units. In some cases, a PEG molecule with different number of units can have different properties. In some cases, a PEG molecule with low molecular weight can be viscous or colorless liquids. In other cases, a PEG molecule with high molecular weight can be crystallized with high melting points. A high melting point can be higher than 70° C.

In some cases, a PEG molecule can have an average molecular weight of about 100 kDa, 150 kDa, 200 kDa, 250 kDa, 300 kDa, 350 kDa, 400 kDa, 450 kDa, 500 kDa, 550 kDa, 600 kDa, 650 kDa, 700 kDa, 750 kDa, 800 kDa, 850 kDa, 900 kDa, 950 kDa, 1000 kDa, 1050 kDa, 1100 kDa, 1150 kDa, 1200 kDa, 1250 kDa, 1300 kDa, 1350 kDa, 1400 kDa, 1450 kDa, 1500 kDa, 1550 kDa, 1600 kDa, 1650 kDa, 1700 kDa, 1750 kDa, 1800 kDa, 1850 kDa, 1900 kDa, 1950 kDa, 2000 kDa, 2050 kDa, 2100 kDa, 2150 kDa, 2200 kDa, 2250 kDa, 2300 kDa, 2350 kDa, 2400 kDa, 2450 kDa, 2500 kDa, 2550 kDa, 2600 kDa, 2650 kDa, 2700 kDa, 2750 kDa, 2800 kDa, 2850 kDa, 2900 kDa, 2950 kDa, 3000 kDa, 3050 kDa, 3100 kDa, 3150 kDa, 3200 kDa, 3250 kDa, 3300 kDa, 3350 kDa, 3400 kDa, 3450 kDa, 3500 kDa, 4000 kDa, 5000 kDa, 6000 kDa, 7000 kDa, 8000 kDa, 9000 kDa, 10000 kDa, 11000 kDa, 12000 kDa, 13000 kDa, 14000 kDa, 15000 kDa, 16000 kDa, 17000 kDa, 18000 kDa, 19000 kDa, 20000 kDa, 21000 kDa, 22000 kDa, 23000 kDa, 24000 kDa, 25000 kDa, 26000 kDa, 27000 kDa, 28000 kDa, 29000 kDa, 30000 kDa, 31000 kDa, 32000 kDa, 33000 kDa, 34000 kDa, 35000 kDa or more than 35000 kDa. In some cases, a PEG molecule can have an average molecular weight from about 100 to about 1000 kDa, from about 500 to about 1500 kDa, from about 1000 to about 2000 kDa, from about 1500 to about 2500 kDa, from about 2000 to about 3000 kDa, from about 2500 to about 3500 kDa, from about 3000 to about 4000 kDa, from about 3500 to about 4500 kDa, from about 4000 to about 5000 kDa, from about 4500 to about 5500 kDa, from about 5000 to about 6000 kDa, from about 5500 to about 6500 kDa, from about 6000 to about 7000 kDa, from about 6500 to about 7500 kDa, from about 7000 to about 8000 kDa, from about 7500 to about 8500 kDa, from about 8000 to about 9000 kDa, from about 8500 to about 9500 kDa, from about 9000 to about 10000 kDa, from about 9500 to about 10500 kDa, from about 10000 to about 11000 kDa, from about 10500 to about 11500 kDa, from about 11000 to about 12000 kDa, from about 11500 to about 12500 kDa, from about 12000 to about 13000 kDa, from about 12500 to about 13500 kDa, from about 13000 to about 14000 kDa, from about 13500 to about 14500 kDa, from about 14000 to about 15000 kDa, from about 14500 to about 15500 kDa, from about 15000 to about 16000 kDa, from about 15500 to about 16500 kDa, from about 16000 to about 17000 kDa, from about 16500 to about 17500 kDa, from about 17000 to about 18000 kDa, from about 17500 to about 18500 kDa, from about 18000 to about 19000 kDa, from about 18500 to about 19500 kDa, from about 19000 to about 20000 kDa, from about 19500 to about 20500 kDa, from about 20000 to about 21000 kDa, from about 20500 to about 21500 kDa, from about 21000 to about 22000 kDa, from about 21500 to about 22500 kDa, from about 22000 to about 23000 kDa, from about 22500 to about 23500 kDa, from about 23000 to about 24000 kDa, from about 23500 to about 24500 kDa, from about 24000 to about 25000 kDa, from about 24500 to about 25500 kDa, from about 25000 to about 26000 kDa, from about 25500 to about 26500 kDa, from about 26000 to about 27000 kDa, from about 26500 to about 27500 kDa, from about 27000 to about 28000 kDa, from about 27500 to about 28500 kDa, from about 28000 to about 29000 kDa, from about 28500 to about 29500 kDa, from about 29000 to about 30000 kDa, from about 29500 to about 30500 kDa, from about 30000 to about 31000 kDa, from about 30500 to about 31500 kDa, from about 31000 to about 32000 kDa, from about 31500 to about 32500 kDa, from about 32000 to about 33000 kDa, from about 32500 to about 33500 kDa, from about 33000 to about 34000 kDa, from about 33500 to about 34500 kDa, or from about 34000 to about 35000 kDa. In some instances, a PEG molecule can have an average molecular weight of about 5000 kDa. In other cases, a PEG molecule can have an average molecular weight of about 500 kDa to about 1000 kDa, about 800 kDa to about 1600 kDa, about 1500 kDa to about 3000 kDa, about 2000 kDa to about 4000 kDa, about 2500 kDa to about 5000 kDa, about 3000 kDa to about 6000 kDa, about 4,000 kDa to about 8,000 kDa, about 6,000 kDa to about 12,000 kDa, about 10,000 kDa to about 20,000 kDa, or about 15,000 kDa to about 30,000 kDa.

In some instances, a PEG molecule can comprise a glass transition temperature ($T_g$) from −40° C. to −70° C. In some cases, a PEG molecule can be dissolved in polar or nonpolar solvents. In some instances, a PEG molecule can be dissolved in hydrophilic solvents. In some instances, a PEG molecule can dissolve in organic solvents. One such organic solvent can comprise alcohol, methylene chloride, acetone, toluene, acetonitrile, benzene, dichloromethane, chloroform, derivatives herein and thereof, or any combination herein and thereof. In other cases, a PEG molecule can also be amphiphilic.

In some instances, a PEG molecule can have a branched, star, linear, comb-like, structure; derivatives herein and thereof; or any combinations herein and thereof. In some instances, a PEG molecule can comprise a terminal hydroxyl group. In other cases, a PEG molecule can convert a terminal hydroxyl group into a symmetric or asymmetric functional group. In some cases, a PEG molecule or any manufactures comprising a PEG molecule can be bioinert. Being bioinert may comprise a resistance to biological reaction. One such biological reaction can comprise degradation of a PEG molecule or any manufactures comprising PEG. In other cases, being bioinert can mean having a minimal intrinsic biological activity. In some cases, a PEG molecule can have low immunogenicity. In some cases, a PEG molecule may not have immunogenicity. Immunogenicity of an entity can comprise the ability of an entity to elicit or activate an immune response against the entity when the entity is presented or administered to or detected by an immune system. In some cases, a PEG molecule may not elicit an immune response directed to the PEG molecule when administered or presented to an immune system. In other cases, a PEG molecule may not be toxic. In some instances, a PEG molecule may create a high osmotic pressure. In some cases, a PEG molecule can be crosslinked into a hydrogel. In other cases, a PEG molecule may not carry a charge.

In some cases, PEO or POE can have a molecular weight of at least about $1\times10^5$ g/mol, $2\times10^5$ g/mol, $3\times10^5$ g/mol, $4\times10^5$ g/mol, $5\times10^5$ g/mol, $6\times10^5$ g/mol, $7\times10^5$ g, $8\times10^5$ g/mol, $9\times10^5$ g/mol, $1\times10^6$ g/mol, $2\times10^6$ g/mol, $3\times10^6$ g/mol, $4\times10^6$ g/mol, $5\times10^6$ g/mol, $6\times10^6$ g/mol, $7\times10^6$ g/mol, $8\times10^6$ g/mol, $9\times10^6$ g/mol, $1\times10^7$ g/mol, or more.

Fusion Protein

In some instances, an MTAP polypeptide can comprise a heterologous object. In some cases, a heterologous object can comprise a heterologous peptide. In some cases, an MTAP polypeptide and a heterologous peptide can be linked as a fusion protein. In some cases, a fusion protein comprising an MTAP polypeptide and a heterologous peptide can be constituted in the same translation unit, wherein the MTAP polypeptide and the heterologous peptide can share the same ATG start codon. In other cases, an MTAP polypeptide and a heterologous peptide can be linked by a covalent bond. Sun a covalent bond can comprise a peptide bond. In other cases, an MTAP polypeptide and a heterologous peptide can have a non-covalent bond. In some cases, an MTAP polypeptide and a heterologous peptide may not be constituted in the same translation unit.

In some cases, an MTAP polypeptide can comprise cell-targeting moieties comprising an antibody, a growth factor, a hormone, a peptide, an aptamer, a chemical, a drug, a nucleic acid, a cytokine, any derivatives herein and thereof, any biological equivalents herein and thereof, or any combination herein and thereof. For instance, a cell targeting moiety according the embodiments may bind to a skin cancer cell such as a melanoma cell. It has been demonstrated that the gp240 antigen is expressed in a variety of melanomas but not in normal tissues. Thus, in certain aspects of the embodiments, there is provided a cell targeting construct comprising an MTAP polypeptide and a cell-targeting moiety that binds to gp240. In some instances, the gp240 binding molecule may be an antibody, such as the ZME-018 (225.28S) antibody or the 9.2.27 antibody. In an even more preferred embodiment, the gp240 binding molecule may be a single chain antibody such as the scFvMEL antibody. Therefore, in a very specific embodiment of the invention, there is provided a cell targeting construct comprising MTase conjugated to scFvMEL.

In some instances, an MTAP polypeptide comprising a cell targeting moiety can be directed to breast cancer cells. In some cases, a cell targeting moiety can bind to Her-2/neu. In other cases, an MTAP polypeptide may comprise an anti-Her-2/neu antibody. In some instances, a fusion protein comprising an MTAP polypeptide and a targeting moiety comprising a single chain anti-Her-2/neu antibody scFv23. In other instances, a fusion protein comprising an MTAP polypeptide and a targeting moiety comprising a scFv (FRP5) that bind to Her-2/neu may also be used in the compositions and methods of the current embodiments (von Minckwitz et al., 2005).

In some cases, a cell targeting moiety can bind to multiple types of cancer cells. In some instances, an 8H9 monoclonal antibody and the single chain antibodies derived therefrom that bind to a glycoprotein expressed on breast cancers, sarcomas and neuroblastomas (Onda et al., 2004) can be used as a targeting moiety. In other cases, a cell targeting moiety can comprise the cell targeting agents described in U.S. patent application no. 2004/005647 and in Winthrop et al., 2003 that bind to MUC-1, an antigen that is expressed on a variety cancer types. In some cases, it is understood that in certain embodiments, cell targeting constructs according the embodiments may be targeted against a plurality of cancer or tumor types.

Certain cell surface molecules are highly expressed in tumor cells, comprising hormone receptors such as human chorionic gonadotropin receptor and gonadotropin releasing hormone receptor (Nechushtan et al., 1997). In some cases, a hormone peptide binding to a hormone receptor expressed by a cancer cell can be used as a cell targeting moiety that specifically targets cancer in cancer therapy.

In some cases, an immune checkpoint blockade inhibitor can be used as a cell targeting moiety. In some instances, an immune checkpoint blockade inhibitor can be used to form a fusion protein with an MTAP polypeptide. In other cases, an antibody, or fragment thereof (e.g., an scFv) that is antagonistic to PD-1, PDL-1, or PDL-2 (e.g., antibodies described in U.S. Pat. Nos. 8,735,553, 8,354,509, and 8,008,449; PCT Appln. Nos. WO2009/101611 and WO2009/114335) can be fused to an MTAP polypeptide. In another example, an antibody, or fragment thereof (e.g., an scFc) that recognizes CTLA-4 (e.g., U.S. Pat. No. 8,119,129 and PCT Appln. Nos. WO 01/14424, WO 98/42752, and WO 00/37504) may be fused to an MTAP polypeptide. In some instances, any checkpoint blockade molecules described herein and thereof can be used as a cell targeting moiety.

Linker

In some cases, an MTAP polypeptide can be chemically conjugated to a heterologous object by a bifunctional cross-linking reagent. In some cases, an MTAP polypeptide can be chemically conjugated to a heterologous object by a peptide linker.

In some cases, a suitable peptide linker comprises a Gly-Ser linker.

Bifunctional cross-linking reagent have been extensively used for a variety of purposes and well known in the art, comprising preparation of affinity matrices, modification and stabilization of diverse structures, identification of ligand and receptor binding sites, and structural studies.

In some cases, a bifunctional cross-linking reagent can comprise a homobifunctional reagent. In some instances, a homobifunctional reagent carrying two identical functional groups can be highly efficient in inducing cross-linking between identical and different macromolecules or subunits of a macromolecule and linking of polypeptide ligands to their specific binding sites. In some cases, a bifunctional cross-linking reagent can comprise a heterobifunctional reagent that contains two different functional groups. In some cases, a heterobifunctional reagent can control a cross-linking selectively and sequentially with the differential reactivities of the two different functional groups. In some instances, a bifunctional cross-linking reagent can be divided according to the specificity of their functional groups, e.g., amino-, sulfhydryl-, guanidine-, indole-, carboxyl-specific groups. In some instances, cross-linking reagents directed to free amino can be used based on their commercial availability, ease of synthesis, and the mild reaction conditions under which they can be applied.

In some cases, a heterobifunctional cross-linking reagent can comprise a primary amine-reactive group and a thiol-reactive group. In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling, in one example, of aldehydes to free thiols. The cross-linking reagent can be modified to cross-link various functional groups.

Additionally, any other linking/coupling agents and/or mechanisms known to those of skill in the art may be used to combine an MTAP polypeptide, comprising antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

In some instances, a cross-linker having reasonable stability in blood can be employed. Numerous types of disulfide-bond containing linkers are known that can be successfully employed to conjugate targeting and therapeutic/preventative agents. In some cases, a linker comprising a disulfide bond that is sterically hindered can give greater stability of a molecule being conjugated to the linker in vivo. These linkers are thus one group of linking agents.

In some cases, a non-hindered linker can also be employed in accordance herewith. Other useful cross-linkers, not considered to contain or generate a protected disulfide, comprise SATA, SPDP, and 2-iminothiolane (Wawrzynczak and Thorpe, 1987). The use of such cross-linkers is well understood in the art. In some cases, a flexible linker can be used.

In some cases, once chemically conjugated, a peptide can be purified to separate the conjugate from unconjugated agents and from other contaminants. In some instances, a large number of purification techniques are available for use in providing conjugates of a sufficient degree of purity to render them clinically useful. In some cases, purification methods can comprise methods based upon size separation, such as gel filtration, gel permeation, or high-performance liquid chromatography, will generally be of most use. Other chromatographic techniques, such as Blue-Sepharose separation, may also be used. Conventional methods to purify the fusion proteins from inclusion bodies may be useful, such as using weak detergents, such as sodium N-lauroyl-sarcosine (SLS).

Vectors

The nucleic acids provided herein can be delivered by any suitable means. In some cases, a suitable means comprises a vector. Any vector system can be used utilized, including but not limited to: plasmid vectors, minicircle vectors, linear DNA vectors, doggy bone vectors, retroviral vectors, lentiviral vectors, adenovirus vectors, poxvirus vectors; herpes-virus vectors and adeno-associated virus vectors, a liposome, a nanoparticle, an exosome, an extracellular vesicle, a nanomesh, modified versions thereof, good manufacturing practices versions thereof, chimeras thereof, and any combination thereof. In some cases, a vector can be used to introduce a polynucleotide provided herein. In some cases, the polynucleotide comprises a targeting sequence that hybridizes to a region of an RNA provided herein. In some embodiments, a nanoparticle vector can comprise a polymeric-based nanoparticle, an amino lipid-based nanoparticle, a metallic nanoparticle (such as gold-based nanoparticle), a portion of any of these, or any combination thereof.

In some cases, a vector may not be a viral vector. Non-viral methods can comprise naked delivery of compositions comprising polynucleotides and the like. In some cases, modifications provided herein can be incorporated into polynucleotides to increase stability and combat degradation when being delivered as naked polynucleotides. In other cases, a non-viral approach can harness use of nanoparticles, liposomes, and the like.

Host Cell

In some cases, host cells may be any that may be transformed to allow the expression and secretion of an MTAP polypeptide and conjugates thereof. In some instances, a host cell may comprise bacteria, mammalian cells, yeast, or filamentous fungi. In some instances, bacteria can comprise *Escherichia* and *Bacillus*. In some instances, bacteria can comprise *Escherichia coli* (*E. coli*) or *Salmonella enterica*. In other cases, yeasts belonging to the genera *Saccharomyces, Kiuyveromyces, Hansenula,* or *Pichia* can be used as host cells. In some instances, filamentous fungi may be used as expression hosts, comprising *Aspergillus, Trichoderma, Neurospora, Penicillium, Cephalosporium, Achlya, Podospora, Endothia, Mucor, Cochliobolus,* or *Pyricularia*.

In some cases, a host cell bacterial or yeast strain can comprise *Escherichia coli* MC1061, derivatives of *Bacillus subtilis* BRB1 (Sibakov et al., 1984), *Staphylococcus aureus* SAI123 (Iordanescu, 1975) or *Streptococcus lividans* (Hopwood et al., 1985), *Saccharomyces cerevisiae* AH 22 (Mellor et al., 1983), *Schizosaccharomyces pombe, Aspergillus nidulans, Aspergillus awamori* (Ward, 1989), or *Trichoderma reesei* (Penttila et al., 1987; Harkki et al., 1989).

In some cases, ab MTAP polypeptide can be expressed in a mammalian host cell. In some cases, a mammalian host cell can comprise Chinese hamster ovary cells (CHO-K1; ATCC CCL61), rat pituitary cells (GH1; ATCC CCL82), HeLa S3 cells (ATCC CCL2.2), rat hepatoma cells (H-4-II-E; ATCCCRL 1548), SV40-transformed monkey kidney cells (COS-1; ATCC CRL 1650), and murine embryonic cells (NIH-3T3; ATCC CRL 1658).

In some cases, mammalian host cells expressing an MTAP polypeptide can be cultured under conditions typically employed to culture the parental cell line. In some cases, mammalian host cells expressing an MTAP polypeptide can be cultured in a standard medium containing physiological salts and nutrients, such as standard RPMI, MEM, IMEM, or DMEM, typically supplemented with 5%-10% serum, such as fetal bovine serum. In other cases, culture conditions can comprise cultures incubated at 37° C. in stationary or roller cultures until desired levels of the proteins are achieved.

In some cases, insect host cell can be used to express an MTAP polypeptide. In some cases, insect host cells can comprise Sf9, Sf21, High Five, or S2 cells. In other cases, insect expression host cells can comprise baculovirus expression systems.

Administration

In some cases, a PEGylated MTAP polypeptide, nucleic acid encoding the PEGylated MTAP polypeptide, or pharmaceutical composition herein and thereof can comprise packing the a PEGylated MTAP polypeptide, nucleic acid encoding the PEGylated MTAP polypeptide, or pharmaceutical composition herein and thereof into a composition or formulation for delivery or administration in a subject. In some cases, an administration of a PEGylated MTAP polypeptide, nucleic acid encoding the PEGylated MTAP polypeptide, or pharmaceutical composition herein and thereof can refer to methods that can be used to enable delivery of the a PEGylated MTAP polypeptide, nucleic acid encoding the PEGylated MTAP polypeptide, or pharmaceutical composition herein and thereof to the desired site of biological action. Delivery can comprise direct application to the affect tissue or region of the body. Delivery can include intracranial injection. Delivery can include a parenchymal injection, an intra-thecal injection, an intra-ventricular injection, or an intra-cisternal injection. A PEGylated MTAP polypeptide, nucleic acid encoding the PEGylated MTAP polypeptide, or pharmaceutical composition herein and thereof herein can be administered by any method. A method of administration can be by inhalation, intraarterial injection, intracerebroventricular injection, intracisternal injection, intramuscular injection, infraorbital injection, intraparenchymal injection, intraperitoneal injection, intraspinal injection, intrathecal injection, intravenous injection, intraventricular injection, stereotactic injection, subcutaneous injection, or any combination thereof. Delivery can include parenteral administration (including intravenous, subcutaneous, intrathecal, intraperitoneal, intramuscular, intravascular or gradual infusion), oral administration, inhalation administration, intraduodenal administration, rectal administration. Delivery can include topical administration (such as a lotion, a cream, an ointment) to an external surface of a surface, such as a skin. In some cases, administration is by parenchymal injection, intra-thecal injection, intra-ventricular injection, intra-cisternal injection, intravenous injection, or intranasal administration or any combination thereof. In some instances, a subject can administer the composition in the absence of supervision. In some instances, a subject can administer the composition under the supervision of a medical professional (e.g., a physician, nurse, physician's assistant, orderly, hospice worker, etc.). A medical professional can administer the composition. In some cases, a cosmetic professional can administer the composition. In some cases, a PEGylated MTAP polypeptide, nucleic acid encoding the PEGylated MTAP polypeptide, or pharmaceutical composition herein and thereof can also be delivered by peristaltic means, injected directly into the urinary tract, or administered by a pump connected to a catheter that may contain a potential biosensor for MTA or ADO. In some cases, a PEGylated MTAP polypeptide, nucleic acid encoding the PEGylated MTAP polypeptide, or pharmaceutical composition herein and thereof can also be administered intratumorally, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage.

The methods of treating an individual with cancer described herein can comprise administration of a PEGylated MTAP polypeptide, nucleic acid encoding the PEGylated MTAP polypeptide, or pharmaceutical composition herein and thereof in an individual with a cancer or suspected of a cancer. The methods of treating an individual with cancer described herein can also comprise administration of a PEGylated MTAP polypeptide, nucleic acid encoding the PEGylated MTAP polypeptide, or pharmaceutical composition herein and thereof in an individual without a cancer or suspected of a cancer.

Administration or application of a PEGylated MTAP polypeptide, nucleic acid encoding the PEGylated MTAP polypeptide, or pharmaceutical composition herein and thereof can be performed for a treatment duration of at least about at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 days consecutive or nonconsecutive days. A treatment duration can be from about 1 to about 30 days, from about 2 to about 30 days, from about 3 to about 30 days, from about 4 to about 30 days, from about 5 to about 30 days, from about 6 to about 30 days, from about 7 to about 30 days, from about 8 to about 30 days, from about 9 to about 30 days, from about 10 to about 30 days, from about 11 to about 30 days, from about 12 to about 30 days, from about 13 to about 30 days, from about 14 to about 30 days, from about 15 to about 30 days, from about 16 to about 30 days, from about 17 to about 30 days, from about 18 to about 30 days, from about 19 to about 30 days, from about 20 to about 30 days, from about 21 to about 30 days, from about 22 to about 30 days, from about 23 to about 30 days, from about 24 to about 30 days, from about 25 to about 30 days, from about 26 to about 30 days, from about 27 to about 30 days, from about 28 to about 30 days, or from about 29 to about 30 days.

In some instances, administration or application of a PEGylated MTAP polypeptide, nucleic acid encoding the PEGylated MTAP polypeptide, or pharmaceutical composition herein and thereof can be performed for a treatment duration of at least about 1 week, at least about 1 month, at least about 1 year, at least about 2 years, at least about 3 years, at least about 4 years, at least about 5 years, at least about 6 years, at least about 7 years, at least about 8 years, at least about 9 years, at least about 10 years, at least about 15 years, at least about 20 years, or more. Administration can be performed repeatedly over a lifetime of a subject, such as once a month or once a year for the lifetime of a subject. Administration can be performed repeatedly over a substantial portion of a subject's life, such as once a month or once a year for at least about 1 year, 5 years, 10 years, 15 years, 20 years, 25 years, 30 years, or more.

In some cases, an administration of any PEGylated MTAP polypeptide, nucleic acid encoding the PEGylated MTAP polypeptide, or pharmaceutical composition herein and thereof to reduce a symptom of a disease or condition and/or to reduce a disease or condition. In some instances, an effective amount can be sufficient to achieve a desired effect. In the context of therapeutic or prophylactic applications, the effective amount will depend on the type and severity of the condition at issue and the characteristics of the individual subject, such as general health, age, sex, body weight, and tolerance to the PEGylated MTAP polypeptide, nucleic acid encoding the PEGylated MTAP polypeptide, or pharmaceutical composition herein and thereof.

Dosing

Administration or application of a PEGylated MTAP polypeptide, nucleic acid encoding the PEGylated MTAP polypeptide, or pharmaceutical composition herein and thereof can be performed at least 1, 2, 3, 4, 5, 6, 7, 8, 9, 10, 11, 12, 13, 14, 15, 16, 17, 18, 19, 20, 21, 22, 23, or 24 times a day. In some cases, administration or application of personalized tumor vaccines or pharmaceutical compositions disclosed herein can be performed at least 1, 2, 3, 4, 5, 6, 7, 8, 9, 10, 11, 12, 13, 14, 15, 16, 17, 18, 19, 20, or 21 times a week. In some cases, administration or application of a PEGylated MTAP polypeptide, nucleic acid encoding the PEGylated MTAP polypeptide, or pharmaceutical composition herein and thereof can be performed at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 times a month.

A PEGylated MTAP polypeptide, nucleic acid encoding the PEGylated MTAP polypeptide, or pharmaceutical composition herein and thereof can be administered/applied as a single dose or as divided doses. In some cases, the PEGylated MTAP polypeptide, nucleic acid encoding the PEGylated MTAP polypeptide, or pharmaceutical composition herein and thereof can be administered at a first time point and a second time point. In some cases, a PEGylated MTAP polypeptide, nucleic acid encoding the PEGylated MTAP polypeptide, or pharmaceutical composition herein and thereof can be administered such that a first administration is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks, 2 months, 3 months, 4 months, 5 months, 6 months, 7 months, 8 months, 9 months, 10 months, 11 months, 1 year or more.

In some cases, a PEGylated MTAP polypeptide, nucleic acid encoding the PEGylated MTAP polypeptide, or pharmaceutical composition comprising the PEGylated MTAP polypeptide described herein and thereof can reduce the size of a tumor. In other cases, a PEGylated MTAP polypeptide, nucleic acid encoding the PEGylated MTAP polypeptide, or pharmaceutical composition can decrease the size of a tumor by 0%, 5%, 10%, 15%, 20%, 25%, 30%, 35%, 40%, 45%, 50%, 55%, 60%, 65%, 70%, 75%, 80%, 85%, 90%, 95%, or 100% of the size of the tumor before the administration of the PEGylated MTAP polypeptide. In some instances, a PEGylated MTAP polypeptide, nucleic acid encoding the PEGylated MTAP polypeptide, or pharmaceutical composition can decrease the size of a tumor by 1-10%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, or 90-100% of the size of the tumor before the administration of the PEGylated MTAP polypeptide, nucleic acid encoding the PEGylated MTAP polypeptide, or pharmaceutical composition.

In some instances, an effective amount of a PEGylated MTAP polypeptide, nucleic acid encoding the PEGylated MTAP polypeptide, or pharmaceutical composition can reduce the number of cancer cells. In some cases, a PEGylated MTAP polypeptide, nucleic acid encoding the PEGylated MTAP polypeptide, or pharmaceutical composition described herein and thereof can reduce the number of cancer cells by 0%, 5%, 10%, 15%, 20%, 25%, 30%, 35%, 40%, 45%, 50%, 55%, 60%, 65%, 70%, 75%, 80%, 85%, 90%, 95%, or 100% of number of the cancer cells before the administration of the PEGylated MTAP polypeptide, nucleic acid encoding the PEGylated MTAP polypeptide, or pharmaceutical composition. In some instances, an effective amount of a PEGylated MTAP polypeptide, nucleic acid encoding the PEGylated MTAP polypeptide, or pharmaceutical composition herein and thereof can decrease the number of cancer cells by 1-10%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, or 90-100% of the number of the cancer cells before the administration of the PEGylated MTAP polypeptide, nucleic acid encoding the PEGylated MTAP polypeptide, or pharmaceutical composition.

In some cases, a PEGylated MTAP polypeptide, nucleic acid encoding the PEGylated MTAP polypeptide, or pharmaceutical composition comprising the PEGylated MTAP polypeptide described herein and thereof can decrease or prevent metastasis of a tumor. In other cases, a PEGylated MTAP polypeptide, nucleic acid encoding the PEGylated MTAP polypeptide, or pharmaceutical composition can decrease or prevent metastasis of a tumor by 0%, 5%, 10%, 15%, 20%, 25%, 30%, 35%, 40%, 45%, 50%, 55%, 60%, 65%, 70%, 75%, 80%, 85%, 90%, 95%, or 100% of that of a tumor without the administration of the PEGylated MTAP polypeptide. In some instances, a PEGylated MTAP polypeptide, nucleic acid encoding the PEGylated MTAP polypeptide, or pharmaceutical composition can decrease or prevent metastasis of a tumor by 1-10%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, or 90-100% of that the tumor without the administration of the PEGylated MTAP polypeptide, nucleic acid encoding the PEGylated MTAP polypeptide, or pharmaceutical composition. In some instances, an effective amount of a PEGylated MTAP polypeptide, nucleic acid encoding the PEGylated MTAP polypeptide, or pharmaceutical composition herein and thereof can delay the metastasis of a tumor by 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, 3 months, 4 months, 5 months, 6 months, 7 months, 8 months, 9 months, 10 months, 11 months, 12 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, or more than 50 years. In some instances, an effective amount of a PEGylated MTAP polypeptide, nucleic acid encoding the PEGylated MTAP polypeptide, or pharmaceutical composition herein and thereof can delay the metastasis of a tumor by an amount of time from 1 day to 1 month, from 25 days to 6 months, from 5 months to 12 months, from 10 months to 2 years, from 1 year to 5 years, from 4 years to 10 years, from 9 years to 15 years, from 14 years to 20 years, from 19 years to 25 years, from 24 years to 30 years, from 29 years to 35 years, from 34 years to 40 years, from 39 years to 45 years, or from 44 years to 50 years.

In some cases, an effective amount of a PEGylated MTAP polypeptide, nucleic acid encoding the PEGylated MTAP polypeptide, or pharmaceutical composition herein and thereof can extend the life-span of a subject administered with the PEGylated MTAP polypeptide, nucleic acid encoding the PEGylated MTAP polypeptide, or pharmaceutical composition. In some instances, an effective amount of a PEGylated MTAP polypeptide, nucleic acid encoding the PEGylated MTAP polypeptide, or pharmaceutical composition herein and thereof can extend the life-span of a subject administered with PEGylated MTAP polypeptide, nucleic acid encoding the PEGylated MTAP polypeptide, or pharmaceutical composition by 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, 3 months, 4 months, 5 months, 6 months, 7 months, 8 months, 9 months, 10 months, 11 months, 12 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, or more than 50 years. In some instances, an effective amount of a PEGylated MTAP polypeptide, nucleic acid encoding the PEGylated MTAP polypeptide, or pharmaceutical composition herein and thereof can extend the life-span of a subject administered with the PEGylated MTAP polypeptide, nucleic acid encoding the PEGylated MTAP polypeptide, or pharmaceutical composition by an amount of time from 1 day to 1 month, from 25 days to 6 months, from 5 months to 12 months, from 10 months to 2 years, from 1 year to 5 years, from 4 years to 10 years, from 9 years to 15 years, from 14 years to 20 years, from 19 years to 25 years, from 24 years to 30 years, from 29 years to 35 years, from 34 years to 40 years, from 39 years to 45 years, or from 44 years to 50 years.

In some cases, an effective amount of a PEGylated MTAP polypeptide, nucleic acid encoding the PEGylated MTAP polypeptide, or pharmaceutical composition herein and thereof can delay the onset of a cancer of a subject administered with the PEGylated MTAP polypeptide, nucleic acid encoding the PEGylated MTAP polypeptide, or pharmaceutical composition. In some instances, an effective amount of a PEGylated MTAP polypeptide, nucleic acid encoding the PEGylated MTAP polypeptide, or pharmaceutical composition herein and thereof can delay the onset of a cancer of a subject administered with the PEGylated MTAP polypeptide, nucleic acid encoding the PEGylated MTAP polypeptide, or pharmaceutical composition by 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, 3 months, 4 months, 5 months, 6 months, 7 months, 8 months, 9 months, 10 months, 11 months, 12 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, or more than 50 years. In some instances, an effective amount of a PEGylated MTAP polypeptide, nucleic acid encoding the PEGylated MTAP polypeptide, or pharmaceutical composition herein and thereof can delay the onset of a cancer of a subject administered with the PEGylated MTAP polypeptide, nucleic acid encoding the PEGylated MTAP polypeptide, or pharmaceutical composition by an amount of time from 1 day to 1 month, from 25 days to 6 months, from 5 months to 12 months, from 10 months to 2 years, from 1 year to 5 years, from 4 years to 10 years, from 9 years to 15 years, from 14 years to 20 years, from 19 years to 25 years, from 24 years to 30 years, from 29 years to 35 years, from 34 years to 40 years, from 39 years to 45 years, or from 44 years to 50 years.

In some cases, an effective amount of a PEGylated MTAP polypeptide, nucleic acid encoding the PEGylated MTAP polypeptide, or pharmaceutical composition herein and thereof can decrease the MTA level by 10%, 20%, 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000%, 2000%, 3000%, 4000%, 5000%, 6000%, 7000%, 8000%, 9000%, 10000%, 20000%, 30000%, 40000%, 50000%, 60000%, 70000%, 80000%, 90000%, or 100000%. In some cases, an effective amount of a PEGylated MTAP polypeptide, nucleic acid encoding the PEGylated MTAP polypeptide, or pharmaceutical composition herein and thereof can decrease the MTA level from 10 to 30%, from 20 to 40%, from 30 to 50%, from 40 to 60%, from 50 to 70%, from 60 to 80%, from 70 to 90%, from 80 to 100%, from 90 to 150%, from 100 to 200%, from 150 to 250%, from 200 to 300%, from 250 to 350%, from 300 to 400%, from 350 to 450%, from 400 to 500%, from 450 to 550%, from 500 to 600%, from 550 to 650%, from 600 to 700%, from 650 to 750%, from 700 to 800%, from 750 to 850%, from 800 to 900%, from 850 to 950%, from 900 to 1000%, from 950 to 2000%, from 1500 to 2500%, from 2000 to 3000%, from 2500 to 3500%, from 3000 to 4000%, from 3500 to 4500%, from 4000 to 5000%, from 4500 to 5500%, from 5000 to 6000%, from 5500 to 6500%, from 6000 to 7000%, from 6500 to 7500%, from 7000 to 8000%, from 7500 to 8500%, from 8000 to 9000%, from 8500 to 9500%, from 9000 to 10000%, from 9500 to 20000%, from 15000 to 25000%, from 20000 to 30000%, from 25000 to 35000%, from 30000 to 40000%, from 35000 to 45000%, from 40000 to 50000%, from 45000 to 55000%, from 50000 to 60000%, from 55000 to 65000%, from 60000 to 70000%, from 65000 to 75000%, from 70000 to 80000, from 75000 to 85000%, from 80000 to 90000%, from 85000 to 95000%, or from 90000 to 100000%.

In some cases, an effective amount of a PEGylated MTAP polypeptide, nucleic acid encoding the PEGylated MTAP polypeptide, or pharmaceutical composition herein and thereof can decrease the ADO level by 10%, 20%, 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000%, 2000%, 3000%, 4000%, 5000%, 6000%, 7000%, 8000%, 9000%, 10000%, 20000%, 30000%, 40000%, 50000%, 60000%, 70000%, 80000%, 90000%, or 100000%. In some cases, an effective amount of a PEGylated MTAP polypeptide, nucleic acid encoding the PEGylated MTAP polypeptide, or pharmaceutical composition herein and thereof can decrease the ADO level from 10 to 30%, from 20 to 40%, from 30 to 50%, from 40 to 60%, from 50 to 70%, from 60 to 80%, from 70 to 90%, from 80 to 100%, from 90 to 150%, from 100 to 200%, from 150 to 250%, from 200 to 300%, from 250 to 350%, from 300 to 400%, from 350 to 450%, from 400 to 500%, from 450 to 550%, from 500 to 600%, from 550 to 650%, from 600 to 700%, from 650 to 750%, from 700 to 800%, from 750 to 850%, from 800 to 900%, from 850 to 950%, from 900 to 1000%, from 950 to 2000%, from 1500 to 2500%, from 2000 to 3000%, from 2500 to 3500%, from 3000 to 4000%, from 3500 to 4500%, from 4000 to 5000%, from 4500 to 5500%, from 5000 to 6000%, from 5500 to 6500%, from 6000 to 7000%, from 6500 to 7500%, from 7000 to 8000%, from 7500 to 8500%, from 8000 to 9000%, from 8500 to 9500%, from 9000 to 10000%, from 9500 to 20000%, from 15000 to 25000%, from 20000 to 30000%, from 25000 to 35000%, from 30000 to 40000%, from 35000 to 45000%, from 40000 to 50000%, from 45000 to 55000%, from 50000 to 60000%, from 55000 to 65000%, from 60000 to 70000%, from 65000 to 75000%, from 70000 to 80000%, from 75000 to 85000%, from 80000 to 90000%, from 85000 to 95000%, or from 90000 to 100000%.

In some cases, a reduction of MTA or ADO level can be conducted in vivo in the circulation of a mammal, in vitro in cases where MTA or ADO reduction in tissue culture or other biological mediums is desired, and in ex vivo procedures where biological fluids, cells, or tissues are manipulated outside the body and subsequently returned to the body of the patient mammal. In some case, a reduction of MTA or ADO from circulation, culture media, biological fluids, or cells can be conducted to reduce the amount of MTA or ADO accessible to the material being treated, and therefore comprises contacting the material to be depleted with a MTA or ADO-degrading amount of an MTAP polypeptide under MTA or ADO-degrading conditions as to degrade the ambient MTA or ADO in the material being contacted.

In some instances, the MTA or ADO-degrading efficiency of a PEGylated MTAP polypeptide, nucleic acid encoding the PEGylated MTAP polypeptide, or pharmaceutical composition herein and thereof can vary widely depending upon the application; and can depend upon the amount of MTA and/or ADO present in the material, the desired rate of depletion, and the tolerance of the material for exposure to the administered materials. In some cases, MTA or ADO levels in a material, and therefore rates of MTA or ADO depletion from the material, can readily be monitored by a variety of chemical and biochemical methods well known in the art. In some instances, MTA- or ADO-degrading amounts can be described further herein, and can range from 0.001 to 100 units (U) of MTase, preferably about 0.01 to 10 U, and more preferably about 0.1 to 5 U MTase per milliliter (mL) of material to be treated.

In some cases, the conditions for MTA or ADO-degrading can comprise buffer and temperature conditions compatible with the biological activity of an MTAP polypeptide, comprise moderate temperature, salt, and pH conditions compatible with the enzyme, for example, physiological conditions. Exemplary conditions can comprise about 4-40° C., ionic strength equivalent to about 0.05 to 0.2 M NaCl, and a pH of about 5 to 9, while physiological conditions are included.

In some case, a PEGylated MTAP polypeptide, nucleic acid encoding the PEGylated MTAP polypeptide, or pharmaceutical composition herein and thereof can be conventionally administered intravenously, as by injection of a unit dose.

In some cases, the quantity to be administered depends on the subject to be treated, capacity of the subject's system to utilize the enzyme, and degree of therapeutic effect desired. In some instances, precise amounts of enzyme required to be administered can depend on the judgment of the practitioner and are peculiar to each individual. In some cases, suitable dosage ranges for systemic application are disclosed herein and can depend on the route of administration. In some instances, suitable regimes for initial administration and booster shots can also be contemplated and be typified by an initial administration followed by repeated doses at one or more hour intervals by a subsequent injection or other administration. In some instances, administrations are described herein and are particularly preferred to maintain continuously high serum and tissue levels of MTAP polypeptides and conversely low serum and tissue levels of MTA or ADO. In some cases, continuous intravenous infusion sufficient to maintain concentrations in the blood in the ranges specified for in vivo therapies can be contemplated.

In some cases, an effective amount of a PEGylated MTAP polypeptide, nucleic acid encoding the PEGylated MTAP polypeptide, or pharmaceutical composition can be adjusted based on the material being administered. In some instances, the effective amount of a PEGylated MTAP polypeptide, nucleic acid encoding the PEGylated MTAP polypeptide, or pharmaceutical composition can vary based on the therapeutic desirable outcome described herein and thereof being sought.

In some cases, a therapeutically effective amount of an MTAP polypeptide can comprise a predetermined amount calculated to achieve the desired effect comprising a reduction of MTA or ADO in a patient's circulation. Thus, the dosage ranges for the administration of an MTAP polypeptide are those large enough to produce the desired effect. The dosage should not be so large as to cause adverse side effects, such as hyperviscosity syndromes, pulmonary edema, congestive heart failure, and the like. Generally, the dosage will vary with age of, condition of, sex of, and extent of the disease in the patient and can be determined by one of skill in the art. The dosage can be adjusted by the individual physician in the event of any complication.

In other cases, a therapeutically effective amount of an MTAP polypeptide may be an amount such that when administered in a physiologically tolerable composition is sufficient to achieve a intravascular (plasma) or local concentration of from about 0.001 to about 100 units (U) per mL, preferably above about 0.1 U, and more preferably above 1 U MTase per mL. Typical dosages can be administered based on body weight and are in the range of about 5-1000 U/kilogram (kg)/day, preferably about 5-100 U/kg/day, more preferably about 10-50 U/kg/day, and more preferably about 20-40 U/kg/day.

In some embodiments, a dose may also comprise about $1\times10^1$ microgram/kg/body weight, about $2\times10^1$ microgram/kg/body weight, about $3\times10^1$ microgram/kg/body weight, about $4\times10^1$ microgram/kg/body weight, about $5\times10^1$ microgram/kg/body weight, about $6\times10^1$ microgram/kg/body weight, about $7\times10^1$ microgram/kg/body weight, about $8\times10^1$ microgram/kg/body weight, about $9\times10^1$ microgram/kg/body weight, about $1\times10^2$ microgram/kg/body weight, about $2\times10^2$ microgram/kg/body weight, about $3\times10^2$ microgram/kg/body weight, about $4\times10^2$ microgram/kg/body weight, about $5\times10^2$ microgram/kg/body weight, about $6\times10^2$ microgram/kg/body weight, about $7\times10^2$ microgram/kg/body weight, about $8\times10^2$ microgram/kg/body weight, about $9\times10^2$ microgram/kg/body weight, about $1\times10^3$ microgram/kg/body weight, about $2\times10^3$ microgram/kg/body weight, about $3\times10^3$ microgram/kg/body weight, about $4\times10^3$ microgram/kg/body weight, about $5\times10^3$ microgram/kg/body weight, about $6\times10^3$ microgram/kg/body weight, about $7\times10^3$ microgram/kg/body weight, about $8\times10^3$ microgram/kg/body weight, about $9\times10^3$ microgram/kg/body weight, about $1\times10^4$ microgram/kg/body weight, about $2\times10^4$ microgram/kg/body weight, about $3\times10^4$ microgram/kg/body weight, about $4\times10^4$ microgram/kg/body weight, about $5\times10^4$ microgram/kg/body weight, about $6\times10^4$ microgram/kg/body weight, about $7\times10^4$ microgram/kg/body weight, about $8\times10^4$ microgram/kg/body weight, about $9\times10^4$ microgram/kg/body weight, about $1\times10^5$ microgram/kg/body weight, about $2\times10^5$ microgram/kg/body weight, about $3\times10^5$ microgram/kg/body weight, about $4\times10^5$ microgram/kg/body weight, about $5\times10^5$ microgram/kg/body weight, about $6\times10^5$ microgram/kg/body weight, about $7\times10^5$ microgram/kg/body weight, about $8\times10^5$ microgram/kg/body weight, about $9\times10^5$ microgram/kg/body weight, about $1\times10^6$ microgram/kg/body weight, about $2\times10^6$ microgram/kg/body weight, about $3\times10^6$ microgram/kg/body weight, about $4\times10^6$ microgram/kg/body weight, about $5\times10^6$ microgram/kg/body weight, about $6\times10^6$ microgram/kg/body weight, about $7\times10^6$ microgram/kg/body weight, about $8\times10^6$ microgram/kg/body weight, about $9\times10^6$ microgram/kg/body weight, about $1\times10^7$ microgram/kg/body weight, about $2\times10^7$ microgram/kg/body weight, about $3\times10^7$ microgram/kg/body weight, about $4\times10^7$ microgram/kg/body weight, about $5\times10^7$ microgram/kg/body weight, about $6\times10^7$ microgram/kg/body weight, about $7\times10^7$ microgram/kg/body weight, about $8\times10^7$ microgram/kg/body weight, about $9\times10^7$ microgram/kg/body weight, about $1\times10^8$ microgram/kg/body weight, about $2\times10^8$ microgram/kg/body weight, about $3\times10^8$ microgram/kg/body weight, about $4\times10^8$ microgram/kg/body weight, about $5\times10^8$ microgram/kg/body weight, about $6\times10^8$ microgram/kg/body weight, about $7\times10^8$ microgram/kg/body weight, about $8\times10^8$ microgram/kg/body weight, about $9\times10^8$ microgram/kg/body weight, about $1\times10^9$ microgram/kg/body weight, about $2\times10^9$ microgram/kg/body weight, about $3\times10^9$ microgram/kg/body weight, about $4\times10^9$ microgram/kg/body weight, about $5\times10^9$ microgram/kg/body weight, about $6\times10^9$ microgram/kg/body weight, about $7\times10^9$ microgram/kg/body weight, about $8\times10^9$ microgram/kg/body weight, about $9\times10^9$ microgram/kg/body weight, about $1\times10^{10}$ microgram/kg/body weight, about $2\times10^{10}$ microgram/kg/body weight, about $3\times10^{10}$ microgram/kg/body weight, about $4\times10^{10}$ microgram/kg/body weight, about $5\times10^{10}$ microgram/kg/body weight, about $6\times10^{10}$ microgram/kg/body weight, about $7\times10^{10}$ microgram/kg/body weight, about $8\times10^{10}$ microgram/kg/body weight, or about $9\times10^{10}$ microgram/kg/body weight. In some embodiments, a dose may also comprise from $0.5\times10^1$ to $2\times10^1$ microgram/kg/body weight, from $1.5\times10^1$ to $3\times10^1$ microgram/kg/body weight, from $2.5\times10^1$ to $4\times10^1$ microgram/kg/body weight, from $3.5\times10^1$ to $5\times10^1$ microgram/kg/body weight, from $4.5\times10^1$ to $6\times10^1$ microgram/kg/body weight, from $5.5\times10^1$ to $7\times10^1$ microgram/kg/body weight, from $6.5\times10^1$ to $8\times10^1$ microgram/kg/body weight, from $7.5\times10^1$ to $9\times10^1$ microgram/kg/body weight, from $8.5\times10^1$ to $1\times10^1$ microgram/kg/body weight, from $0.5\times10^2$ to $2\times10^2$ microgram/kg/body weight, from $1.5\times10^2$ to $3\times10^2$ microgram/kg/body weight, from $2.5\times10^2$ to $4\times10^2$ microgram/kg/body weight, from $3.5\times10^2$ to $5\times10^2$ microgram/kg/body weight, from $4.5\times10^2$ to $6\times10^2$ microgram/kg/body weight, from $5.5\times10^2$ to $7\times10^2$ microgram/kg/body weight, from $6.5\times10^2$ to $8\times10^2$ microgram/kg/body weight, from $7.5\times10^2$ to $9\times10^2$ microgram/kg/body weight, from $8.5\times10^2$ to $1\times10^3$ microgram/kg/body weight, from $0.5\times10^3$ to $2\times10^3$ microgram/kg/body weight, from $1.5\times10^3$ to $3\times10^3$ microgram/kg/body weight, from $2.5\times10^3$ to $4\times10^3$ microgram/kg/body weight, from $3.5\times10^3$ to $5\times10^3$ microgram/kg/body weight, from $4.5\times10^3$ to $6\times10^3$ microgram/kg/body weight, from $5.5\times10^3$ to $7\times10^3$ microgram/kg/body weight, from $6.5\times10^3$ to $8\times10^3$ microgram/kg/body weight, from $7.5\times10^3$ to $9\times10^3$ microgram/kg/body weight, from $8.5\times10^3$ to $1\times10^4$ microgram/kg/body weight, from $0.5\times10^4$ to $2\times10^4$ microgram/kg/body weight, from $1.5\times10^4$ to $3\times10^4$ microgram/kg/body weight, from $2.5\times10^4$ to $4\times10^4$ microgram/kg/body weight, from $3.5\times10^4$ to $5\times10^4$ microgram/kg/body weight, from $4.5\times10^4$ to $6\times10^4$ microgram/kg/body weight, from $5.5\times10^4$ to $7\times10^4$ microgram/kg/body weight, from $6.5\times10^4$ to $8\times10^4$ microgram/kg/body weight, from $7.5\times10^4$ to $9\times10^4$ microgram/kg/body weight, from $8.5\times10^4$ to $1\times10^5$ microgram/kg/body weight, from $0.5\times10^5$ to $2\times10^5$ microgram/kg/body weight, from $1.5\times10^5$ to $3\times10^5$ microgram/kg/body weight, from $2.5\times10^5$ to $4\times10^5$ microgram/kg/body weight, from $3.5\times10^5$ to $5\times10^5$ microgram/kg/body weight, from $4.5\times10^5$ to $6\times10^5$ microgram/kg/body weight, from $5.5\times10^5$ to $7\times10^5$ microgram/kg/body weight, from $6.5\times10^5$ to $8\times10^5$ microgram/kg/body weight, from $7.5\times10^5$ to $9\times10^5$ microgram/kg/body weight, from $8.5\times10^5$ to $1\times10^6$ microgram/kg/body weight, from $0.5\times10^6$ to $2\times10^6$ microgram/kg/body weight, from $1.5\times10^6$ to $3\times10^6$ microgram/kg/body weight, from $2.5\times10^6$ to $4\times10^6$ microgram/kg/body weight, from $3.5\times10^6$ to $5\times10^6$ microgram/kg/body weight, from $4.5\times10^6$ to $6\times10^6$ microgram/kg/body weight, from $5.5\times10^6$ to $7\times10^6$ microgram/kg/body weight, from $6.5\times10^6$ to $8\times10^6$ microgram/kg/body weight, from $7.5\times10^6$ to $9\times10^6$ microgram/kg/body weight, from $8.5\times10^6$ to $1\times10^7$ microgram/kg/body weight, from $0.5\times10^7$ to $2\times10^7$ microgram/kg/body weight, from $1.5\times10^7$ to $3\times10^7$ microgram/kg/body weight, from $2.5\times10^7$ to $4\times10^7$ microgram/kg/body weight, from $3.5\times10^7$ to $5\times10^7$ microgram/kg/body weight, from $4.5\times10^7$ to $6\times10^7$ microgram/kg/body weight, from $5.5\times10^7$ to $7\times10^7$ microgram/kg/body weight, from $6.5\times10^7$ to $8\times10^7$ microgram/kg/body weight, from $7.5\times10^7$ to $9\times10^7$ microgram/kg/body weight, from $8.5\times10^7$ to $1\times10^8$ microgram/kg/body weight, from $0.5\times10^8$ to $2\times10^8$ microgram/kg/body weight, from $1.5\times10^8$ to $3\times10^8$ microgram/kg/body weight, from $2.5\times10^8$ to $4\times10^8$ microgram/kg/body weight, from $3.5\times10^8$ to $5\times10^8$ microgram/kg/body weight, from $4.5\times10^8$ to $6\times10^8$ microgram/kg/body weight, from $5.5\times10^8$ to $7\times10^8$ microgram/kg/body weight, from $6.5\times10^8$ to $8\times10^8$ microgram/kg/body weight, from $7.5\times10^8$ to $9\times10^8$ microgram/kg/body weight, from $8.5\times10^8$ to $1\times10^9$ microgram/kg/body weight, from $0.5\times10^9$ to $2\times10^9$ microgram/kg/body weight, from $1.5\times10^9$ to $3\times10^9$ microgram/kg/body weight, from $2.5\times10^9$ to $4\times10^9$ microgram/kg/body weight, from $3.5\times10^9$ to $5\times10^9$ microgram/kg/body weight, from $4.5\times10^9$ to $6\times10^9$ microgram/kg/body weight, from $5.5\times10^9$ to $7\times10^9$ microgram/kg/body weight, from $6.5\times10^9$ to $8\times10^9$ microgram/kg/body weight, from $7.5\times10^9$ to $9\times10^9$ microgram/kg/body weight, from $8.5\times10^9$ to $1\times10^{10}$ microgram/kg/body weight, from $0.5\times10^{10}$ to $2\times10^{10}$ microgram/kg/body weight, from $1.5\times10^{10}$ to $3\times10^{10}$ microgram/kg/body weight, from $2.5\times10^{10}$ to $4\times10^{10}$ microgram/kg/body weight, from $3.5\times10^{10}$ to $5\times10^{10}$ microgram/kg/body weight, from $4.5\times10^{10}$ to $6\times10^{10}$ microgram/kg/body weight, from $5.5\times10^{10}$ to $7\times10^{10}$ microgram/kg/body weight, from $6.5\times10^{10}$ to $8\times10^{10}$ microgram/kg/body weight, from $7.5\times10^{10}$ to $9\times10^{10}$ microgram/kg/body weight, or from $8.5\times10^{10}$ to $1\times10^{10}$ microgram/kg/body weight.

The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above.

Protein Purification

Protein purification techniques, in some instances, can comprise techniques involved, at one level, the homogenization and crude fractionation of the cells, tissue, or organ to polypeptide and non-polypeptide fractions. In some instances, the protein or polypeptide of interest may be further purified using chromatographic and electrophoretic techniques to achieve partial or complete purification (or purification to homogeneity) unless otherwise specified. In some cases, analytical methods particularly suited to the preparation of a pure peptide are ion-exchange chromatography, gel exclusion chromatography, polyacrylamide gel electrophoresis, affinity chromatography, immunoaffinity chromatography, and isoelectric focusing can also be used. In some case, a method of purifying peptides can be fast-performance liquid chromatography (FPLC) or even high-performance liquid chromatography (HPLC).

In some cases, a purified protein or peptide can comprise a composition, isolatable from other components, wherein the protein or peptide is purified to any degree relative to its naturally obtainable state. In other cases, an isolated or purified protein or peptide can also comprise a protein or peptide free from the environment in which it may naturally occur. In some cases, a purified protein can comprise a protein or peptide composition that has been subjected to fractionation to remove various other components, and which composition substantially retains its expressed biological activity. In other cases, a protein being purified can comprise a protein or peptide forming the major component of a composition. In some cases, a major component of a composition can comprise about 50%, about 60%, about 70%, about 80%, about 90%, about 95%, or more of the proteins in the composition.

Protein purification, in some cases, can comprise precipitation with ammonium sulphate, PEG, antibodies and the like, or by heat denaturation, followed by centrifugation; chromatography steps comprising ion exchange, gel filtration, reverse phase, hydroxyapatite, and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide are known to those of skill in the art in light of the present disclosure. These methods can, in some cases, comprise determining the specific activity of an active fraction, or assessing the amount of polypeptides within a fraction by SDS/PAGE analysis. In some cases, a method can comprise assessing the purity of a fraction is to calculate the specific activity of the fraction, to compare it to the specific activity of the initial extract, and to thus calculate the degree of purity therein, assessed by a "-fold purification number". The actual units used to represent the amount of activity, in some cases, can be dependent upon the particular assay technique chosen to follow the purification, and whether or not the expressed protein or peptide exhibits a detectable activity.

In some cases, a protein or peptide may not always be provided in its most purified state. In some cases, a less-than-most purified products may have utility in certain embodiments. In some cases, partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

In certain embodiments, a protein or peptide may be isolated or purified, for example, an MTAP or PEGylated MTAP polypeptide. For example, a His tag or an affinity epitope may be comprised in such an MTAP or PEGylated MTAP polypeptide to facilitate purification. Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that does not adsorb molecules to any significant extent and that has a broad range of chemical, physical, and thermal stability. The ligand should be coupled in such a way as to not affect its binding properties. The ligand should also provide relatively tight binding. It should be possible to elute the substance without destroying the sample or the ligand.

Size exclusion chromatography (SEC) is a chromatographic method in which molecules in solution are separated based on their size, or in more technical terms, their hydrodynamic volume. It is usually applied to large molecules or macromolecular complexes, such as proteins and industrial polymers. Typically, when an aqueous solution is used to transport the sample through the column, the technique is known as gel filtration chromatography, versus the name gel permeation chromatography, which is used when an organic solvent is used as a mobile phase.

The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together. Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

High-performance liquid chromatography (or high-pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

In some cases, any protein purification techniques well known to those of skill in the art not described herein and thereof can also be employed.

Pharmaceutical Compositions

In some instances, a pharmaceutical composition can increase a sensitivity to an immunotherapy. In some instances, a sensitivity to an immunotherapy increased by a pharmaceutical composition can comprise the effective amount, dose, or therapeutic or biological effect of the immunotherapy to a subject. In some instances, a sensitivity to an immunotherapy increased by a pharmaceutical composition can comprise measuring the effective amount, dose, or therapeutic or biological effect of the immunotherapy to a subject versus that of the immunotherapy to another subject without receiving the pharmaceutical composition. In some instances, a sensitivity to an immunotherapy increased by a pharmaceutical composition can comprise measuring the effective amount, dose, or therapeutic or biological effect of the immunotherapy to a subject versus that of the immunotherapy to the subject before receiving the pharmaceutical composition. In some cases, a pharmaceutical composition can increase a sensitivity to an immunotherapy by 10%, 20%, 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000%, 2000%, 3000%, 4000%, 5000%, 6000%, 7000%, 8000%, 9000%, 10000%, 20000%, 30000%, 40000%, 50000%, 60000%, 70000%, 80000%, 90000%, or 100000%. In some cases, a pharmaceutical composition can increase a sensitivity to an immunotherapy from 10 to 30%, from 20 to 40%, from 30 to 50%, from 40 to 60%, from 50 to 70%, from 60 to 80%, from 70 to 90%, from 80 to 100%, from 90 to 150%, from 100 to 200%, from 150 to 250%, from 200 to 300%, from 250 to 350%, from 300 to 400%, from 350 to 450%, from 400 to 500%, from 450 to 550%, from 500 to 600%, from 550 to 650%, from 600 to 700%, from 650 to 750%, from 700 to 800%, from 750 to 850%, from 800 to 900%, from 850 to 950%, from 900 to 1000%, from 950 to 2000%, from 1500 to 2500%, from 2000 to 3000%, from 2500 to 3500%, from 3000 to 4000%, from 3500 to 4500%, from 4000 to 5000%, from 4500 to 5500%, from 5000 to 6000%, from 5500 to 6500%, from 6000 to 7000%, from 6500 to 7500%, from 7000 to 8000%, from 7500 to 8500%, from 8000 to 9000%, from 8500 to 9500%, from 9000 to 10000%, from 9500 to 20000%, from 15000 to 25000%, from 20000 to 30000%, from 25000 to 35000%, from 30000 to 40000%, from 35000 to 45000%, from 40000 to 50000%, from 45000 to 55000%, from 50000 to 60000%, from 55000 to 65000%, from 60000 to 70000%, from 65000 to 75000%, from 70000 to 80000%, from 75000 to 85000%, from 80000 to 90000%, from 85000 to 95000%, or from 90000 to 100000%.

It is contemplated that an MTAP polypeptide can be administered systemically or locally. They can be administered using any routes described herein and thereof.

It is not intended that the present invention be limited by the particular nature of the therapeutic preparation. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects.

Such compositions are typically prepared as liquid solutions or suspensions, as injectables. Suitable diluents and excipients are, for example, water, saline, dextrose, glycerol, or the like, and combinations thereof. In addition, if desired, the compositions may contain minor amounts of auxiliary substances, such as wetting or emulsifying agents, stabilizing agents, or pH buffering agents.

Generally, pharmaceutical compositions may comprise an effective amount of one or more MTase or additional agents dissolved or dispersed in a pharmaceutically acceptable carrier. The phrases "pharmaceutical or pharmacologically acceptable" refers to molecular entities and compositions that do not produce an adverse, allergic, or other untoward reaction when administered to an animal, such as, for example, a human, as appropriate. The preparation of a pharmaceutical composition that contains at least one MTase isolated by the method disclosed herein, or additional active ingredient will be known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by the FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed., 1990, incorporated herein by reference). Except insofar as any conventional carrier is incompatible with the active ingredient, its use in the pharmaceutical compositions is contemplated.

Certain embodiments of the present invention may comprise different types of carriers depending on whether it is to be administered in solid, liquid, or aerosol form, and whether it needs to be sterile for the route of administration, such as injection. The compositions can be administered intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference).

The modified polypeptides may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine. Upon formulation, solutions will be administered in a manner compatible with the dosage formulation and in such amount as is therapeutically effective. The formulations are easily administered in a variety of dosage forms, such as formulated for parenteral administrations, such as injectable solutions, or aerosols for delivery to the lungs, or formulated for alimentary administrations, such as drug release capsules and the like.

Further in accordance with certain aspects of the present invention, the composition suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent, or carrier is detrimental to the recipient or to the therapeutic effectiveness of a composition contained therein, its use in administrable composition for use in practicing the methods is appropriate. Examples of carriers or diluents include fats, oils, water, saline solutions, lipids, liposomes, resins, binders, fillers, and the like, or combinations thereof. The composition may also comprise various antioxidants to retard oxidation of one or more component. Additionally, the prevention of the action of microorganisms can be brought about by preservatives, such as various antibacterial and antifungal agents, including but not limited to parabens (e.g., methylparabens, propylparabens), chlorobutanol, phenol, sorbic acid, thimerosal or combinations thereof.

In accordance with certain aspects of the present invention, the composition is combined with the carrier in any convenient and practical manner, i.e., by solution, suspension, emulsification, admixture, encapsulation, absorption, and the like. Such procedures are routine for those skilled in the art.

In a specific embodiment of the present invention, the composition is combined or mixed thoroughly with a semi-solid or solid carrier. The mixing can be carried out in any convenient manner, such as grinding. Stabilizing agents can be also added in the mixing process in order to protect the composition from loss of therapeutic activity, i.e., denaturation in the stomach. Examples of stabilizers for use in a composition include buffers, amino acids, such as glycine and lysine, carbohydrates, such as dextrose, mannose, galactose, fructose, lactose, sucrose, maltose, sorbitol, mannitol, etc.

In further embodiments, the present invention may concern the use of a pharmaceutical lipid vehicle composition that includes MTAP polypeptides, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man) However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods.

One of ordinary skill in the art would be familiar with the range of techniques that can be employed for dispersing a composition in a lipid vehicle. For example, the MTase or a fusion protein thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

Combination Treatments

In certain embodiments, the compositions and methods of the present embodiments involve administration of an MTAP polypeptide in combination with a second or additional therapy. The methods and compositions, including combination therapies, enhance the therapeutic or protective effect, and/or increase the therapeutic effect of another therapy. Therapeutic and prophylactic methods and compositions can be provided in a combined amount effective to achieve the desired effect. This process may involve administering both an MTAP polypeptide and a second therapy. A tissue, organ, or cell can be exposed to one or more compositions or pharmacological formulation(s) comprising one or more of the agents (i.e., an MTAP polypeptide or a second agent), or by contacting the tissue, organ, and/or cell with two or more distinct compositions or formulations, wherein one composition provides 1) an MTAP polypeptide, 2) a second agent, or 3) both an MTAP polypeptide and a second agent. Also, it is contemplated that such a combination therapy can be used in conjunction with surgical therapy.

An MTAP polypeptide may be administered before, during, after, or in various combinations relative to a second treatment. The administrations may be in intervals ranging from concurrently to minutes to days to weeks. In embodiments where the MTAP polypeptide is provided to a patient separately from a second agent, one would generally ensure that a significant period of time did not expire between the time of each delivery, such that the two treatments would still be able to exert an advantageously combined effect on the patient. In such instances, it is contemplated that one may provide a patient with the MTAP polypeptide and the second therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that the MTAP polypeptide may be given on any day of day 1 to day 90 (this such range includes intervening days) or any combination thereof, and another treatment is given on any day of day 1 to day 90 (this such range includes intervening days) or any combination thereof. Within a single day (24-hour period), the patient may be given one or multiple administrations of the treatment(s). Moreover, after a course of treatment, it is contemplated that there is a period of time at which no treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an MTAP polypeptide is "A" and a second therapy is "B":

| | | | | | | |
|---|---|---|---|---|---|---|
| A/B/A | B/A/B | B/B/A | A/A/B | A/B/B | B/A/A | A/B/B/B B/A/B/B |
| B/B/B/A | B/B/A/B | A/A/B/B | A/B/A/B | A/B/B/A | B/B/A/A | |
| B/A/B/A | B/A/A/B | A/A/A/B | B/A/A/A | A/B/A/A | A/A/B/A | |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Immunotherapy

The skilled artisan will understand that immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T-cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Immune checkpoints either turn up a signal (e.g., co-stimulatory molecules) or turn down a signal Immune checkpoint proteins that may be targeted by immune checkpoint blockade include adenosine A2A receptor (A2AR), B7-H3 (also known as CD276), B and T lymphocyte attenuator (BTLA), CCL5, CD27, CD38, CD8A, CMKLR1, cytotoxic T-lymphocyte-associated protein 4 (CTLA-4, also known as CD152), CXCL9, CXCR5, glucocorticoid-induced tumour necrosis factor receptor-related protein (GITR), HLA-DRB1, ICOS (also known as CD278), HLA-DQA1, HLA-E, indoleamine 2,3-dioxygenase 1 (ID01), killer-cell immunoglobulin (KIR), lymphocyte activation gene-3 (LAG-3, also known as CD223), Mer tyrosine kinase (MerTK), NKG7, OX40 (also known as CD134), programmed death 1 (PD-1), programmed death-ligand 1 (PD-L1, also known as CD274), PDCD1LG2, PSMB10, STAT1, T-cell immunoreceptor with Ig and ITIM domains (TIGIT), T-cell immunoglobulin domain and mucin domain 3 (TIM-3), V-domain Ig suppressor of T-cell activation (VISTA, also known as C10orf54), and 4-1BB (CD137). In particular, the immune checkpoint inhibitors target the PD-1 axis and/or CTLA-4.

The immune checkpoint inhibitors may be drugs, such as small molecules, recombinant forms of ligand or receptors, or antibodies, such as human antibodies (e.g., International Patent Publication WO2015/016718; Pardoll, Nat Rev Cancer, 12(4): 252-264, 2012; both incorporated herein by reference). Known inhibitors of the immune checkpoint proteins or analogs thereof may be used, in particular chimerized, humanized, or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

In some embodiments, a PD-1 binding antagonist is a molecule that inhibits the binding of PD-1 to its ligand binding partners. In a specific aspect, the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, a PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or an oligopeptide. Exemplary antibodies are described in U.S. Pat. Nos. 8,735,553, 8,354,509, and 8,008,449, all of which are incorporated herein by reference. Other PD-1 axis antagonists for use in the methods provided herein are known in the art, such as described in U.S. Patent Application Publication Nos. 2014/0294898, 2014/022021, and 2011/0008369, all of which are incorporated herein by reference.

In some embodiments, a PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence)). In some embodiments, the PD-1 binding antagonist is AMP-224. Nivolumab, also known as MDX-1106-04, MDX-1106, ONO-4538, BMS-936558, and OPDIVO, is an anti-PD-1 antibody described in WO2006/121168. Pembrolizumab, also known as MK-3475, Merck 3475, lambrolizumab, KEYTRUDA, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342.

Another immune checkpoint protein that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T-cells and acts as an "off" switch when bound to CD80 or CD86 on the surface of antigen-presenting cells. CTLA-4 is similar to the T-cell co-stimulatory protein, CD28, and both molecules bind to CD80 and CD86, also called B7-1 and B7-2 respectively, on antigen-presenting cells. CTLA-4 transmits an inhibitory signal to T-cells, whereas CD28 transmits a stimulatory signal. Intracellular CTLA-4 is also found in regulatory T-cells and may be important to their function. T-cell activation through the T-cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide. Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in U.S. Pat. No. 8,119,129; PCT Publn. Nos. WO 01/14424, WO 98/42752, WO 00/37504 (CP675, 206, also known as tremelimumab; formerly ticilimumab); U.S. Pat. No. 6,207,156; Hurwitz et al. (1998) *Proc Natl Acad Sci USA*, 95(17): 10067-10071; Camacho et al. (2004) *J Clin Oncology*, 22(145): Abstract No. 2505 (antibody CP-675206); and Mokyr et al. (1998) *Cancer Res*, 58:5301-5304 can be used in the methods disclosed herein. The teachings of each of the aforementioned publications are hereby incorporated by reference. Antibodies that compete with any of these art-recognized antibodies for binding to CTLA-4 can also be used. For example, a humanized CTLA-4 antibody is described in International Patent Application No. WO2001/014424, WO2000/037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2, and CDR3 domains of the VL region of ipilimumab. In another embodiment, the antibody competes for binding with and/or binds to the same epitope on CTLA-4 as the above-mentioned antibodies. In another embodiment, the antibody has an at least about 90% variable region amino acid sequence identity with the above-mentioned antibodies (e.g., at least about 90%, 95%, or 99% variable region identity with ipilimumab). Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

Another immune checkpoint protein that can be targeted in the methods provided herein is lymphocyte-activation gene 3 (LAG-3), also known as CD223. The complete protein sequence of human LAG-3 has the Genbank accession number NP-002277. LAG-3 is found on the surface of activated T-cells, natural killer cells, B cells, and plasmacytoid dendritic cells. LAG-3 acts as an "off" switch when bound to MHC class II on the surface of antigen-presenting cells. Inhibition of LAG-3 both activates effector T-cells and inhibitor regulatory T-cells. In some embodiments, the immune checkpoint inhibitor is an anti-LAG-3 antibody (e.g., a human antibody, a humanized antibody, or a chimeric antibody), an antigen binding fragment thereof, an immunoadhesin, a fusion protein, or oligopeptide. Anti-human-LAG-3 antibodies (or VH and/or VL domains derived therefrom) suitable for use in the present methods can be generated using methods well known in the art. Alternatively, art recognized anti-LAG-3 antibodies can be used. An exemplary anti-LAG-3 antibody is relatlimab (also known as BMS-986016) or antigen binding fragments and variants thereof (see, e.g., WO 2015/116539). Other exemplary anti-LAG-3 antibodies include TSR-033 (see, e.g., WO 2018/201096), MK-4280, and REGN3767. MGD013 is an anti-LAG-3/PD-1 bispecific antibody described in WO 2017/019846. FS118 is an anti-LAG-3/PD-L1 bispecific antibody described in WO 2017/220569.

Another immune checkpoint protein that can be targeted in the methods provided herein is V-domain Ig suppressor of T-cell activation (VISTA), also known as C10orf54. The complete protein sequence of human VISTA has the Genbank accession number NP_071436. VISTA is found on white blood cells and inhibits T-cell effector function. In some embodiments, the immune checkpoint inhibitor is an anti-VISTAS antibody (e.g., a human antibody, a humanized antibody, or a chimeric antibody), an antigen binding fragment thereof, an immunoadhesin, a fusion protein, or oligopeptide. Anti-human-VISTA antibodies (or VH and/or VL domains derived therefrom) suitable for use in the present methods can be generated using methods well known in the art. Alternatively, art recognized anti-VISTA antibodies can be used. An exemplary anti-VISTA antibody is JNJ-61610588 (also known as onvatilimab) (see, e.g., WO 2015/097536, WO 2016/207717, WO 2017/137830, WO 2017/175058). VISTA can also be inhibited with the small molecule CA-170, which selectively targets both PD-L1 and VISTA (see, e.g., WO 2015/033299, WO 2015/033301).

Another immune checkpoint protein that can be targeted in the methods provided herein is indoleamine 2,3-dioxygenase (IDO). The complete protein sequence of human IDO has Genbank accession number NP_002155. In some embodiments, the immune checkpoint inhibitor is a small molecule IDO inhibitor. Exemplary small molecules include BMS-986205, epacadostat (INCB24360), and navoximod (GDC-0919).

Another immune checkpoint protein that can be targeted in the methods provided herein is CD38. The complete protein sequence of human CD38 has Genbank accession number NP_001766. In some embodiments, the immune checkpoint inhibitor is an anti-CD38 antibody (e.g., a human antibody, a humanized antibody, or a chimeric antibody), an antigen binding fragment thereof, an immunoadhesin, a fusion protein, or oligopeptide. Anti-human-CD38 antibodies (or VH and/or VL domains derived therefrom) suitable for use in the present methods can be generated using methods well known in the art. Alternatively, art recognized anti-CD38 antibodies can be used. An exemplary anti-CD38 antibody is daratumumab (see, e.g., U.S. Pat. No. 7,829,673).

Another immune checkpoint protein that can be targeted in the methods provided herein is ICOS, also known as CD278. The complete protein sequence of human ICOS has Genbank accession number NP_036224. In some embodiments, the immune checkpoint inhibitor is an anti-ICOS antibody (e.g., a human antibody, a humanized antibody, or a chimeric antibody), an antigen binding fragment thereof, an immunoadhesin, a fusion protein, or oligopeptide. Anti-human-ICOS antibodies (or VH and/or VL domains derived therefrom) suitable for use in the present methods can be generated using methods well known in the art. Alternatively, art recognized anti-ICOS antibodies can be used. Exemplary anti-ICOS antibodies include JTX-2011 (see, e.g., WO 2016/154177, WO 2018/187191) and GSK3359609 (see, e.g., WO 2016/059602).

Another immune checkpoint protein that can be targeted in the methods provided herein is T-cell immunoreceptor with Ig and ITIM domains (TIGIT). The complete protein sequence of human TIGIT has Genbank accession number NP_776160. In some embodiments, the immune checkpoint inhibitor is an anti-TIGIT antibody (e.g., a human antibody, a humanized antibody, or a chimeric antibody), an antigen binding fragment thereof, an immunoadhesin, a fusion protein, or oligopeptide. Anti-human-TIGIT antibodies (or VH and/or VL domains derived therefrom) suitable for use in the present methods can be generated using methods well known in the art. Alternatively, art recognized anti-TIGIT antibodies can be used. An exemplary anti-TIGIT antibody is MK-7684 (see, e.g., WO 2017/030823, WO 2016/028656).

Another immune checkpoint protein that can be targeted in the methods provided herein is OX40, also known as CD134. The complete protein sequence of human OX40 has Genbank accession number NP_003318. In some embodiments, the immune checkpoint inhibitor is an anti-OX40 antibody (e.g., a human antibody, a humanized antibody, or a chimeric antibody), an antigen binding fragment thereof, an immunoadhesin, a fusion protein, or oligopeptide. Anti-human-OX40 antibodies (or VH and/or VL domains derived therefrom) suitable for use in the present methods can be generated using methods well known in the art. Alternatively, art recognized anti-OX40 antibodies can be used. An exemplary anti-OX40 antibody is PF-04518600 (see, e.g., WO 2017/130076). ATOR-1015 is a bispecific antibody targeting CTLA4 and OX40 (see, e.g., WO 2017/182672, WO 2018/091740, WO 2018/202649, WO 2018/002339).

Another immune checkpoint protein that can be targeted in the methods provided herein is glucocorticoid-induced tumour necrosis factor receptor-related protein (GITR), also known as TNFRSF18 and AITR. The complete protein sequence of human GITR has Genbank accession number NP_004186. In some embodiments, the immune checkpoint inhibitor is an anti-GITR antibody (e.g., a human antibody, a humanized antibody, or a chimeric antibody), an antigen binding fragment thereof, an immunoadhesin, a fusion protein, or oligopeptide. Anti-human-GITR antibodies (or VH and/or VL domains derived therefrom) suitable for use in the present methods can be generated using methods well known in the art. Alternatively, art recognized anti-GITR antibodies can be used. An exemplary anti-GITR antibody is TRX518 (see, e.g., WO 2006/105021).

Another immune checkpoint protein that can be targeted in the methods provided herein is T-cell immunoglobulin and mucin-domain containing-3 (TIM3), also known as HAVCR2. The complete protein sequence of human TIM3 has Genbank accession number NP_116171. In some embodiments, the immune checkpoint inhibitor is an anti-TIM3 antibody (e.g., a human antibody, a humanized antibody, or a chimeric antibody), an antigen binding fragment thereof, an immunoadhesin, a fusion protein, or oligopeptide. Anti-human-TIM3 antibodies (or VH and/or VL domains derived therefrom) suitable for use in the present methods can be generated using methods well known in the art. Alternatively, art recognized anti-TIM3 antibodies can be used. Exemplary anti-TIM3 antibodies include LY3321367 (see, e.g., WO 2018/039020), MBG453 (see, e.g., WO 2015/117002) and TSR-022 (see, e.g., WO 2018/085469).

Another immune checkpoint protein that can be targeted in the methods provided herein is 4-1BB, also known as CD137, TNFRSF9, and ILA. The complete protein sequence of human 4-1BB has Genbank accession number NP_001552. In some embodiments, the immune checkpoint inhibitor is an anti-4-1BB antibody (e.g., a human antibody, a humanized antibody, or a chimeric antibody), an antigen binding fragment thereof, an immunoadhesin, a fusion protein, or oligopeptide. Anti-human-4-1BB antibodies (or VH and/or VL domains derived therefrom) suitable for use in the present methods can be generated using methods well known in the art. Alternatively, art recognized anti-4-1BB antibodies can be used. An exemplary anti-4-1BB antibody is PF-05082566 (utomilumab; see, e.g., WO 2012/032433).

In some embodiment, the immune therapy could be adoptive immunotherapy, which involves the transfer of autologous antigen-specific T-cells generated ex vivo. The T-cells used for adoptive immunotherapy can be generated either by expansion of antigen-specific T-cells or redirection of T-cells through genetic engineering (Park, Rosenberg et al. 2011). Isolation and transfer of tumor specific T-cells has been shown to be successful in treating melanoma. Novel specificities in T-cells have been successfully generated through the genetic transfer of transgenic T-cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. CARs have successfully allowed T-cells to be redirected against antigens expressed at the surface of tumor cells from various malignancies including lymphomas and solid tumors (Jena, Dotti et al. 2010).

In one embodiment, the present application provides for a combination therapy for the treatment of cancer wherein the combination therapy comprises adoptive T-cell therapy and a checkpoint inhibitor. In one aspect, the adoptive T-cell therapy comprises autologous and/or allogeneic T-cells. In another aspect, the autologous and/or allogeneic T-cells are targeted against tumor antigens. The MTAP polypeptide may be administered to the patient prior to and/or simultaneously with the administration of the adoptive T-cell therapy. In another aspect, the autologous and/or allogeneic T-cells may be engineered to express the MTAP polypeptide.

Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

Kits

Certain aspects of the present invention may provide kits, such as therapeutic kits. For example, a kit may comprise one or more pharmaceutical composition as described herein and optionally instructions for their use. Kits may also comprise one or more devices for accomplishing administration of such compositions. For example, a subject kit may comprise a pharmaceutical composition and catheter for accomplishing direct intravenous injection of the composition into a cancerous tumor. In other embodiments, a subject kit may comprise pre-filled ampoules of an MTAP polypeptide, optionally formulated as a pharmaceutical, or lyophilized, for use with a delivery device.

Kits may comprise a container with a label. Suitable containers include, for example, bottles, vials, and test tubes. The containers may be formed from a variety of materials, such as glass or plastic. The container may hold a composition that includes an MTAP polypeptide that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Defined PEGylation and its Impact on the Pharmacological Kinetics of an MTAP Polypeptide from *Homo sapiens*

Provided herein are MTAP polypeptides and MTAP polypeptides conjugated to PEG.

The *Homo sapiens* MTAP (hs-MTAP) enzyme (SEQ ID NO: 1) was purified. A DNA construct comprising an open reading from encoding the MTAP enzyme from *Homo sapiens* MTAP was constructed by overlap extension polymerase chain reaction (PCR) of an *E. coli* codon-optimized gene block designed using IDT software. The full-length gene includes an N-terminal NcoI restriction-enzyme cleavage site, an N-terminal His6 tag, an *E. coli* codon-optimized hs-MTAP gene, a stop codon, and a C-terminal EcoRI restriction-enzyme cleavage site. The aforementioned restriction sites were used to clone the assembled DNA construct into a pET-28a+ vector (Novagen). This construct was then used to transform BL21 (DE3) *E. coli* for expression. Cells were grown at 37° C. with shaking at 210 rpm in Terrific Broth (TB) media with 50 mg/L of kanamycin. Expression was induced when an $OD_{600}$~1.0 was reached by adding IPTG (0.5 mM final concentration) with continued shaking overnight at 37° C. Cells were then harvested by centrifugation and re-suspended in lysis buffer containing 50 mM sodium phosphate (pH 7.4), 300 mM NaCl, 1 mM phenylmethylsulfonylfluoride, and 1 µg/mL DNase. Lysis was achieved by French press, and the lysate was cleared of particulates by centrifuging at 20,000×g for 1 h at 4° C. The supernatant was then filtered through a 5 µm syringe filter and applied to a Ni-NT A/agarose column (Qiagen) pre-equilibrated in 50 mM sodium phosphate (pH 7.4), 300 mM NaCl buffer. After loading the lysate onto the column, the resin was washed with 5 column volumes (CV) of 50 mM sodium phosphate (pH 7.4), 300 mM NaCl, 20 mM imidazole buffer. Next the flow rate was set to slowly wash the column with 100 CV of endotoxin-free PBS (Corning) containing 1% v/v Triton-Xll4 in order to remove any lipopolysaccharide (LPS or endotoxin), which is a typical contaminant of bacterial expression systems. The washed enzyme was then eluted in 5 CV of endotoxin-free PBS with 250 mM imidazole, and the resin was rinsed with a second 5 CV portion of endotoxin-free PBS. At this point, enzyme was buffer exchanged into fresh PBS to remove imidazole, and 10% glycerol was added. Aliquots were flash frozen in liquid nitrogen for storage at −80° C. Alternatively, enzyme was immediately buffer exchanged into freshly made, sterile 100 mM sodium phosphate (pH 8.4) to both remove imidazole and prepare it for PEGylation. Enzyme purities were typically >95% based on SDS-PAGE analysis, and typical yields averaged around 65 mg/L of culture. Protein quantities were assessed by measuring Abs280 nm and using the calculated enzyme extinction coefficient of 29,950 $M^{-1}$ $cm^{-1}$.

The purified, endotoxin-free hs-MTAP polypeptide was thoroughly buffer-exchanged into freshly prepared 100 mM sodium phosphate (pH 8.4) and concentrated to 5 mg/mL. The resultant solution was mixed with a 10×, 20×, 50×, or 100× molar excess of solid Methoxyl PEG Succinimidyl Carbonate 5000 MW (NOF Corporation), and allowed to react at room temperature for 1 h. Un-reacted PEG was removed from solution by thorough buffer exchange into fresh, endotoxin-free PBS in a 100 kDa cut-off centrifugal filtration device (Amicon). Endotoxin levels were quantified using the Chromo-LAL kinetic chromogenic endotoxin testing kit (Associates of Cape Cod, Inc.). Enzyme washed in the manner described above typically resulted in endotoxin levels <10 EU/mg of purified hs-MTAP.

The PEGylated material was examined by SDS-PAGE and gel densitometry to determine the extent of PEGylation for each reaction condition, as shown in FIG. 1A. Under these conditions, the ratio of PEG to hs-MTAP was found to follow a Gaussian distribution. The 10× prep displayed a mode of ~2 PEG molecules per subunit, the 20× prep displayed a mode of ~4 PEG molecules per subunit, the 50× prep displayed a mode of ~6 PEG molecules per subunit, and the 100× prep displayed a mode of ~8 PEG molecules per subunit.

Figure 1B:
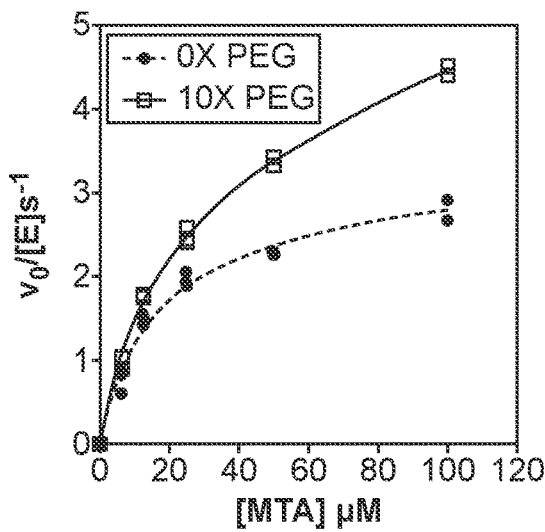
Figure 1C:
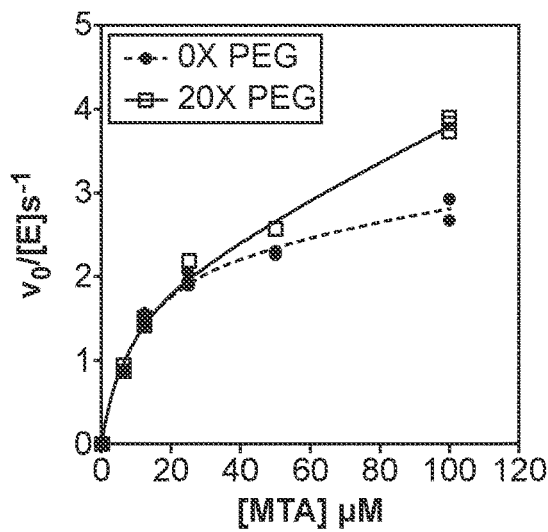
Figure 1D:
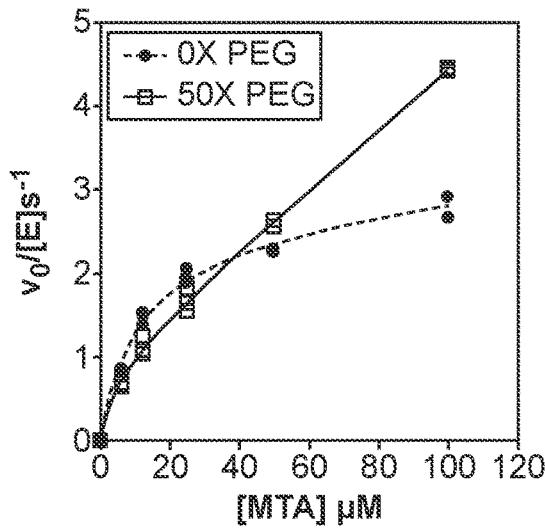
Figure 1E:
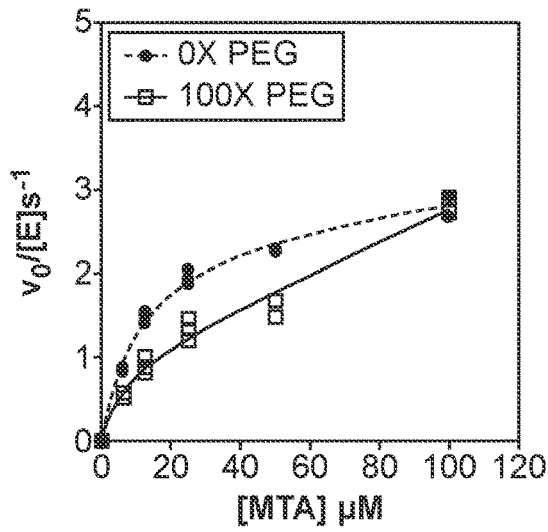

The kinetics for native hs-MTAP and each of the differentially PEGylated hs-MTAP preparations, as defined by molar fold PEG excess (i.e. 0×, 10×, 20×, 50×, and 100×), were quantified by a spectrophotometric assay as a function of time and substrate concentration, as described elsewhere (Singh, Shi et al. 2004). The resulting data was fit to the Michaelis-Menten equation with an additional $2^{nd}$ order rate constant to describe the biphasic linear rates observed at higher substrate concentrations. Under these conditions, the 10× and 20× preps displayed well preserved kinetic activity at all tested substrate concentrations, as shown in FIGS. 1B & 1C. The 50× and 100× preps display decreased activity at lower substrate concentrations, when compared to the 0× prep, as shown in FIGS. 1D & 1E.

PEGylation kinetics are governed by buffer composition and pH, and by the concentrations of PEG and protein reactants. The primary amine conjugating PEG reagents are readily hydrolyzed non-enzymatically; thus, there is a requirement for large molar excesses of PEG to enable lysine modification. PEGylation kinetics will also depend somewhat on the number of lysine residues found within a protein and their local environment wherein surface exposed lysine residues will react more readily than buried residues. A simple empirical process is therefore developed for a given protein being PEGylated wherein reaction conditions are used with defined protein and PEG concentrations with a defined buffer composition at a defined pH such that a desired distribution of PEG is reliably achieved.

Taking all of these data under consideration, a preferred embodiment for the PEGylation of wild-type hs-MTAP (SEQ ID NO: 1) that preserves high catalytic rates at substrate concentration ranges between 0-25 µM are formulations that have a defined number of PEGylation events following a Gaussian distribution, where ≥80% of the protein contains of 1, 2, 3, 4, or 5 PEG molecules per subunit with a mode of 3±1 PEG molecules, and about 20% of the protein has 0, 6, 7, 8 or more PEG molecule.

Example 2: Defined PEGylation and its Impact of the Pharmacological Kinetics of Two MTAP Polypeptide Variants from *Homo sapiens*

Figure 2A:
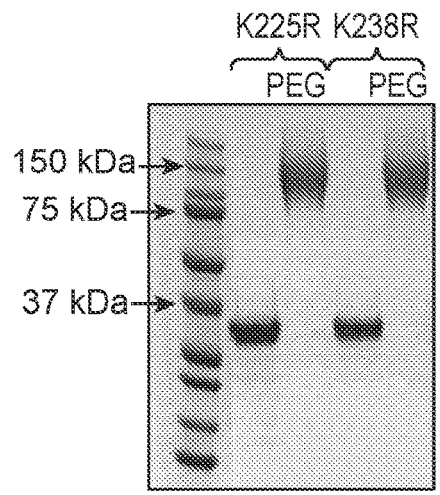
FIGS. 2A-C. Defined PEGylation and its impact on the enzyme kinetics of two variants of *Homo sapiens* MTAP polypeptide that retain high catalytic activity when conjugated to more than 5 PEG moieties.
Figure 2B:
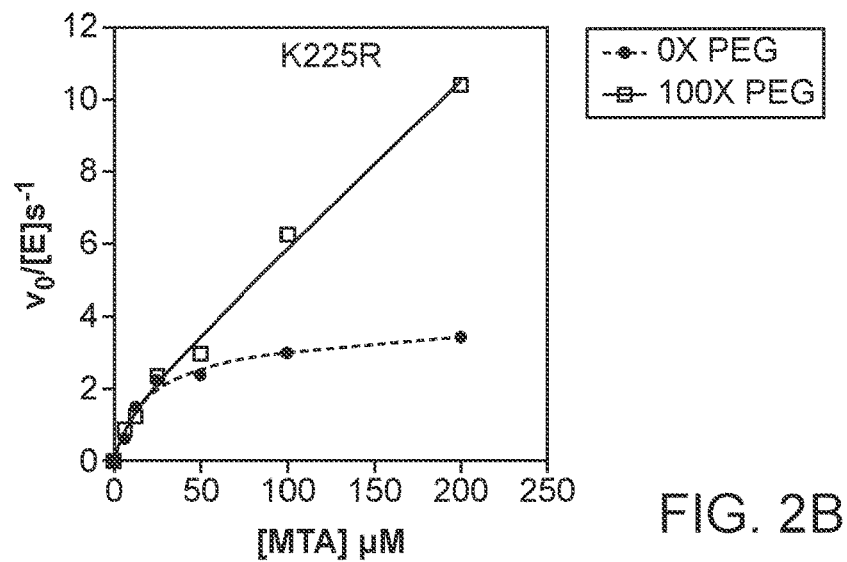
Figure 2C:
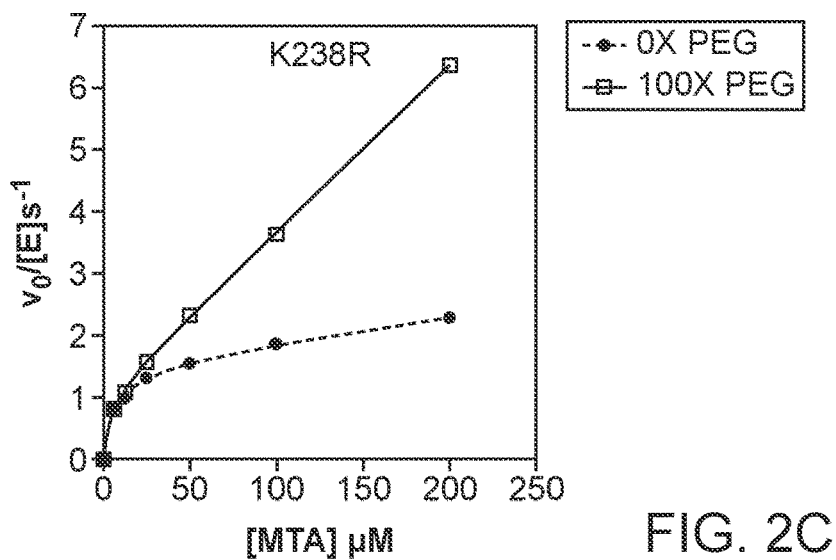

The gene coding for the hs-MTAP polypeptide (SEQ ID NO: 1) was used as a starting point to generate variants with improvements in enzymatic activity at high PEG:protein ratios. PEGylation covalently modifies hs-MTAP lysine residues and extensive PEGylation negatively effects enzyme kinetics, suggesting that PEG conjugation of specific lysine residues near the active site may affect domain movements important to catalysis. Several lysine residues located on loops near the active site were singly mutated to arginine residues by overlap extension PCR. The final assembled PCR products were digested with NcoI and EcoRI and ligated into pET28a vector using T4 DNA ligase. Each of the variants was subsequently expressed, purified, and conjugated to 100× fold molar excess of solid Methoxyl PEG Succinimidyl Carbonate 5000 MW (NOF Corporation) as described previously. The reaction kinetics for these variants was determined for both the native and 100× PEGylated forms of the enzyme. Two variants were identified (K225R, SEQ ID NO: 3; and K238R, SEQ ID NO: 5) that even when extensively PEGylated (FIG. 2A) retained high $k_{cat}/K_m$ at all substrate concentrations (FIGS. 2B & 2C). The $k_{cat}/K_m$ of MTAP-K225R is $1.9 \times 10^5$ $M^{-1}s^{-1}$. The $k_{cat}/K_m$ of MTAP-K238R is $2.3 \times 10^5$ $M^{-1}s^{-1}$. The $k_{cat}/K_m$ of 100× PEGylated MTAP-K225R is $1.9 \times 10^5$ $M^{-1}s^{-1}$. The $k_{cat}/K_m$ of 100× PEGylated MTAP-K238R is $2.3 \times 10^5$ $M^{-1}s^{-1}$.

The hs-MTAP-K225R and hs-MTAP-K238R variants therefore represent improvements upon the wild-type enzyme in that formulation by lysine PEGylation to improve in vivo stability can be implemented at any desired amount of PEG conjugation without compromising catalytic activity.

Figure 3A:
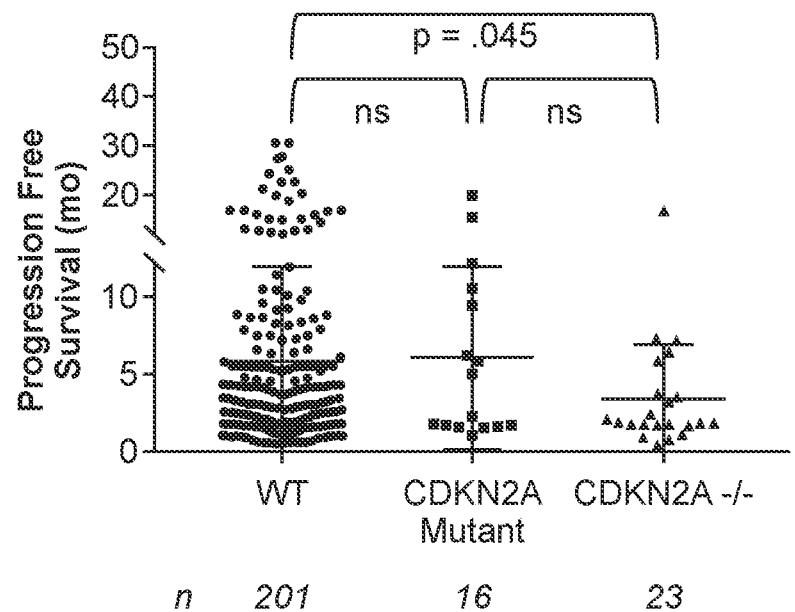
FIGS. 3A-B. The role of MTAP and CDKN2A in cancer and immunosuppression.
Figure 3B:
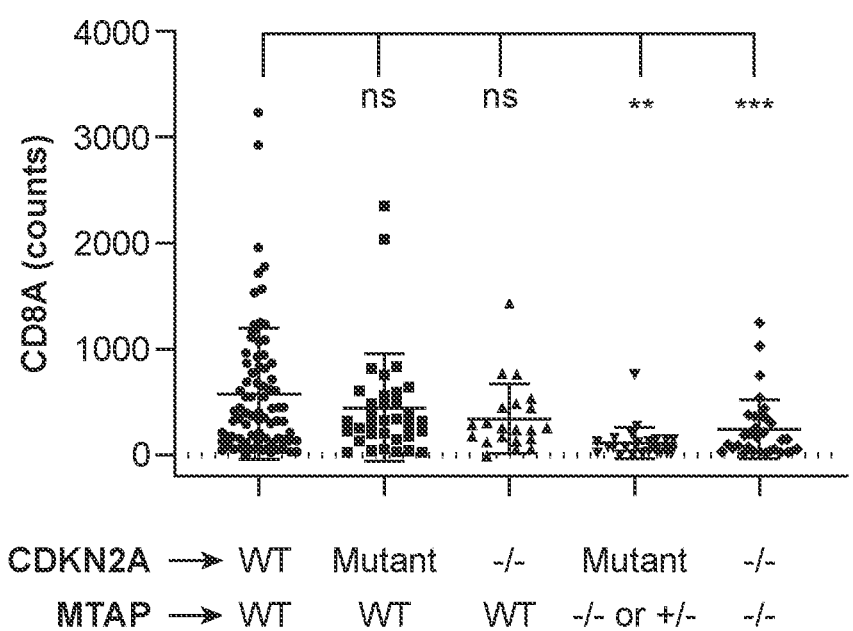

Example 3: MTAP Mutations in Cancer are Associated with Reduced T-Cell Infiltration and Resistance to Immunotherapy Methylthioadenosine phosphorylase (MTAP) is a housekeeping enzyme that uses methylthioadenosine (MTA) for methionine and purine salvage. Chromosomal deletion of the MTAP gene at 9p21 occurs in approximately 15% of all human cancers and is accompanied by reduced levels of tumor immune cell infiltrate and lower overall survival. The MTAP locus lies adjacent to the CDKN2A cell cycle inhibitor gene. Deletion of CDKN2A is associated with reduced progression free survival in non-small cell lung cancer patients treated with anti-PD-L1. FIG. 3A. See Rizvi et al. J Clin Oncol 2018. CDKN2A deletion is also associated with resistance to anti PDL-1 treatment in patients with advanced urothelial carcinoma (Nassar et al, Br. J. Cancer, 2020) and resistance to anti-CTLA4 therapy (ipilimumab) in melanoma patients (Gao et al, Cell, 2016). The CDKN2A mutation was originally thought responsible for the cancer phenotypes associated with 9p21.3 deletions, with MTAP as a bystander co-deletion. However, increasing evidence suggests that the MTAP deletion can act independently of CDKN2 in tumor formation or promotion. As shown in FIG. 3B, homozygous or heterozygous deletion of MTAP, significantly decreased the activation of the immune system, as measured by the counts of CD8A, and acts independently of CDKN2 deletion. MTAP deletion also results in an increase in extracellular MTA levels. Indeed, cancer cell lines with the MTAP deletion produced a higher amount of MTA in the culture media when compared to the ones without the deletion. See Marjon et al. Cell Report 2016. One hypothesis to explain these results is that extracellular MTA released by MTAP−/− cancer cells inhibits the PRMT5 arginine methyltransferase in T-cells, leading to the immunosuppression (Henrich et al, Oncoimmunology. 2016; Strobl et al, Molecular Cancer Therapeutics, 2020).

Figure 4A:
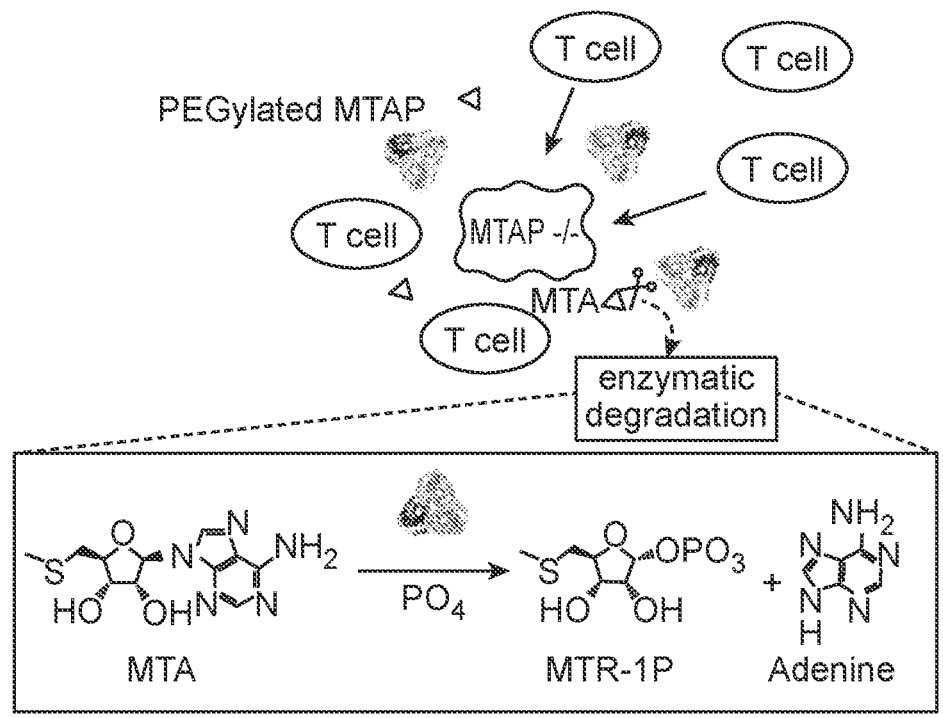
FIGS. 4A-B. Cancer therapy with MTAP polypeptides.
Figure 4B:
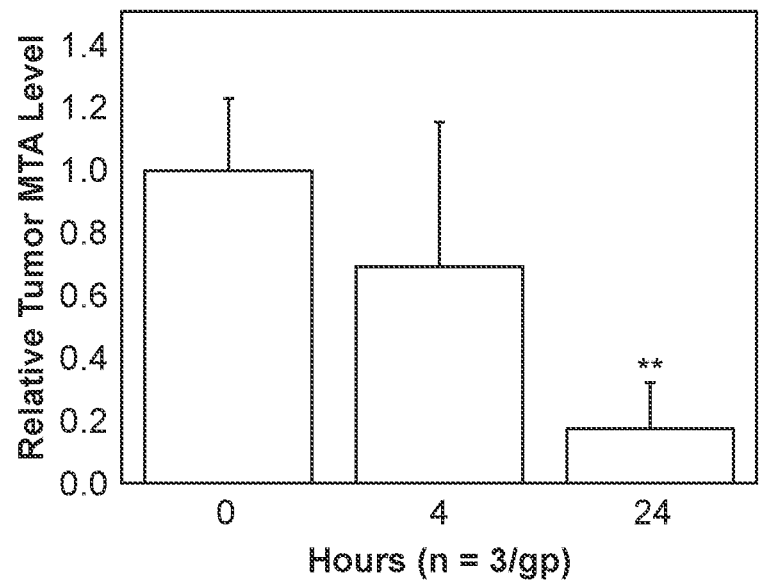

Based on these data, it proposed to treat MTAP-deficient cancers with recombinant, PEG-conjugated MTAP. As shown in FIG. 4A, the PEGylated MTAP metabolizes extracellular MTA released by a cancer cell with an MTAP deletion, yielding methylthioribose-1 phosphate (MTR-1-P) and adenine. The resulting reduction in extracellular MTA eliminates the inhibition of PRMT5 in T-cells, allowing them to be activated and target the cancer. Indeed, addition of recombinant MTAP polypeptides into tumor-bearing mice decreased extracellular MTA level by about 80% over 24 hours, as shown in FIG. 4B. These results suggest that administering exogenous MTAP may be an effective targeted therapy for treating cancers with elevated MTA levels resulting from an MTAP deletion at 9p23.1 or other reduction in MTAP activity.

Example 4: Cancer Therapy with PEGylated MTAP

B16-F10 melanoma cells were used to create a MTAP−/− cell line model to study the biological function of MTAP and the consequence of MTA accumulation both metabolically to the tumor and upon the host immune system. Cas9 protein (TrueCut™ Cas9 Protein v2) and synthetic single guide RNA purchased through ThermoFisher were transfected into wildtype B16-F10 cells using lypofectamine (Lipofectamine™ CRISPRMAX™ Cas9 Transfection Reagent). Two days after transfection, cells were plated using limited dilution method into ten 96-well plates. Plates were examined daily for single cell clones. After reaching confluency (10-14 days post transfection), the identified single cell clones were expanded and analyzed for MTAP expression through Western blotting or Q-PCR. Clones lacking any MTAP expression were verified for gene disruption by cloning and sequencing. The MTAP deletion cell line can be used in any methods or assays for analyzing the activity, biochemical or biological, of the MTAP gene described herein and thereof.

Figure 5A:
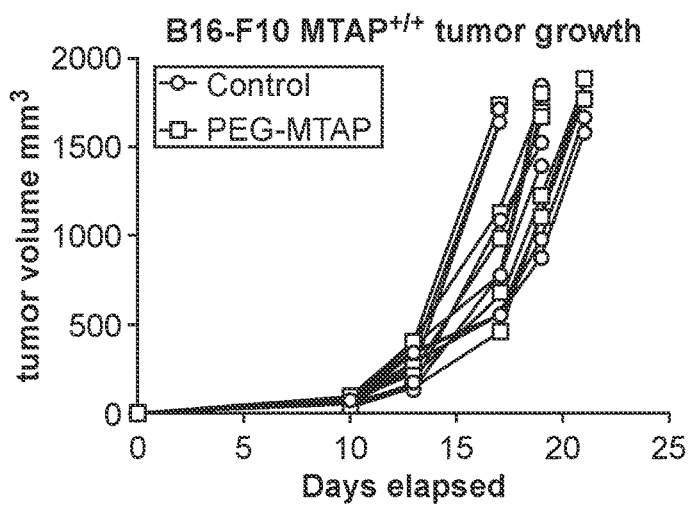
FIGS. 5A-C. Therapeutic potential of PEGylated-MTAP polypeptides in targeted cancer therapy.
Figure 5B:
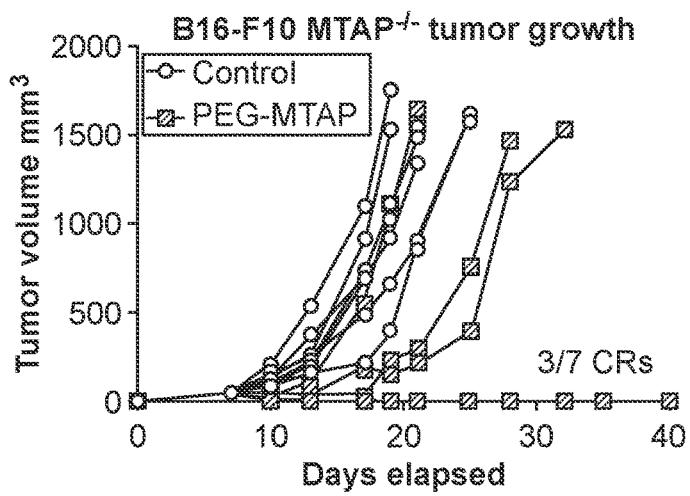
Figure 5C:
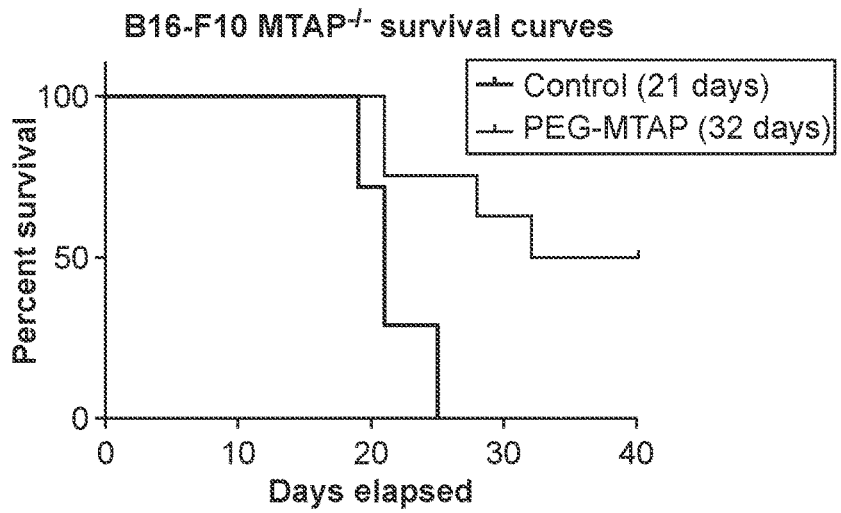

Treatment with PEGylated MTAP polypeptide is effective against tumors with an MTAP deletion. Two cohorts each of C57/BL6 mice were subcutaneously inoculated with either 5×10^4 wildtype B16-F10 melanoma cells or B16-F10 melanoma cells with an MTAP deletion. When the tumors reached a mean size of 55 mm³, the mice were treated with either vehicle (PBS) or 50 mg/kg of a PEG-MTAP polypeptide three times/week by peri-tumoral injection for 2 weeks. PEG-MTAP had little effect on control MTAP+/+ tumors but significantly inhibited the growth of MTAP−/− tumors, as shown in FIGS. 5A & 5B. Indeed, a complete remission (CR) was observed in 3 of 7 mice with MTAP−/− tumors. Consistent with this observation, PEG-MTAP increased the survival of mice with the B16-F10 MTAP−/− tumors, as shown in FIG. 5C.

CD8+ T-cells are required for effective treatment by PEG-MTAP, as shown in FIG. 6. C57/BL6 mice were subcutaneously inoculated with 5×10^4 B16-F10 melanoma cells with an MTAP deletion. When the tumors reached a mean size of 55 mm³, the mice were treated with either control an isotype antibody or anti-CD8 antibody, with or without 50 mg/kg of a MTAP three times/week by peri-tumoral injection for 2 weeks. As before, the MTAP treatment delayed tumor growth, and two out of six mice achieved complete remission (CR) (FIGS. 6A & 6C). Depletion of CD8+ T-cells using an anti-CD8 antibody enhanced tumor growth in the control mice (FIG. 6B) and blocked the beneficial effects of the MTAP polypeptide (FIG. 6D). These results suggest that CD8+ T-cells are able to reduce tumor growth when MTA is depleted from the tumor microenvironment by administering MTAP. Similar results would be expected with the PEGylated MTAP variants described in Example 2.

PEG-MTAP treatment results in a higher number of tumor infiltrating lymphocytes in the tumor microenvironment, including CD8+/K167+, CD4+/K167+, and CD8+/GranzymeB+ T-cells, as shown in FIG. 7. T-cell proliferation status is also rescued upon in vivo treatment with PEG-MTAP. Similar results would be expected with the PEGylated MTAP variants of Example 2.

Figure 8A:
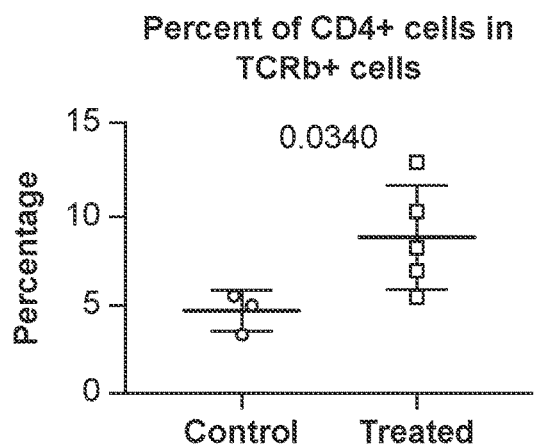
FIGS. 8A-C. Effect of PEGylated hs-MTAP polypeptides (PEG-hs-MTAP) on lymphocyte populations in the B16−MTAP−/− melanoma tumor model.
Figure 8B:
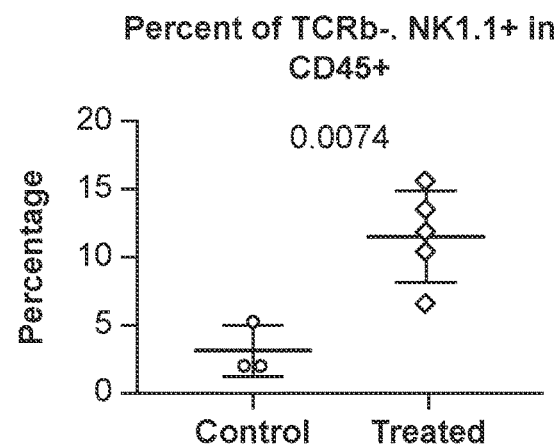
Figure 8C:
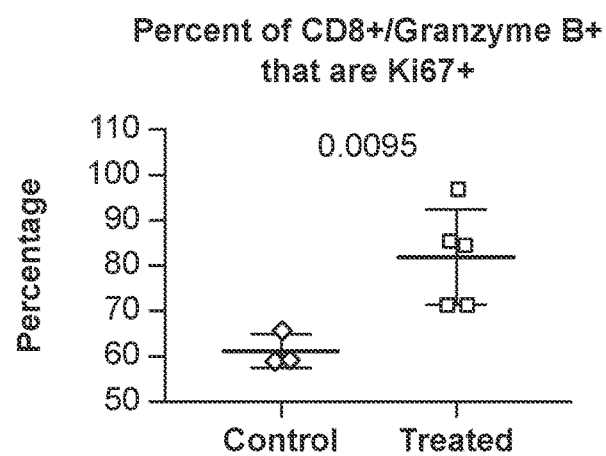

Treatment with PEG-MTAP also increases immune cell infiltration of B16-F10 melanoma allografts. Lymphocyte panels observed by FACS analyses from C57/BL6 mice bearing B16-F10 MTAP−/− tumor samples were assessed after treatment with two doses of PEG-MTAP or vehicle (analyzed 24 hr post dose). Treated groups exhibited large increases in the percentages of CD4+ T cells and NK1.1$^+$ natural killer cells and large increases in the percentage of proliferating CD8+ Granzyme B$^+$ T cells as compared to vehicle treated controls (FIGS. 8A-C). Similar results would be expected with the PEGylated MTAP variants described in Example 2.

Example 5: Treatment of L1210 Mouse Leukemia Allografts by Degrading MTA

Figure 9B:
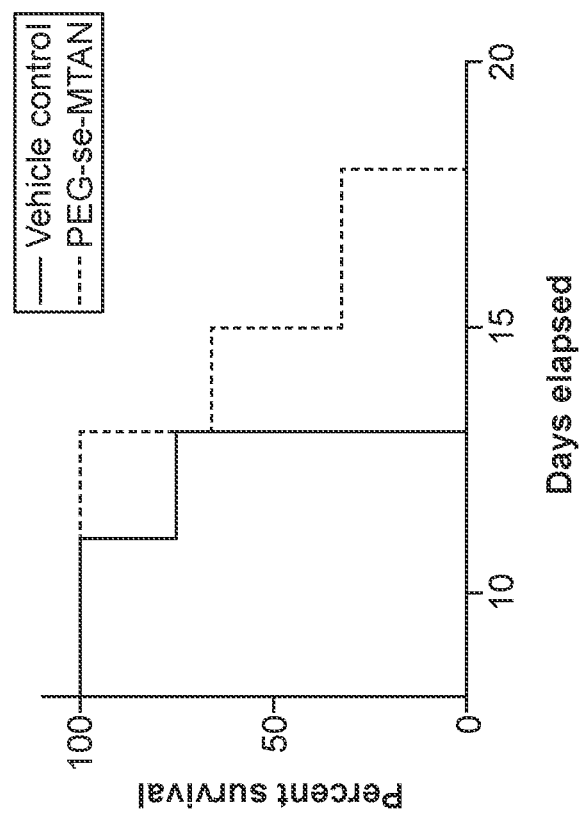
FIGS. 9A-B. Cancer therapy with MTAN polypeptides.
Figure 9A:
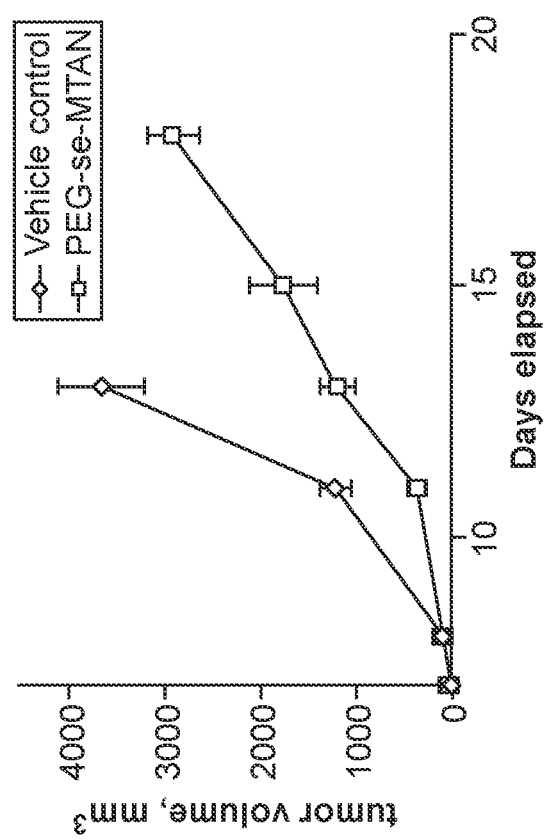

The *Salmonella enterica* enzyme, methylthioadenosine nucleosidase (MTAN) also metabolizes MTA. DBA/2 mice (n=17) were each inoculated with 5×10^4 cells of the highly aggressive L1210 murine leukemia cell line by subcutaneous flank injection. After allowing tumors to establish for an additional eight days (tumor mean=90 mm$^3$), the mice were split into two groups. The control group (n=8) was treated with PBS vehicle control by peri-tumoral injection every three days until tumors reached >2500 mm$^3$ in size. The experimental group (n=9) was treated in an identical manner except with 50 mg/kg of active PEG-se-MTAN by peri-tumoral injection every three days until tumors reached an endpoint of >2500 mm$^3$ in size. The growth rates of L1210 leukemia tumors were significantly (3.5-fold) reduced in the treatment group administered PEG-se-MTAN compared to the vehicle control group (FIG. 9A) resulting in a statistically significant life-span extension, p<0.0035 (FIG. 9B). Similar results would be expected with the PEGylated MTAP variants described in Example 2.

Figure 10C:
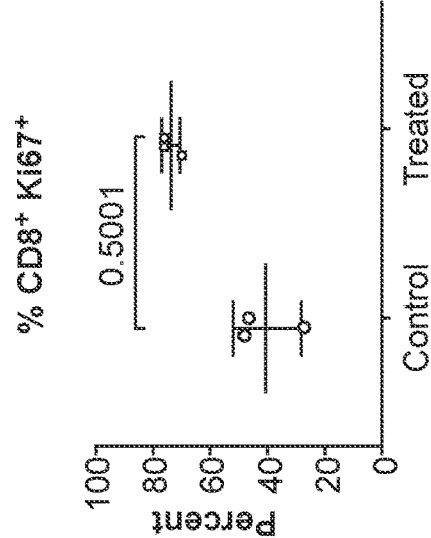
FIGS. 10A-F. Assessment of lymphocyte subtypes in tumors and tumor draining lymph nodes (TDLNs) of L1210 leukemia cell allografts treated with PEG-se-MTAN polypeptides. In tumors, PEG-se-MTAN administration increased the TCRβ+ cells as a percentage of CD45+ viable cells (FIG. 10A), and CD4+ Ki67+ cells (FIG. 10B) and CD8+ Ki67+ cells (FIG. 10C) as a percentage of all viable cells. In TDLNs, administration of PEG-MTAN increased the TCRβ+ cells (FIGURE. 10D), CD11b+ cells (FIG. 10E), and F4/80+ cells (FIG. 10F) as a percentage of all viable cells.
Figure 10B:
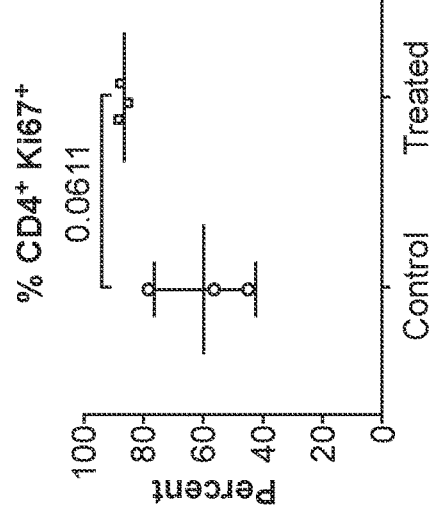
Figure 10A:
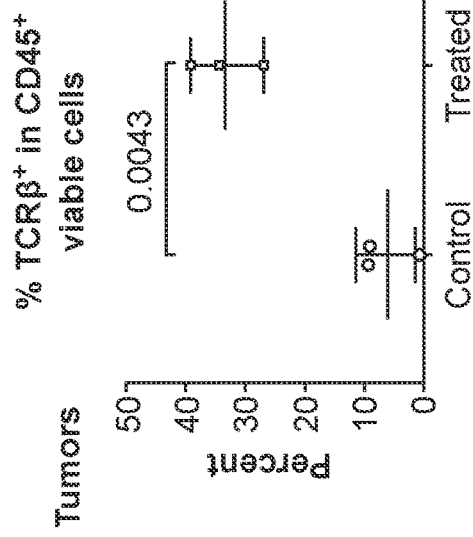
Figure 10F:
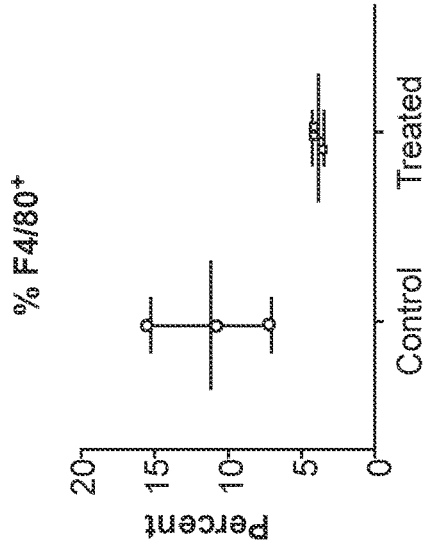
Figure 10E:
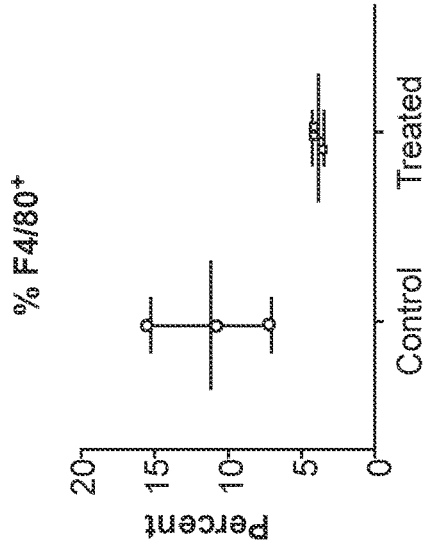
Figure 10D:
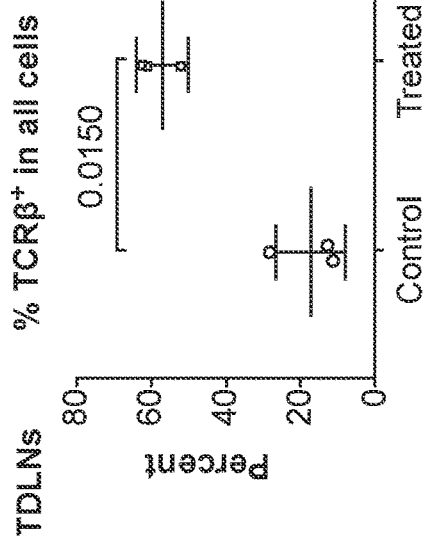

PEG-se-MTAN also increased lymphocyte infiltration into L1210 mouse leukemia allografts. Lymphocyte panels observed by FACS analyses from the tumors and tumor draining lymph nodes (TDLNs) of DBA/2 mice bearing L1210 allografts following three treatments of PEG-MTAN or vehicle control were assessed. PEG-MTAN administration resulted in large increases in the populations of tumor infiltrating lymphocytes (TILs) with greatly enhanced proliferation in CD4+ and especially CD8+ T cells consistent with the in vitro observations (FIGS. 10A-C). Very importantly, treated TDLNs also showed large increases in T cells and reduced populations of myeloid derived cells (FIGS. 10D-F) indicative of enhanced T cell activation. Similar results would be expected with the PEGylated MTAP variants of Example 2.

Figure 11A:
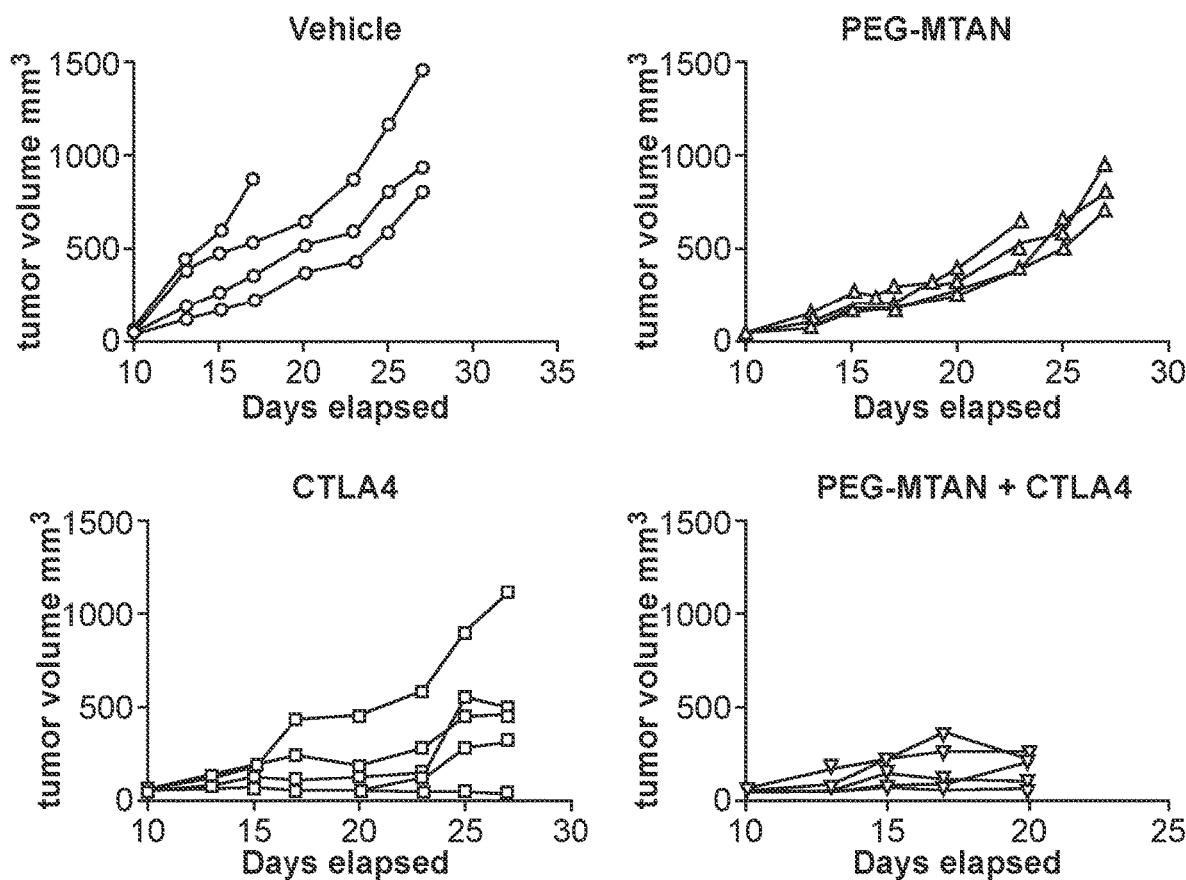
FIGS. 11A-B. Efficacy of a combination treatment with a PEG-MTAN polypeptide and anti-CTLA4 antibody of murine 4T1 breast carcinoma allografts.
Figure 11B:
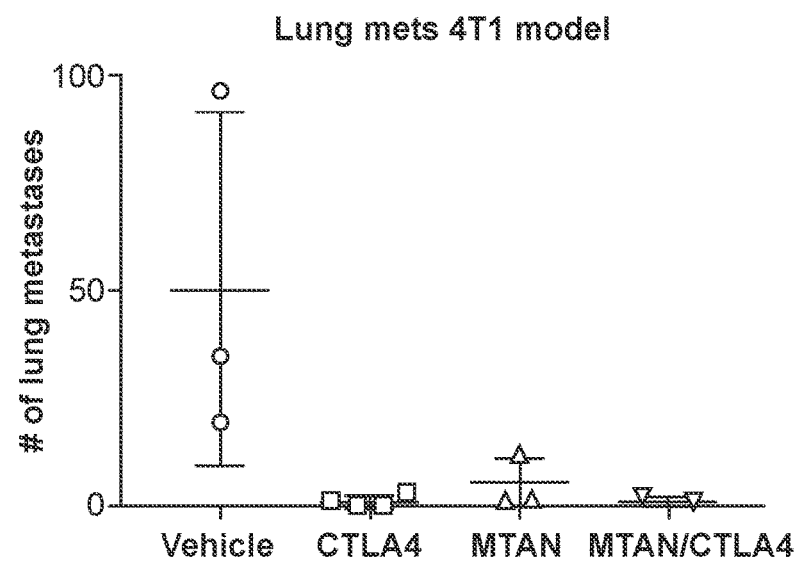
Figure 12A:
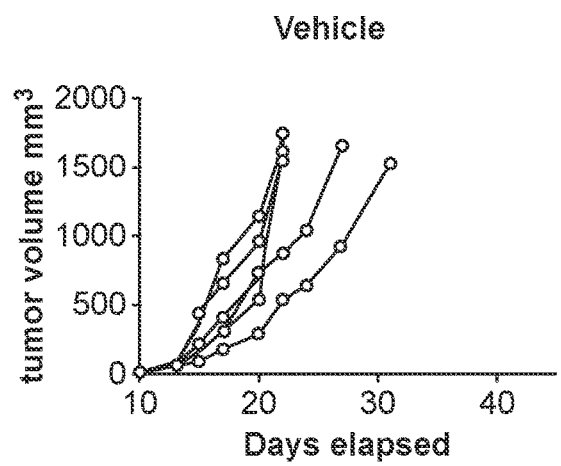
FIGS. 12A-D. Efficacy of a combination treatment with a PEG-MTAN polypeptide and anti-PD-1 antibody of murine CT26 colon carcinoma allografts (MTAP$^{low}$ CD73+). A vehicle control (FIG. 12A), anti-PD-1 antibody (clone RMP1-14, BioXCell #BE0146, 10 mg/kg 2× week) (FIG. 12B), PEG-MTAN (50 mg/kg 3× week) (FIG. 12C), or PEG-MTAN and anti-PD-1 antibody in combination (FIG. 12D) were administered on day 15 and day 25 after implantation of the CT26 carcinoma allografts. While individual administration of the PEG-MTAN polypeptide or the anti-PD-1 antibody suppressed the growth of the tumor, their combination provided a stronger inhibition than either treatment alone. Furthermore, complete remission (CR) was observed in 3 mice that received the combination treatment, whereas only 1 mouse achieved a CR with either treatment alone.
Figure 12B:
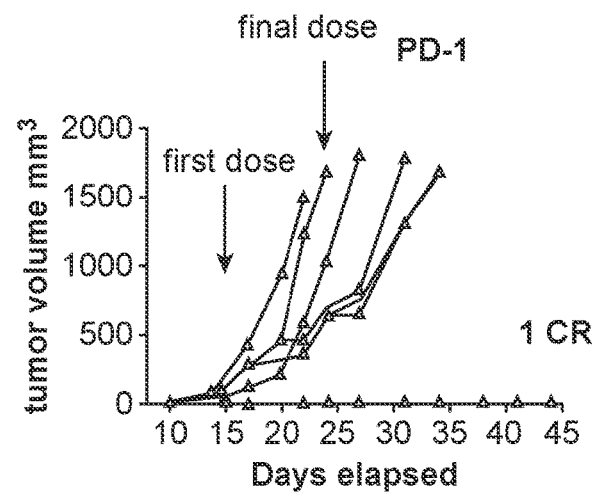
Figure 12C:
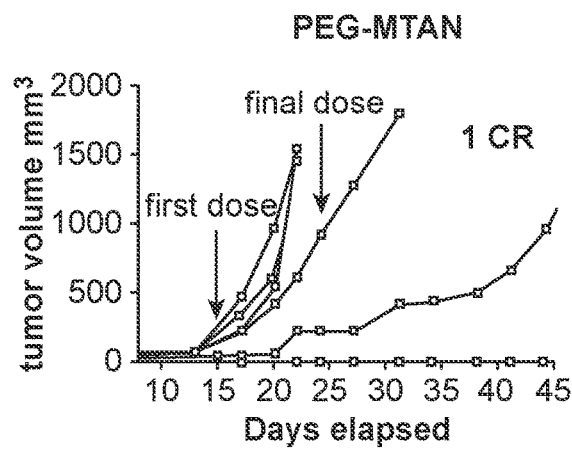
Figure 12D:
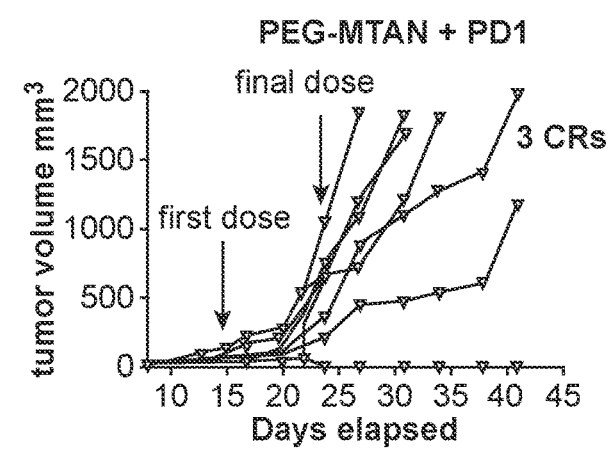

Example 6: Efficacy of PEG-MTAN/Anti-CTLA4 Treatment of Murine 4T1 Breast Carcinoma Allografts To assess the efficacy of controlling tumor growth by depletion of ADO and in combination with anti-CTLA4 antibody immune checkpoint inhibition, four cohorts of BALB/C mice were inoculated with 50,000 4T1 cells in the mammary fat pad and allowed to establish tumors. 4T1 is an MTAP$^{high}$ CD73+ tumor model where it is expected to have ADO in the tumor microenvironment but not MTA. Mice were treated with either a vehicle, PEG-MTAN (50 mg/kg), anti-CTLA4 antibody (10 mg/kg, clone UC10-4F10-11, Bio X Cell), or the combination of PEG-MTAN/anti-CTLA4 antibody. Both PEG-MTAN and anti-CTLA4 single agent arms retarded primary tumor growth and the combination was more effective, indicative of at least therapeutic additivity (FIG. 11A). As 4T1 forms pulmonary metastases, lung tissues were examined to quantify tumor colonization. All treated groups displayed significantly fewer metastatic tumor lung nodes (FIG. 11B) as compared to the vehicle control group and exemplifying the role of ADO upon metastasis. Similar results would be expected with the PEGylated MTAP variants of Example 2.

Example 7: Efficacy of PEG-MTAN Polypeptides/Anti-PD-1 Antibody Treatment of Murine CT26 Colon Carcinoma Allografts (MTAP$^{low}$ CD73+)

The CT26 cell line is known to be homozygous null for CDKN2 (Castle et al, 2014), which is commonly co-deleted with MTAP; however, it was found that while MTAP is not deleted, its expression is severely impaired. Furthermore, this cell line expresses CD73 (Sun et al, 2017) and is thus expected to produce adenosine in the tumor microenvironment. To examine any potential efficacy of ADO and/or MTA depletion in an MTAP$^{low}$ CD73+ tumor model as a single agent or in combination with anti-PD-1 antibody immune checkpoint inhibitor therapy, four groups of Balb/c mice bearing CT26 tumors were treated with either an isotype control antibody, PEG-MTAN polypeptide (50 mg/kg 3× week), anti-PD-1 antibody (clone RMP1-14, BioXCell #BE0146, 10 mg/kg 2× week), or PEG-MTAN and anti-PD-1 in combination for a total of 2 weeks. Compared to controls, both anti-PD-1 antibody and PEG-MTAN polypeptide elicited heteroscedastic effects but importantly yielded a complete remission (CR) in both single agent arms. Strikingly the anti-PD-1/PEG-MTAN combo showed tumor growth inhibition in the entire group and led to three complete responses (FIGS. 12A-D) suggestive of additive or synergistic efficacy.

Similar results would be expected with the PEGylated MTAP variants of Example 2. Other cancer or disease can also be targeted by treatments described herein if a defect in the methylthioadenosine phosphorylase activity contributes to the cancer or disease.

Figure 13:
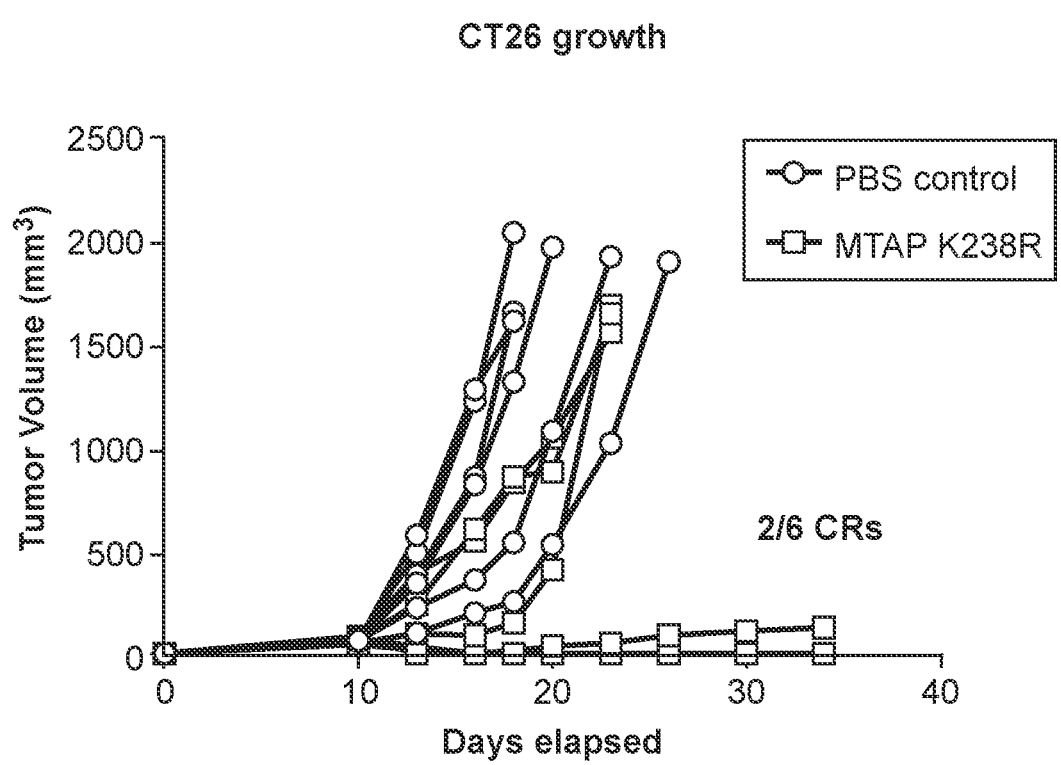
FIG. 13 shows the growth of CT26 cell allograft tumors in mice treated with or without a PEGylated MTAP K238R polypeptide (MTAP K238R). The PEGylated MTAP K238R treatment reduced the growth of CT26 tumors compared to that of the PBS control. Moreover, complete remission (CR) was observed in two out of six mice treated with the PEGylated MTAP K238R polypeptide.

Example 8: Efficacy of Highly PEGylated PEG-MTAP Polypeptides Against CT26 Allograft Tumors Two groups of Balb/c mice bearing CT26 tumors were treated with either PBS or with 50 mg/kg 3× week of the highly PEGylated MTAP K238 variant polypeptide of Example 2. The highly PEGylated MTAP K238 variant reduced tumor growth and caused complete remission in two of six treated mice (FIG. 13).

Example 9: Assay for Measuring Kinetic Parameters of an MTAP Polypeptide

Provided herein are methods of measuring the kinetic parameters of MTA degradation and adenine production by an MTAP polypeptide.

The kinetic parameters of an MTAP polypeptide or PEGylated MTAP polypeptide are quantified by a spectrophotometric assay, in which the decay in the maximum absorbance of the enzyme substrate, MTA, was monitored as a function of time as described elsewhere (Singh et al, 2004). MTA solutions are prepared in PBS (pH 7.4) to result in final concentrations ranging from 6 mM to 200 pM. MTA has a difference in extinction coefficient of 1,600 $M^{-1}cm^{-1}$ from its degradation product adenine at a $\lambda_{max}$ at 275 nm, while the other products of the reactions, methylthioribose-1'-phosphate/methylthioribiose, do not appreciably absorb at 275 nm. Reactions are initiated by adding and rapidly mixing enzyme solutions (final concentration: ~10 nM) with the substrate solutions and monitoring the loss of substrate MTA at 37° C. by measuring the absorbance at 275 nm over time. The resulting data is processed and fitted to the Michaelis-Menten equation for determining kinetic constants. The kinetic parameters, such as $V_{max}$, $V_0$, $k_{cat}$, $K_M$, their derivatives, or others are calculated.

Example 10: Kinetic Stability of an MTase Polypeptide

The kinetic stabilities of the PEGylated hs-MTAP polypeptides of Examples 1 and 2 and the PEGylated se-MTAN of Example 5 were determined by incubating the enzymes in a 100 mM phosphate buffer (pH 7.4) at 37° C. Over the course of four days, aliquots of the MTAP polypeptide were withdrawn from the incubations and assessed for their ability to degrade MTA as described in Example 9. The resulting data were processed and fitted to an exponential equation to determine the decay rate. Under these conditions, a PEGylated hs-MTAP polypeptide of Example 2 was found to have a half-life (T½) of 57 hrs, and se-MTAN in Example 5 was found to have a similar T½ of 56 hrs.

Example 11: In Vivo Stability of an MTase Polypeptide

The in vivo stability of an MTAP polypeptide or a PEG-MTAP polypeptide is determined by intravenous injection of the polypeptide into a mammalian or human subject. Blood samples are collected at various time points. An ELISA assay is used to quantify the amount of the polypeptide in plasma or serum. The serum half-life is determined as the time when the concentration of the polypeptide falls by half after the injection into the subject.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,846,945
U.S. Pat. No. 5,889,155
U.S. Pat. Publn. 2009/0304666
Appleby et al, The structure of human 5'-deoxy-5'-methylthioadenosine phosphorylase at 1.7 Å resolution provides insights into substrate binding and catalysis, Structure. June 15; 7(6):629-41, 1999.
Austin-Ward and Villaseca, Revista Medica de Chile, 126 (7):838-845, 1998.
Ausubel et al, Current Protocols in Molecular Biology, Greene Publishing Associates and Wiley Interscience, N.Y., 1994.
Bertino et al, Targeting tumors that lack methylthioadenosine phosphorylase (MTAP) activity: current strategies. Cancer Biology & Therapy, 11(7): 627-632, 2011.
Bradford et al, Adenosine deaminase (ADA)-deficient severe combined immune deficiency (SCID): molecular pathogenesis and clinical manifestations. Journal of Clinical Immunology, 37(7): 626-637, 2017.
Bukowski et al, Signal transduction abnormalities in T lymphocytes from patients with advanced renal carcinoma: clinical relevance and effects of cytokine therapy. Clinical Cancer Res., 4(10):2337-2347, 1998.
Camacho et al, Phase 1 clinical trial of anti-CTLA4 human monoclonal antibody CP-675,206 in patients (pts) with advanced solid malignancies. J Clin Oncology, 22(145): Abstract No. 2505 (antibody CP-675206), 2004.
Camacho-Vanegas et al, Primate genome gain and loss: a bone dysplasia, muscular dystrophy, and bone cancer syndrome resulting from mutated retroviral-derived MTAP transcripts. The American Journal of Human Genetics, 90(4): 614-627, 2012.
Castle et al, Immunomic, genomic and transcriptomic characterization of CT26 colorectal carcinoma. BMC Genomics, 15: 190, 2014.
Christodoulides et al, Immunization with recombinant class 1 outer-membrane protein from *Neisseria meningitidis*: influence of liposomes and adjuvants on antibody avidity, recognition of native protein and the induction of a bactericidal immune response against meningococci. Microbiology, 144(Pt 11):3027-3037, 1998.
Davidson et al, Intralesional Cytokine Therapy in Cancer: A Pilot Study of GM-CSF Infusion in Mesothelioma. J. Immunother., 21(5):389-398, 1998.
Foye et al, Foye's Principles of Medicinal Chemistry, Lippincott Williams & Wilkins, 2007.
Gao et al, Loss of IFN-γ Pathway Genes in Tumor Cells as a Mechanism of Resistance to Anti-CTLA-4 Therapy. Cell, October 6; 167(2):397-404, 2016
Gill and von Hippel, Calculation of protein extinction coefficients from amino acid sequence data. Anal Biochem, 182(2):319-326, 1989.
Hanibuchi et al, Therapeutic efficacy of mouse-human chimeric anti-ganglioside GM2 monoclonal antibody against multiple organ micrometastases of human lung cancer in NK cell-depleted SCID mice. Int. J. Cancer, 78(4):480-485, 1998.
Harkki et al, A Novel Fungal Expression System: Secretion of Active Calf Chymosin from the Filamentous Fungus *Trichoderma Reesei*. BioTechnology, 7:596-603, 1989.

Hellstrand et al, Histamine and cytokine therapy. Acta Oncologica, 37(4):347-353, 1998.

Henrich et al, Suppressive effects of tumor cell-derived 5'-deoxy-5'-methylthioadenosine on human T cells. OncoImmunology, 5(8): e1184802, 2016.

Hollander, Immunotherapy for B-cell lymphoma: current status and prospective advances. Front. Immun., 3:3, 2012.

Hopwood et al, In: Genetic Manipulation of *Streptomyces*, A Laboratory Manual, The John Innes Foundation, Norwich, Conn., 1985.

Hoover et al, The structure of human macrophage inflammatory protein-3 alpha/CCL20.

Hurwitz et al, CTLA-4 blockade synergizes with tumor-derived granulocyte-macrophage colony-stimulating factor for treatment of an experimental mammary carcinoma. Proc Natl Acad Sci USA, 95(17): 10067-10071, 1998.

Linking antimicrobial and CC chemokine receptor-6-binding activities with human beta-defensins. J Biol Chem, 277(40):37647-37654, 2002.

Hui and Hashimoto, Pathways for Potentiation of Immunogenicity during Adjuvant-Assisted Immunizations with *Plasmodium falciparum* Major Merozoite Surface Protein 1. Infection Immun., 66(11):5329-5336, 1998.

Ito et al, Purification and Characterization of Methioninase from *Pseudomonas putida*. J. Biochem., 79: 1263-1272, 1976.

Jena, Dotti et al, Blood, August 19; 116(7):1035-44, 2010.

Jiang et al, Comprehensive evaluation of NT5E/CD73 expression and its prognostic significance in distinct types of cancers. BMC Cancer, 18:267, 2018.

Kadariya et al, Mice heterozygous for germ-line mutations in methylthioadenosine phosphorylase (MTAP) die prematurely of T-cell lymphoma. Cancer Research, 69(14): 5961-5969, 2009.

Keyel et al, Methylthioadenosine reprograms macrophage activation through adenosine receptor stimulation. PLoS One, 9(8): e104210, 2014.

Kim et al, Downregulation of methylthioadenosin phosphorylase by homozygous deletion in gastric carcinoma. Genes, Chromosomes and Cancer, 50(6): 421-433, 2011.

Kirovski et al, Down-regulation of methylthioadenosine phosphorylase (MTAP) induces progression of hepatocellular carcinoma via accumulation of 5'-deoxy-5'-methylthioadenosine (MTA). American Journal of Pathology, 178(3): 1145-1152, 2011

Iordanescu, Recombinant plasmid obtained from two different, compatible staphylococcal plasmids. J. Bacteriol, 12:597-601, 1975.

Maniatis et al, Molecular Cloning, A Laboratory Manual, Cold Spring Harbor Press, Cold Spring Harbor, N.Y., 1988.

Marjon et al. MTAP Deletions in Cancer Create Vulnerability to Targeting of the MAT2A/PRMT5/RIOK1. Axis. Cell Rep. April 19; 15(3):574-587 2016.

Mellor et al, Efficient synthesis of enzymatically active calf chymosin in *Saccharomyces cerevisiae*. Gene, 24: 1-14, 1983.

Mokyr et al, Realization of the Therapeutic Potential of CTLA-4 Blockade in Low-Dose Chemotherapy-treated Tumor-bearing Mice. *Cancer Res,* 58:5301-5304, 1998.

Morello et al, Soluble CD73 as biomarker in patients with metastatic melanoma patients treated with nivolumab. Journal of Translational Medicine, 15:244, 2017.

Nassar et al, A model combining clinical and genomic factors to predict response to PD-1/PD-L1 blockade in advanced urothelial carcinoma. Br. J. Cancer, February; 122(4):555-563, 2020.

Nechushtan et al, Adenocarcinoma cells are targeted by the new GnRH-PE66 chimeric toxin through specific gonadotropin-releasing hormone binding sites. J Biol Chem, April 25; 272(17):11597-603, 1997.

Onda et al, In vitro and in vivo cytotoxic activities of recombinant immunotoxin 8H9(Fv)-PE38 against breast cancer, osteosarcoma, and neuroblastoma. Cancer Research, February 15; 64(4):1419-24, 2004.

Park, Rosenberg et al, Treating cancer with genetically engineered T cells. Trends Biotechnol, November; 29(11):550-7, 2011.

Penttila et al, A versatile transformation system for the cellulolytic filamentous fungus *Trichoderma reesei*. Gene, 61: 155-164, 1987.

Peters et al, A mouse model for cystinuria type I. Hum Mol Genet 12: 2109-2120, 2003.

Qin et al, Interferon-0 gene therapy inhibits tumor formation and causes regression of established tumors in immune-deficient mice. Proc. Natl. Acad. Sci. USA, 95(24): 14411-14416, 1998.

Remington's Pharmaceutical Sciences, 18th Ed. Mack Printing Company, 1289-1329, 1990.

Rizvi et al, Molecular Determinants of Response to Anti-Programmed Cell Death (PD)-1 and Anti-Programmed Death-Ligand 1 (PD-L1) Blockade in Patients With Non-Small-Cell Lung Cancer Profiled With Targeted Next-Generation Sequencing. J. Clin. Oncol, March 1; 36(7): 633-641, 2018

Schneider et al, 671 nih image to imageJ: 25 years of image analysis. Nature Methods, 9:2012.

Sek et al., Targeting Adenosine Receptor Signaling in Cancer Immunotherapy. International J. of Mol. Sciences, 19:3837, 2018.

Sibakov et al., Isolation and the 5'-end nucleotide sequence of *Bacillus licheniformis* a-amylase gene. Eur. J. Biochem., 145:567-572, 1984.

Singh et al, Picomolar transition state analogue inhibitors of human 5'-methylthioadenosine phosphorylase and X-ray structure with MT-Immucillin-A. Biochemistry, 43(1): 9-18, 2004.

Stevens et al, Quantification of intermediates of the methionine and polyamine metabolism by liquid chromatography-tandem mass spectrometry in cultured tumor cells and liver biopsies. Journal of Chromatography, A 1217 (19): 3282-3288, 2010.

Stevens et al, Quantitative analysis of 5'-deoxy-5'-methylthioadenosine in melanoma cells by liquid chromatography-stable isotope ratio tandem mass spectrometry. Journal of Chromatography B, 876(1): 123-128, 2008.

Stevens et al, Direct and tumor microenvironment mediated influences of 5'-deoxy-5'-(methylthio) adenosine on tumor progression of malignant melanoma. Journal of Cellular Biochemistry, 106(2): 210-219, 2009.

Stone et al, Strategies for optimizing the serum persistence of engineered human arginase I for cancer therapy. Journal of Controlled Release, 158: 171-179, 2012.

Strobl, Schaffer et al, https://pubmed.ncbi.nlm.nih.goelective PRMT5 Inhibitors Suppress Human CD8+ T Cells by Upregulation of p53 and Impairment of the AKT Pathway Similar to the Tumor Metabolite MTA. Molecular Cancer Therapeutics, February; 19(2):409-419, 2020

Sun et al., Fasting inhibits colorectal cancer growth by reducing M2 polarization of tumor-associated macrophages. Oncotarget, 8:74649-74660, 2017.

Tiziani et al, Optimized metabolite extraction from blood serum for 1H nuclear magnetic resonance spectroscopy. Analytical Biochemistry, 377: 16-23, 2008.

Tiziani et al, Metabolomics of the tumor microenvironment in pediatric acute lymphoblastic leukemia. PLoS One, 8:e82859, 2013.

Vandenbark et al, Inhibition of lymphocyte transformation by a naturally occurring metabolite: 5'-Methylthioadenosine. Cellular Immunology, 49(1): 26-33, 1980.

Vijayan et al, Targeting immunosuppressive adenosine in cancer. Nature Reviews Cancer, 17:709, 2017.

von Minckwitz et al, Phase I clinical study of the recombinant antibody toxin scFv(FRP5)-ETA specific for the ErbB2/HER2 receptor in patients with advanced solid malignomas. Breast Cancer Research, 7(5):R617-26, 2005.

Ward, Proc, Embo-Alko Workshop on Molecular Biology of Filamentous Fungi, Helsinki, 119-128, 1989.

Wawrzynczak and Thorpe, In Immunoconjugates, Antibody Conjugates In Radioimaging And Therapy Of Cancer, Vogel (Ed.), NY, Oxford University Press, 28, 1987.

Webb, Amici et al, PRMT5-Selective Inhibitors Suppress Inflammatory T Cell Responses and Experimental Autoimmune Encephalomyelitis. Journal of Immunology, February 15; 198(4):1439-1451, 2017.

Winthrop et al, Selection and characterization of anti-MUC-1 scFvs intended for targeted therapy. Clinical Cancer Research, September 1; 9(10 Pt 2):38455-535, 2003.

Woollard et al, Independent Loss of Methylthioadenosine Phosphorylase (MTAP) in Primary Cutaneous T-Cell Lymphoma. Journal of Investigative Dermatology, 136 (6): 1238-1246, 2016.

Yu et al, Ecto-5'-nucleotidase expression is associated with the progression of renal cell carcinoma. Oncology Letters, 9:2485-2494, 2015.

The invention claimed is:

1. A composition comprising a polypeptide having methylthioadenosine phosphorylase activity,
   wherein said polypeptide comprises an amino acid sequence with at least 95% sequence identity to at least 100 consecutive amino acids of SEQ ID NO: 1 and comprises amino acids corresponding to Threonine 18, Threonine 197, Serine 178, Valine 233 and Methionine 196 of SEQ ID NO: 1, and
   wherein an amino acid corresponding to Lysine 225 or Lysine 238 of SEQ ID NO: 1 is (i) deleted or (ii) substituted with Alanine, Arginine, Asparagine, Aspartic Acid, Cysteine, Glutamine, Glutamic Acid, Glycine, Histidine, Isoleucine, Leucine, Methionine, Phenylalanine, Proline, Serine, Threonine, Tryptophan, Tyrosine, or Valine.

2. The composition of claim 1, wherein said amino acid corresponding to Lysine 225 is substituted with said Arginine.

3. The composition of claim 1, wherein said amino acid corresponding to Lysine 238 is substituted with said Arginine.

4. The composition of claim 1, wherein said polypeptide comprises an amino acid sequence comprising a sequence with at least 95% sequence identity to SEQ ID NO: 3 or SEQ ID NO: 5.

5. The composition of claim 1, wherein said polypeptide comprises the amino acid sequence of SEQ ID NO: 3 or SEQ ID NO: 5.

6. The composition of claim 5, wherein said polypeptide is conjugated to a polymer.

7. The composition of claim 6, wherein said polymer is a polyethylene glycol polymer.

8. The composition of claim 7, wherein said polyethylene glycol polymer has an average molecular weight of about 4,000 kilodaltons (kDa) to about 8,000 kDa.

9. The composition of claim 7, wherein said composition comprises at least six of said polyethylene glycol polymers.

10. The composition of claim 7, wherein said composition comprises a plurality of said polypeptides, and wherein a number of said polyethylene glycol polymers per polypeptide comprises a Gaussian distribution with a mode of 8±3 of said polyethylene glycol polymers per polypeptide.

11. The composition of claim 10, wherein said polypeptide comprises the amino acid sequence of SEQ ID NO: 5.

12. The composition of claim 1, where said polypeptide is conjugated to a polymer, and wherein said polymer is not conjugated to an amino acid corresponding to either of Lysine 225 or Lysine 238 of SEQ ID NO. 1.

13. The composition of claim 12, wherein said composition comprises at least six of said polymers.

14. The composition of claim 13, wherein a $k_{cat}/K_M$ of said methylthioadenosine phosphorylase activity of said polypeptide is at least 50% of a $k_{cat}/K_M$ of a methylthioadenosine phosphorylase comprising SEQ ID NO: 1.

15. The composition of claim 13, wherein a $k_{cat}/K_M$ of said methylthioadenosine phosphorylase activity of said polypeptide is at least $1.5 \times 10^5$ $M^{-1}s^{-1}$.

16. The composition of claim 13, wherein a Vmax of said methylthioadenosine phosphorylase activity of said polypeptide is at least 50% of a Vmax of said methylthioadenosine phosphorylase activity of a methylthioadenosine phosphorylase comprising SEQ ID NO: 1.

17. The composition of claim 13, wherein a Km of said methylthioadenosine phosphorylase activity of said polypeptide is no more than twice a Km of said methylthioadenosine phosphorylase activity of a methylthioadenosine phosphorylase comprising SEQ ID NO: 1.

18. The composition of claim 12, wherein said polypeptide has a serum half-life of at least 36 hours.

19. A composition comprising a population of said polypeptides according to claim 1, wherein said population comprises trimers of said polypeptides.

* * * * *